United States Patent [19]

Draper et al.

[11] Patent Number: 5,972,704
[45] Date of Patent: *Oct. 26, 1999

[54] HIV NEF TARGETED RIBOZYMES

[75] Inventors: Kenneth G. Draper; Bharat Chowrira; James McSwiggen; Dan T. Stinchcomb; James D. Thompson, all of Boulder, Colo.

[73] Assignee: Ribozyme Pharmaceuticals, Inc., Boulder, Colo.

[*] Notice: This patent is subject to a terminal disclaimer.

[21] Appl. No.: 08/910,408

[22] Filed: Aug. 13, 1997

Related U.S. Application Data

[63] Continuation of application No. 08/271,880, Jul. 7, 1994, Pat. No. 5,693,535, which is a continuation-in-part of application No. 07/882,886, May 14, 1992, abandoned, and application No. 08/103,423, Aug. 6, 1993, abandoned.

[51] Int. Cl.$^6$ .............................. C12Q 1/68; C07H 21/04
[52] U.S. Cl. .......................... 435/375; 435/6; 435/91.31; 435/172.3; 435/320.1; 435/325; 435/366; 536/23.1; 536/23.2; 536/24.5
[58] Field of Search ........................ 435/6, 91.31, 172.3, 435/320.1, 325, 366, 375; 536/23.1, 23.2, 24.5; 514/44

[56] References Cited

U.S. PATENT DOCUMENTS

| | | | |
|---|---|---|---|
| 4,987,071 | 1/1991 | Cech et al. | 435/91.31 |
| 5,144,019 | 9/1992 | Rossi et al. | 536/23.2 |
| 5,149,796 | 9/1992 | Rossi et al. | 536/23.2 |
| 5,168,053 | 12/1992 | Altman et al. | 435/91.31 |
| 5,278,956 | 1/1994 | Hampel et al. | 536/23.2 |
| 5,527,895 | 6/1996 | Hampel et al. | 536/23.2 |

FOREIGN PATENT DOCUMENTS

| | | |
|---|---|---|
| 0331939 | 9/1989 | European Pat. Off. . |
| 0360257 | 3/1990 | European Pat. Off. . |
| 9115500 | 1/1991 | WIPO . |
| 9103162 | 3/1991 | WIPO . |
| 9104319 | 4/1991 | WIPO . |
| 9104324 | 4/1991 | WIPO . |
| 9110453 | 7/1991 | WIPO . |
| 9115580 | 10/1991 | WIPO . |
| 9201806 | 2/1992 | WIPO . |
| 9305147 | 3/1993 | WIPO . |
| 9323569 | 11/1993 | WIPO . |

OTHER PUBLICATIONS

Barinaga, "Ribozymes: Killing the Messenger," *Science* 262:1512–1514 (1993).
Bartel et al., "HIV–1 Rev Regulation Involves Recognition of Non–Watson–Crick Base Pairs in Viral RNA," *Cell* 67:529 (1991).
Braun et al., "In Vitro Cleavage of HIV–1 vif RNA By a Synthetic Ribozyme," *Virus Genes* 5:17 (1991) (Abstract).
Beckett and Uhlenbeck, in *Oligonucleotide Synthesis: A Practical Approach*, Ch. 8 "Enzymatic Synthesis of Oligoribonucleotides," M.J. Gait, Ed., 1984 IRL Press, Ltd.
Block et al., "Innovations in Antiviral Development and the Detection of Virus Infection," Plenum Press, New York pp. 125–128 (1992).
Cameron et al., "Specific Gene Expression by Engineered Ribozymes in Monkey Cells," *Proc. Natl. Acad. Sci. USA* 86:9139–9143 (1989).
Cech, "Ribozymes and Their Medical Implications," *JAMA* 260:3030 (1988).
Chang et al., "Ribozyme–Mediated Site–Specific Cleavage of the HIV–1 Genome" *Clinical Biotechnology* 2:23 (1990).
Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).
Cheng–Mayer et al., "Differential Effects of nef on HIV Replication: Implications for Viral Pathogenesis in the Host," *Science* 246:1629 (1989).
Crisell et al., "Inhibition of HIV–1 Replication by Ribozymes That Show Poor Activity in vitro," *Nucleic Acids Research* 21;5251–5255 (1993).
Dropulic et al., "Functional Characterization of a U5 Ribozyme: Intracellular Suppression of Human Immunodeficiency Virus Type I Expression," *Journal of Virology* 66:1432–1441 (1992).
Gallo et al., *Cancer Res.* 43:3892 (1983).
Guatelli and Richman, "Development of Hammerhead Ribozymes as Inhibitors of HIV–1 Replication," *J. Cellular Biochem.* Supplement 16E:79 at Q521 (1992).
Guerrier–Takada et al., "The RNA Moiety of Ribonuclease P Is the Catalytic Subunit of the Enzyme", *Cell* 35:849 (1983).
Hampel et al., "RNA Catalyst for Cleaving Specific RNA Sequences," filed Sep. 20, 1989, which is a Continuation-–in–Part of U.S. Serial No. 07/247,100 filed Sep. 20, 1988.
Hampel et al., "Hairpin' Catalytic RNA Model: Evidence for Helices and Sequence Requirement for Substrate RNA", *Nucleic Acids Research* 18:299 (1990).
Hampel and Tritz, "RNA Catalytic Properties of the Minimum (–)sTRSV Sequence," *Biochemistry* 28:4929 (1989).
Haseloff and Gerlach, "Simple RNA Enzymes with New and Highly Specific Endoribonuclease Activities," *Nature* 334:585 (1988).
Heidenreich and Eckstein, "Hammerhead Ribozyme–mediated Cleavage of the Long Terminal Repeat RNA of Human Immunodeficiency Virus Type 1," *Journal of Biological Chemistry* 267:1904–1909 (1992).
Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159–10171 (1990).

(List continued on next page.)

*Primary Examiner*—John L. LeGuyader
*Attorney, Agent, or Firm*—Lyon & Lyon LLP

[57] ABSTRACT

An enzymatic nucleic acid molecule which cleaves an immunodeficiency virus RNA in a gene required for viral replication, e.g., the nef or tat gene regions.

22 Claims, 20 Drawing Sheets

OTHER PUBLICATIONS

Jeang and Berkhout, "Kinetics of HIV–1 Long Terminal Repeat trans–Activation," *J. Biol. Chem.* 267:17891 (1992).

Jeffries and Symons, "A Catalytic 13–mer Ribozyme," *Nucleic Acids Research* 17:1371–1377 (1989).

Johnston and Hoth, "Present Status and Future Prospects for HIV Therapies," *Science* 260:1286–1293 (1993).

Joseph and Burke, "Optimization of an Anti–HIV Hairpin Ribozyme by in Vitro Selection," *J. Biol. Chem.* 268:24515–24518 (1993).

Kim and Cech, "Three–dimensional model of the active site of the self–splicing rRNA precursor of Tetrahymena," *Proc. Natl. Acad. Sci. USA* 84:8788 (1987).

Lingelbach et al., "An Extended RNA/RNA Duplex Structure Within the Coding Region of mRNA Does Not Block Translational Elongation," *Nucleic Acids Research* 16:3405–3414 (1988).

Lorentzen et al., "In Vitro Cleavage of HIV–1 vif RNA by a Synthetic Ribozyme," *Virus Genes* 5:17 (1991).

Le Guern et al., "Human Immunodeficiency Virus (HIV) Type 1 Can Superinfect HIV–2–infected Cells: Pseudotype Virions Produced with Expanded Cellular Host Range," *Proc. Natl. Acad. Sci. USA* 89:363 (1992).

Malim et al., "Functional Comparison of the Rev Trans–activators Encoded by Different Primate Immunodeficiency Virus Species" *Proc. Natl. Acad. Sci. USA* 86:8222 (1989).

Mamone et al., "Design of Mannerhead Ribozymes Targeted to Sequences in HIV, HSV, and the Rat ANF Gene," Abstract of Keystone, CO (May 27, 1992).

Matsukura et al., "Regulation of Viral Expression of Human Immunodeficiency Virus in vitro by an Antisense Phosphorothioate Oligodeoxynucleotide Against rev (art/trs) in Chronically Infected Cells," *Proc. Natl. Acad. Sci. USA* 86:4244 (1989).

Ojwang et al., "Inhibition Of Human Immunodeficiency Virus Type 1 Expression By A Hairpin Ribozyme", *Proc. Natl. Acad. Sci. USA* 89:10802–10806 (1992).

Pavco et al., "Regulation of Self–Splicing Reactions by Antisense RNA", Abstract of Keystone, CO (May 27, 1992).

"The Papovaviridae", Ed. Salzman et al., vol. 2, *The Viruses*, Plenum Press, NY 1987.

Perrotta and Been, "Cleavage of Oligoribonucleotides by a Ribozyme Derived from the Hepatitis δ Virus RNA Sequence," *Biochemistry* 31:16 (1992).

Ratner et al., "Complete nucleotide sequence of the AIDS virus, HTLV–III," *Nature* 313:277–284 (1985).

Rossi et al., "Ribozymes As Therapies For AIDS", *Annals of the New York Academy of Sciences* 606:184–200 (1990).

Rossi et al., "Ribozyme Mediated Intracellular Immunity to HIV–1 in CD4," *J. Cell Biochem.* Suppl 14A:374 at D428 (1990).

Rossi et al., "Ribozymes as Anti–HIV–1 Therapeutic Agents: Principles, Applications, and Problems," *Aids Research and Human Retroviruses* 8:183 (1992).

Sambrook et al., *Molecular Cloning: A Laboratory Manual*, Cold Spring Harbor Laboratory Press, New York, pp. 7.71–7.78 (1989).

Sarver et al., "Ribozymes as Potential Anti–HIV–1 Therapeutic Agents" *Science* 247:1222 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Sioud and Drlica, "Prevention of Human Immunodeficiency Virus Type 1 Integrase Expression in *Escherichia coli* by a Ribozyme" *Proc. Natl. Acad. Sci. USA* 88:7303 (1991).

Slim et al., "Configurationally Defined Phosphorothioate––Containing Oligoribonucleotides in the Study of the Mechanism of Cleavage of Hammerhead Ribozymes," *Nucleic Acids Research* 19:1183–1188 (1991).

Slim et al., "Synthesis of site–specifically modified oligoribonucleotides for studies of the recognition of TAR RNA by HIV–1 tat protein and studies of hammerhead ribozymes," *Nucleic Acids Research*, Symposium Series No. 24, pp. 55–58 (1991).

Stull and Szoka, "Antigene, Ribozyme and Aptamer Nucleic Acid Drugs: Progress and Prospects," *Pharmaceutical Research* 12:465–483 (1995).

Taylor and Rossi, "Ribozyme–Mediated Cleavage of an HIV–1 gag RNA: The Effects of Nontargeted Sequences and Secondary Structure on Ribozyme Cleavage Activity," *Antisense Res. and Dev.* 1:173–186 (1991).

Terwilliger et al., "Allelic Variation in the Effects of the nef gene on Replication of Human Immunodeficiency Virus Type 1" *Proc. Natl. Acad. Sci. USA* 88:10971 (1991).

Tsukiyama–Kohara et al., "Internal Ribosome Entry Site Within Hepatitis C Virus RNA," *Journal of Virology* 66:1476 (1992).

Usman et al., "Automated Chemical Synthesis of Long Oligoribonucleotides Using 2'–O–Silylated Ribonucleoside 3'–O–Phosphoramidtes on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Viscidi et al., "Inhibition of Antigen–Induced Lymphocyte Proliferation by Tat Protein from HIV–1" *Science* 246:1606 (1989).

von Weizsacker, et al., "Cleavage of hepatitis B virus RNA by three ribozymes transcribed from a single DNA template," *Biochemical and Biophysical Research Communications* 189:743–748 (Dec. 15, 1992).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Viology* 65:5531 (1991).

Xing et al., "Ribozymes Which Cleave Arenavirus RNAs: Identification of Susceptible Target Sites and Inhibition by Target Site Secondary Structure" *Journal of Virology* 66:1361–1369 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zaia et al., "Status of Ribozyme and Antisense–Based Developmental Approaches for Anti–HIV–1 Therapy," *Annals of the New York Acad of Sci.* 660:95 (1992).

Slim et al. Nuclice Acids Symp. Ser. 1991 (24) pp. 55–58.

Stull et al. Pharm. Res. 12:465–483 (1995).

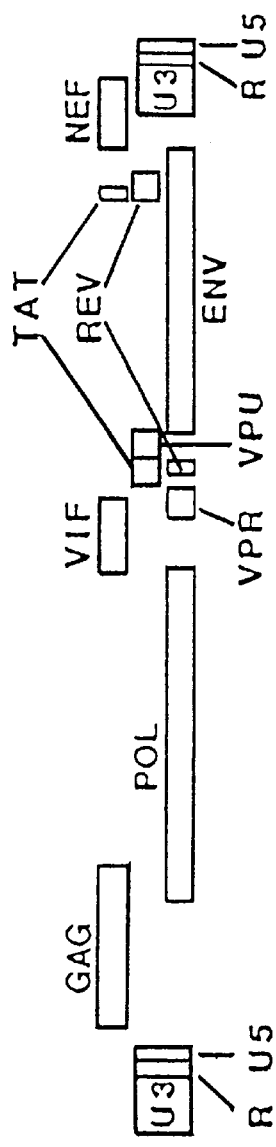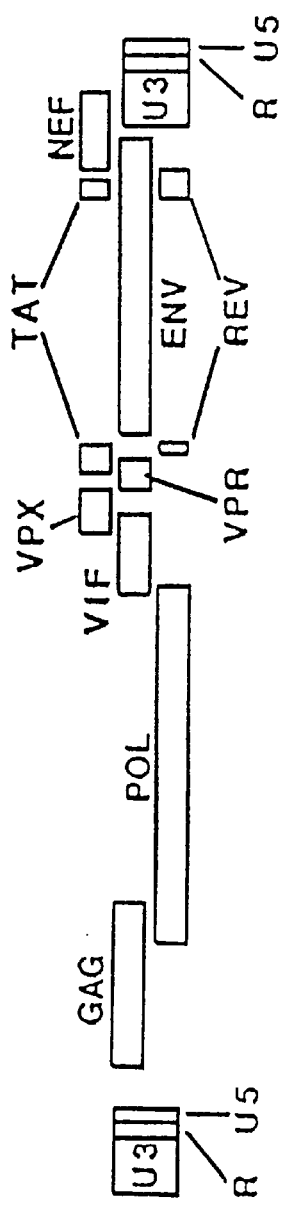
FIG. 2a.

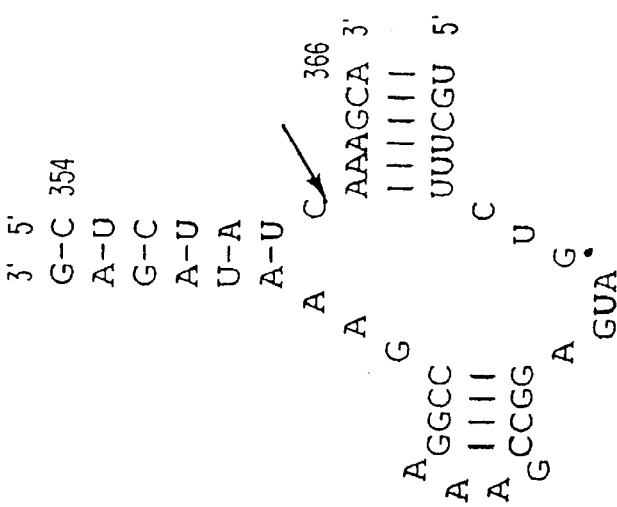
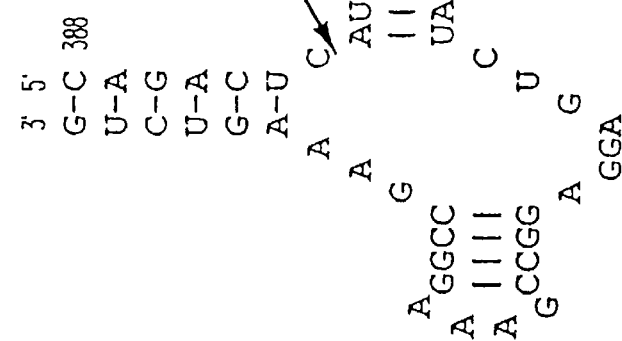
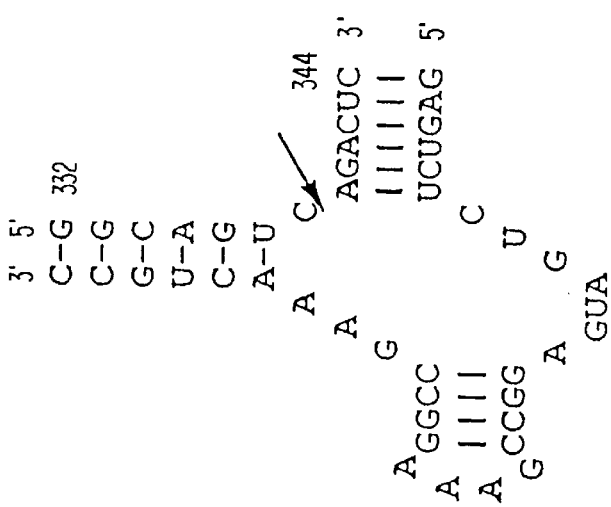

FIG. 7.

Chimeric Hammerhead Ribozymes

| RPI | 3'-end | CORE | STEM/LOOP II | 5'-end | ACTIVITY |
|---|---|---|---|---|---|
| 1197 | • | • | • | • | 1 |
| 1200 | OMe | • | • | OMe | 0.7 |
| 1315 | DNA | • | DNA | DNA | 0.02 |
| 1370 | Allyl | • | • | Allyl | 1 |
| 1371 | Ara | • | • | Ara | 0 |
| 1414 | OMe/FU | FU7 | • | OMe/FU | 0.5 |
| 1368 | • | T7 | • | • | 0.7 |
| 1431 | OMe | NH2-U4·7 | • | OMe | 0.5 |
| 1394 | OMe | • | • | OMe | 0 (46-mer) |
| 1285 | • | • | -4 bp | • | 0.1 (28-mer) |

Relative Nuclease Resistance of Modified Ribozymes

| RPI | 3'-end | CORE | 5'-end | RELATIVE RESISTANCE MONO | LYMPH | |
|---|---|---|---|---|---|---|
| 1197 | • | • | • | 1 | 1 | |
| 1200 | O-Me | • | O-Me | 2 | 2 | |
| 1370 | O-Allyl | • | O-Allyl | 3 | 2 | |
| 1414 | O-Me/FU | FU7 | O-Me/FU | 3 | 1 | |
| 1368 | • | T7 | • | 3 | 1 | |
| 1431 | O-Me | NH2-U4+7 | O-Me | • | 2 | |
| 1394 | O-Me | • | O-Me | 3 | 4 | (46-mer) |

Nuclease Resistant Ribozyme Fragments

| RPI | 3'-end | CORE | 5'-end | 5'-FRAGMENT | | 3'-FRAGMENT | |
|---|---|---|---|---|---|---|---|
| | | | | MONO | LYMPH | MONO | LYMPH |
| 1197 | • | • | • | 2 | 2, 9 | 20, 23 | 20, 23 |
| 1200 | O-Me | • | O-Me | 4, 14 | 9 | 20, 23 | 20, 23 |
| 1370 | O-Allyl | • | O-Allyl | 2 | 2, 9 | 20, 23 | 20, 23 |
| 1414 | O-Me/FU | FU7 | O-Me/FU | 2 | 9, 13 | 20, 23 | 20, 23 |
| 1368 | • | T7 | • | 3 | 2, 9 | 20, 23 | 20, 23 |
| 1431 | O-Me | NH2-U4+7 | O-Me | 3, 12 | 9, 13 | 20, 23 | 20, 23 |
| 1394 | O-Me | • | O-Me | 2, 12 | 9, 13 | 8 | 8 |
| | | | | | | | (46-mer) |

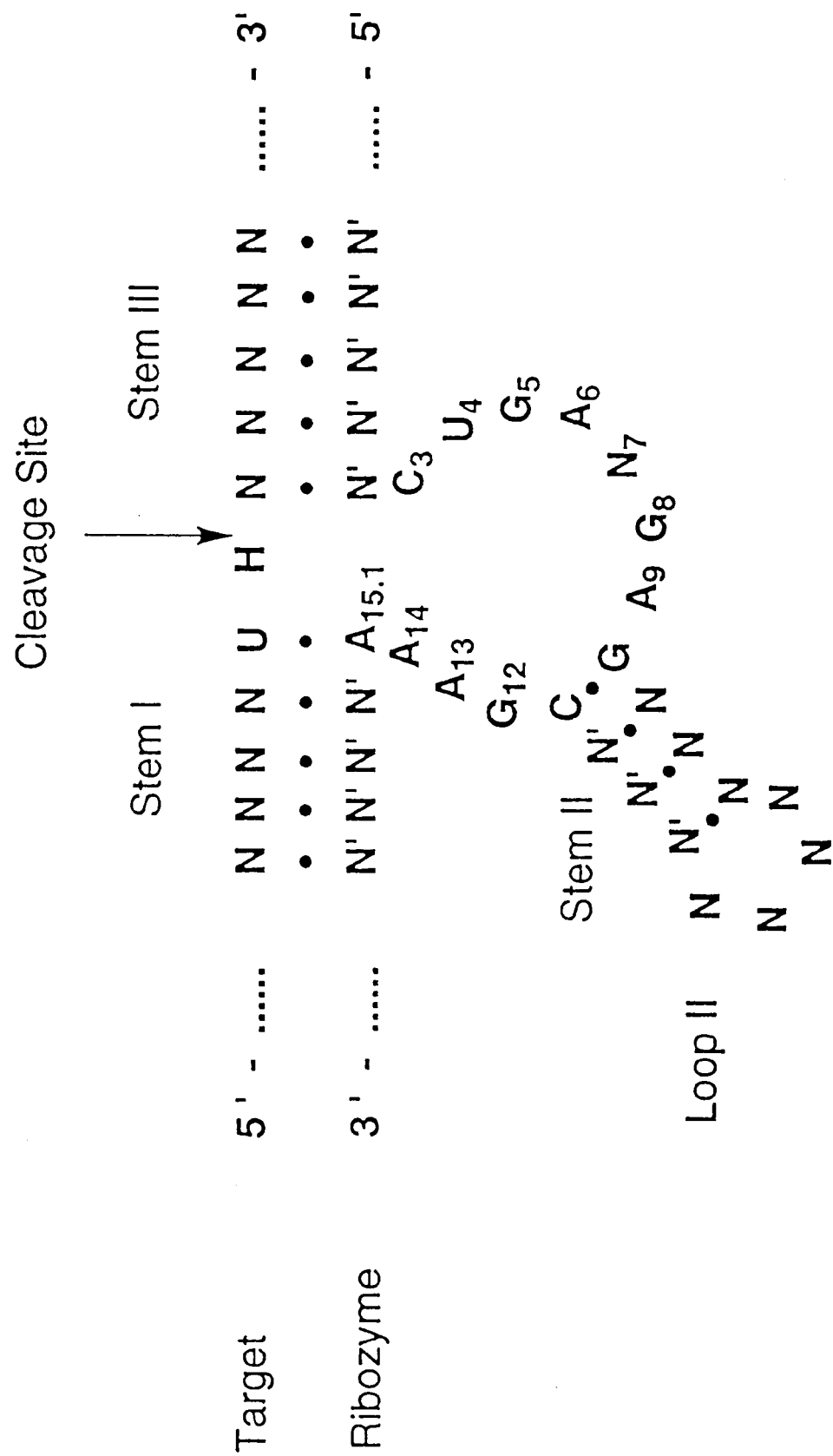
FIG. 14. The Hammerhead Ribozyme

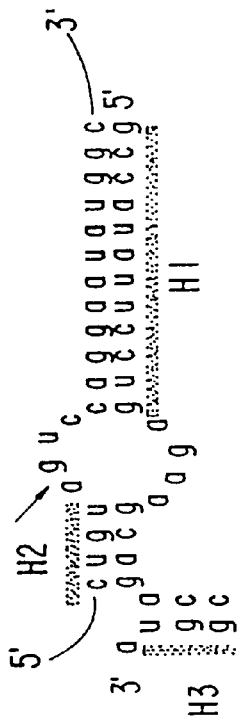
FIG. 15b.
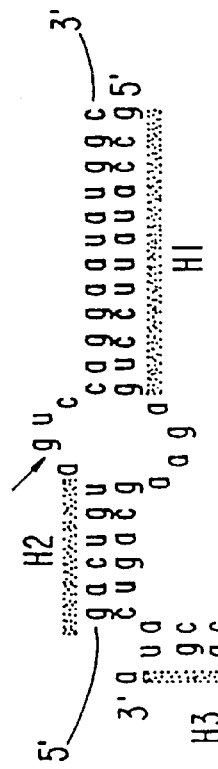
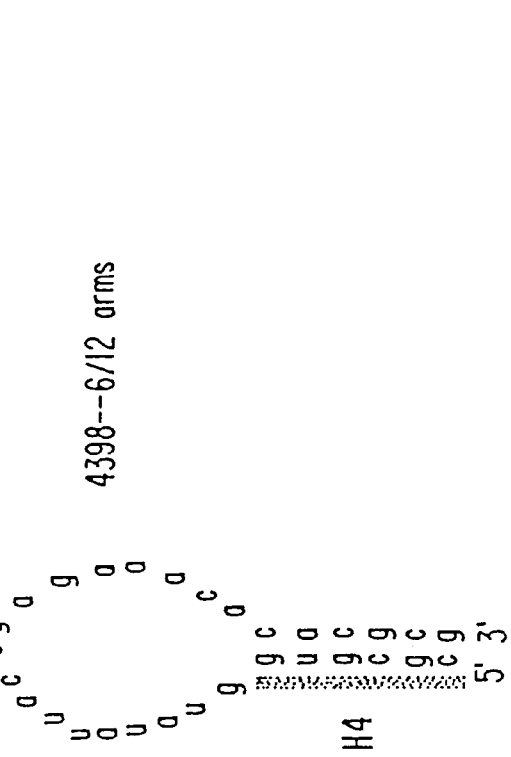
FIG. 15a.

HIV NEF TARGETED RIBOZYMES

This is a continuation of application Ser. No. 08/271,880 filed Jul. 7, 1994, now U.S. Pat. No. 5,693,575 hereby incorporated by reference in its totality (including drawings), which is a continuation-in-part of Draper, U.S. Ser. No. 07/882,886, filed May 14, 1992, now abandoned, and U.S. Ser. No. 08/103,423, filed Aug. 6, 1993, now abandoned, both entitled "Method and Reagent for Inhibiting Human Immunodeficiency Virus Replication," assigned to the same assignee as the present application, the whole of which (including drawings) are hereby incorporated by reference herein and are abandoned in favor of the present application.

BACKGROUND OF THE INVENTION

This invention relates to the use of ribozymes as inhibitors of human immunodeficiency virus (HIV) replication, and in particular, the inhibition of HIV-1 replication. See e.g., Draper et al., PCT/WO93/23569 hereby incorporated by reference.

Acquired immunodeficiency syndrome (AIDS) is thought to be caused by infection with the virus HIV-1. At present, it is treated by administration of the drug azidothymidine (AZT), which is thought to slow the progress of, but not cure, the disease. AZT resistant strains of HIV-1 are found to develop after a year of treatment. In some patients AZT has limited efficacy and may be found intolerable. More recently, drugs such as dideoxyinosine (DDI) and dideoxycytidine (DDC) have been tested as treatments for AIDS. None of these compounds reduce the viral load in patients, but they do treat the disease symptoms.

The following is a discussion of relevant art, none of which is admitted to be prior art to the pending claims. Rossi et al., 8 *Aids Research and Human Retroviruses* 183, 1992, provide a review of the use of ribozymes as anti-HIV-1 therapeutic agents. They state:

> An emerging strategy in the treatment of viral infections is the use of antisense DNA or RNA to pair with, and block expression of viral transcripts. RNA, in addition to being an informational molecule, can also possess enzymatic activity. Thus, by combining anti-sense and enzymatic functions into a single transcript, it is now possible to design catalytic RNAs, or ribozymes, which can specifically pair with virtually any viral RNA, and cleave the phosphodiester backbone at a specified location, thereby functionally inactivating the viral RNA. In carrying out this cleavage, the ribozyme is not itself altered, and is thus capable of recycling and cleaving other molecules, making it a true enzyme. There are several different catalytic motifs which possess enzymatic activity, and each one of these can be incorporated into an enzymatic antisense with site-specific cleavage capabilities.

Rossi et al. also state that studies have demonstrated that a hammerhead ribozyme targeted to the gag gene RNA in the vicinity of the translational initiation codon is capable of specifically cleaving that target in a complex milieux of total cellular RNA. With reference to identification of ribozyme targets in HIV-1 they state that mRNAs for the two regulatory proteins tat and rev are clearly targets of choice, and that they are examining potential ribozyme cleavage sites in the tat mRNA, as well as in the exon shared by tat and rev. In addition, they state:

> A rational approach to the problem of target selection involves the following criteria. First, one should select a functionally important target, such as tat, rev, int, psi (packaging site), or the $tRNA^{lys}$ priming site. Once a gene or target region has been decided upon, the nucleotide sequence should be assessed for strong conservation of sequence among the various isolates. Within these conserved regions, the potential cleavage sites, preferably G UC or GUA (others will suffice, but appear to be less efficiently cleaved) should be chosen. The region should be examined for potential secondary structures, and then the most promising sites chosen. Finally, before testing the ribozyme in cell culture, it is advisable to carry out a series of in vitro cleavage reactions (preferably kinetic analyses) using long (at least 100 nucleotides in length) substrates to verify that the chosen sites are truly structurally favorable for cleavage. [Citation omitted.]

Rossi et al. further state that a target which deserves further consideration and testing as a potential ribozyme cleavage site is the viral packaging signal or psi sequence.

Sioud and Drlica, 88 *Proc. Natl. Acad. Sci. USA* 7303, 1991 describe ribozymes designed to cleave the integrase gene of HIV. They state that when the ribozyme is transcribed from a plasmid in *E. coli* it leads to destruction of the integrase RNA and complete blockage of integrase protein synthesis. They state that the HIV-1 integrase gene may be a useful target for therapeutic ribozymes.

Heidenreich and Eckstein, 267 *Journal of Biological Chemistry* 1904, 1992, describe three ribozymes targeted to different sites on the long terminal repeat (LTR) RNA of HIV-1. They also describe the influence of chemical modifications within the ribozyme on the cleavage of the LTR RNA, including 2'-Fluorocytidine substitutions and phosphorothioate internucleotidic linkages.

Weerasinghe et al., 65 *Journal of Virology* 5531, 1991, describe ribozymes designed against a conserved region within the 5' leader sequence of HIV-1 RNA.

Chang et al., 2 *Clinical Biotechnoloqy* 23, 1990, describe ribozymes designed to target two different sites in the HIV-1 gag gene, and a single site in the viral 5'-LTR region.

Lorentzen et al., 5 *Virus Genes* 17, 1991, describe a ribozyme targeted to the virion infectivity factor (vif) of HIV-1.

Sarver et al., 247 *Science* 1222, 1990, describe ribozymes in the hammerhead family targeted to HIV-1 gag transcripts. They state that cells challenged with HIV-1 showed a substantial reduction in the level of HIV-1 gag RNA relative to that in nonribozyme-expressing cells, and that the reduction in gag RNA was reflected by a reduction in antigen p24 levels. They state that the results suggest the feasibility of developing ribozymes as therapeutic agents against human pathogens such as HIV-1.

Hampel et al., "RNA Catalyst for Cleaving Specific RNA Sequences," filed Sep. 20, 1989, which is a continuation-in-part of U.S. Ser. No. 07/247,100, filed Sep. 20, 1988, describe hairpin ribozymes, and provides an example of such a ribozyme apparently specific to the gag gene of HIV-1. Hampel and Tritz, 28 *Biochemistry* 4929, 1989 and Hampel et al., 18 *Nucleic Acids Research* 299, 1990 also describe hairpin catalytic RNA models and state that one target site is the tat gene in HIV-1.

Goldberg et al., WO 91/04319 and Robertson and Goldberg WO 91/04324, describe ribozymes expressed within a hepatitis delta vector and state that the genome of the delta virus may carry a ribozyme against the env or gag mRNA of HIV. Rossi et al., WO 91/03162, describe chimeric DNA-RNA catalytic sequences used to cleave HIV-1 gag transcript or the 5' LTR splice site.

Ojwang et al., 89 *Proc. Natl. Acad. Sci. USA* 10, 802, 1992 and Yu et al., 90 *Proc. Natl. Acad. Sci. USA* 6340, 1993 describe a hairpin ribozyme allegedly able to inhibit HIV-1 expression. Joseph and Burke 268 *J. Biol. Chem.* 24, 515 1993, describe optimization of an anti-HIV hairpin ribozyme. Dropulic et al., 66 *J. Virology* 1432, 1992 describe a U5 ribozyme which cleaves at nucleoside +115 in HIV-1 RNA.

Other related art includes Rossi et al., U.S. Pat. Nos. 5,144,019 and 5,149,796; Altman et al., U.S. Pat. No. 5,168,053; Zaia et al., 660 *Ann. N.Y. Acad. Sci.* 95, 1992; Guatelli et al., 16E *J. Cell Biochem.* 79, 1992; Jeang et al., 267 *J. Biol. Chem.* 17891, 1992; Dropulic et al., 66 *J. Virol.* 1432, 1992; Lisziewicz et al., International Publication WO 91/10453; International Publication WO 91/15500; Rossi et al., 14A *J. Cell Biochem.* D428, 1990; and "The Papovaviridae", Ed. Salzman et al., Vol. 2, *The Viruses*, Plenum Press, NY 1987.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage has been achieved in vitro. Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of. binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

SUMMARY OF THE INVENTION

The invention features novel enzymatic RNA molecules, or ribozymes, and methods for their use for inhibiting immunodeficiency virus replication, e.g., HIV-1, HIV-2 and related viruses including FIV-1 and SIV-1. Such ribozymes can be used in a method for treatment of diseases caused by these related viruses in man and other animals. The invention also features cleavage of the RNA of these viruses by use of ribozymes. In particular, the ribozyme molecules described are targeted to the LTR, nef, vif, tat and rev viral genes or regions. These genes are known in the art, see, e.g., Matsukura et al., 86 *Proc. Natl. Acad. Sci. USA* 4244, 1989; Cheng-Mayer et al., 246 *Science* 1629, 1989; Viscidi et al., 246 *Science* 1606, 1989; Malim et al., 86 *Proc. Natl. Acad. Sci. USA* 8222, 1989; Terwilliger et al., 88 *Proc. Natl. Acad. Sci. USA* 10971, 1991; and Bartel et al., 67 *Cell* 529, 1991, and FIGS. 2A and 2B.

Thus, in a first aspect, the invention features an enzymatic RNA molecule (or ribozyme) which cleaves HIV-1 RNA, or its equivalent, regions required for viral replication, e.g., protein synthesis, e.g., the vif, nef, tat or rev gene regions, or at structures known to regulate viral gene expression, e.g., tar, rre or 3'-LTR regions.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. By "equivalent" RNA to HIV-1 is meant to include those naturally occurring RNA molecules associated with immunodeficiency diseases in various animals, including humans, felines, and simians. These viral RNAs have similar structures and equivalent genes to each other, including the vif, nef, tat and rev genes.

By "gene" is meant to refer to either the protein coding regions of the cognate mRNA, HIV genome, proviral genome or any regulatory regions in the RNA which regulate synthesis of the protein or stability of the mRNA.

In preferred embodiments, the enzymatic RNA molecule is formed in a hammerhead motif, but may also be formed in the motif of a hairpin, hepatitis delta virus, group I intron or RNaseP-like RNA (in association with an RNA guide sequence). Examples of such hammerhead motifs are described by Rossi et al. (see citations above), of hairpin motifs by Hampel et al. (see citations above), and an example of the hepatitis delta virus motif is described by Perrotta and Been, 31 *Biochemistry* 16, 1992; of the RNaseP motif by Guerrier-Takada, et al., 35 *Cell* 849, 1983; and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

In particularly preferred embodiments, the RNA which is cleaved in HIV-1 RNA is selected from one or more of the following sequences:

Sequence taken from the HIVPCV12 sequence in the Los Alamos Human Retrovirus and AIDS database. The sequence folded began at nucleotide number one of the 2.3 kb subgenomic mRNA. This region includes the coding regions for the vif, vpr, vpu, tat, rev, and nef gene products.

| Nucleotide Sequence | | |
|---|---|---|
| Number | | SEQ.ID.NO. |
| 13 | AGAAGAAAAGCAAAGAUCAUUAGGGAUUAUGGAAAACAGA | ID.NO.01 |
| 108 | AGUUUAGUAAAACAC | ID.NO.02 |
| 121 | CCAUAUGUAUAUUUC | ID.NO.03 |
| 198 | UCAGAAGUACACAUC | ID.NO.04 |
| 228 | AGAUUGGUAGUAANA | ID.NO.05 |
| 235 | AAUAACAACAUAUUGG | ID.NO.06 |
| 246 | AUUGGGGUCUGCAUA | ID.NO.07 |
| 258 | AUACAGGAGAAAGAGACUGGCAUUUGGG | ID.NO.08 |
| 280 | AUCUGGGUCAGGGAGUCUCCAUA | ID.NO.09 |
| 311 | AAAAAGAGAUAUAGCACACAAGUAGACCCU | ID.NO.10 |
| 439 | UGAAUAUCAAGCAGGACAUAACAAGGUAGGAUCUCUACAAUA | ID.NO.11 |
| 468 | AUACUUGGCACUAGCAGCAUUAAUAACACCAAAAAAGAUAAAGC | ID.NO.12 |
| 601 | CACAAUGAAUGGACACUAG | ID.NO.13 |
| 644 | AAGCUGUUAGA | ID.NO.14 |
| 683 | UAGGGCAACAUAUCUAUGAAACUUA | ID.NO.15 |
| 733 | GCCAUAAUAAGAA | ID.NO.16 |
| 800 | AUAGGCGUUAC | ID.NO.17 |
| 828 | GAAAUGGAGCC | ID.NO.18 |
| 844 | AUCCUAGACUAGAGC | ID.NO.19 |
| 875 | AAGUCAGCCUAAAA | ID.NO.20 |
| 894 | UGUACCAAUUGCUAUUGUAAAAAGUG | ID.NO.21 |
| 925 | UUCAUUGCCAAG | ID.NO.22 |
| 936 | GUUUGUUUCAUAACAAAAGCCUUAGGCAUCUCCUAUGGCAGGAA | ID.NO.23 |
| 988 | GACAGCGACGAAGAG | ID.NO.24 |
| 998 | AAGACCUCCUCAAG | ID.NO.25 |
| 1011 | GGCAGUCAGACUCAUCAAGUUUCUCU | ID.NO.26 |
| 1037 | AUCAAAGCAAC | ID.NO.27 |
| 1053 | UCCCAAUCCCGAGGGGACCCGACAGGCCCGAAGGAAUAGAAGAA | ID.NO.28 |
| 1126 | CAUUCGAUUAGUGAA | ID.NO.29 |
| 1162 | GGACGAUCUGCGGAGCCUGUGC | ID.NO.30 |
| 1260 | GGGAAGCCCUCAAAUAUUGGUGGAAUCUC | ID.NO.31 |
| 1314 | AGAAUAGUGCUG | ID.NO.32 |
| 1339 | UGCCACAGCUAUAGCA | ID.NO.33 |
| 1383 | AAGUAGUACAAGAAGCUUAUAGA | ID.NO.34 |
| 1419 | UACCUAGAAGAAUAAGACAGGGCUUGGAAAGGAU | ID.NO.35 |
| 1476 | UGGUCAAAAAGUAG | ID.NO.36 |
| 1517 | AAGAAUGAGACGAGCUGAGCCA | ID.NO.37 |
| 1557 | GGAGCAGUAUCUCGA | ID.NO.38 |
| 1568 | AGACCUAGAAAAACAUGGAGCAAUCACA | ID.NO.39 |
| 1630 | CCUGGCUAGAAGCACAAGAGGAGGAGAAGGUGGG | ID.NO.40 |
| 1674 | ACACCUCAGGUACCUUUAAGACCAAUGACUUACAAG | ID.NO.41 |
| 1710 | GCAGCUGUAGAUCUUAGCCACUUUUUAAAAGAAAAGGGGG | ID.NO.42 |
| 1747 | GGGGGACUGGAAGGG | ID.NO.43 |
| 1760 | GCUAAUUCACUCCCAACGA | ID.NO.44 |
| 1779 | AGACAAGAUAUCCUUGAUCUGUGGAUCUACCACA | ID.NO.45 |
| 1831 | AUUGGCAGAACUACACACCAGGAC | ID.NO.46 |
| 1861 | UCAGAUAUCCA | ID.NO.47 |
| 1894 | AAGCUAGUACCAGUU | ID.NO.48 |
| 1941 | GAGAACACCAGCUU | ID.NO.49 |
| 1960 | ACCCUGUGAGCCUGCAUGGAAUGGAUGAC | ID.NO.50 |
| 2008 | AGUGGAGGUUUGACAGCCGC | ID.NO.51 |
| 2065 | AGUACUUCAAGAACUGCUGAUAUCGAGCUUGCUACAAGGGAC | ID.NO.52 |
| 2188 | CUGCUUUUUGCCUGUAC | ID.NO.53 |
| 2228 | UCUGAGCCUGGGAGCUC | ID.NO.54 |
| 2281 | UAAAGCUUGCC | ID.NO.55 |
| 3'LTR: | | |
| | UGCCUGUAGAUCCUAGAC | ID.NO.56 |
| | AGCAUCCAGGAAGUCAGCC | ID.NO.57 |
| nef gene: | | |
| 8—23 | CAAGUGGUCAAAANG | ID.NO.58 |
| 93—107 | GGAGCAGUAUCUCAA | ID.NO.59 |
| 214—229 | CCNCAGGUACCUUUA | ID.NO.60 |
| 283—297 | GGGGGACUGGAUGGG | ID.NO.61 |
| vif gene: | | |
| 80—95 | CCAUAUGUAUGUUUC | ID.NO.62 |
| 187—201 | AGACUGGUAAUAANA | ID.NO.63 |
| 239—253 | AUCUGGGUCAGGGAG | ID.NO.64 |
| | AUUUGGGUCAGGGAG | ID.NO.65 |
| 247—261 | CAGGGAGUCUCCAUA | ID.NO.66 |
| 286—300 | ACACAAGUAGACCCU | ID.NO.67 |
| 418—432 | AACAAGGUAGGAUCU | ID.NO.68 |

In a second related aspect, the invention features a mammalian cell which includes an enzymatic RNA molecule as described above. Preferably, the mammalian cell is a human cell, for example, a T4 lymphocyte having a CD4 receptor molecule on its cell surface.

In a third related aspect, the invention features an expression vector which includes nucleic acid encoding the enzymatic RNA molecules described above, located in the vector, e.g., in a manner which allows expression of that enzymatic RNA molecule within a mammalian cell.

In a fourth related aspect, the invention features a method for treatment of human immunodeficiency disease by administering to a patient an enzymatic RNA molecule which cleaves HIV-1 RNA or related RNA in the vif, nef, tat or rev gene regions.

In other related aspects, the invention features treatment of cats or simians with ribozymes of this invention. Such ribozymes may be identical to those able to cleave HIV-1 RNA, or may be modified to target analogous locations in FIV and SIV virus RNAs.

The invention provides a class of chemical cleaving agents which exhibit a high degree of specificity for the viral RNA of HIV-1 type virus-infected cells. If desired, such ribozymes can be designed to target equivalent single-stranded DNAs by methods known in the art. The ribozyme molecule is preferably targeted to a highly conserved sequence region of HIV-1 such that all strains of HIV-1 can be treated with a single ribozyme. Such enzymatic RNA molecules can be delivered exogenously or endogenously to infected cells. In the preferred hammerhead motif, the small size (less than 40 nucleotides, preferably between 32 and 36 nucleotides in length) of the molecule allows the cost of treatment to be reduced compared to other ribozyme motifs.

The smallest ribozyme delivered for treatment of HIV infection reported to date (by Rossi et al., 1992, supra) is an in vitro transcript having a length of 142 nucleotides. Synthesis of ribozymes greater than 100 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, an alternative approach uses smaller ribozyme motifs (e.g., of the hammerhead structure, shown generally in FIG. 1) and exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure, or with its complementary binding of the ribozyme to the mRNA target region.

The enzymatic RNA molecules of this invention can be used to treat human immunodeficiency virus infections, including those caused by both HIV-1 and HIV-2. Such treatment can also be extended to other related viruses which infect non-human primates including the simian and feline immunodeficiency viruses. Infected animals can be treated at the time of productive infection. This timing of treatment will reduce viral loads in infected cells and disable viral replication in any subsequent rounds of infection. This is possible because the ribozymes disable those structures required for successful initiation of viral protein synthesis.

The targets chosen in the present invention provide a distinct advantage over prior targets since they act not only at the time of viral absorption or reverse transcription during infection, but also in latently infected cells and in virally transformed cells. In addition, viral particles which are released during a first round of infection in the presence of such ribozymes will still be immunogenic by virtue of having their capsids intact. Thus, one method of this invention allows the creation of defective but immunogenic viral particles, and thus a continued possibility of initiation of an immune response in a treated animal.

In addition, the enzymatic RNA molecules of this invention can be used in vitro in a cell culture infected with HIV-1 viruses, or related viruses, to produce viral particles which have intact capsids and defective genomic RNA. These particles can then be used for instigation of immune responses in a prophylactic manner, or as a treatment of infected animals.

The invention also features immunization preparations formed from defective HIV-1 particles (or related particles) created by a method of this invention, and methods for immunization or vaccination using these defective particles, e.g., with DNA or vectors encoding a ribozyme of this invention under the control of a suitable promoter.

Diagnostic Uses

Ribozymes of this invention may be used as diagnostic tools to examine genetic drift and mutations of viruses within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an HIV-1 related condition. Such RNA is detected by determining the presence of a cleavage product after treatment with a ribozyme using standard methodology.

In a specific example, ribozymes which can cleave only wild-type HIV or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., HIV) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other features and advantages of the invention will be apparent from the following description of the preferred embodiments thereof, and from the claims.

DESCRIPTION OF THE PREFERRED EMBODIMENTS

The drawings will first briefly be described.

Drawings

FIG. 1 is a diagrammatic representation of a hammerhead motif ribozyme showing stems I, II and III (marked (I), (II) and (III) respectively) interacting with an HIV-1 target region. The 5' and 3' ends of both ribozyme and target are shown. Dashes indicate base-paired nucleotides.

FIGS. 2A and 2B are diagrammatic representations of the various genes and gene regions in HIV-1 and HIV-2.

FIGS. 3A–3C are diagrammatic representations of three ribozymes of this invention.

FIG. 4A is unmodified HCH-r37, FIG. 4B is Thio-substituted HCH-r37S2, FIG. 4C is Thio-substituted HCH-r37S4, FIGS. 4D–are Thio substituted HCH-s37A–D.

FIGS. 7, 8 and 9 are diagrammatic representations of various hammerhead ribozymes along with data on activity, and nuclease resistance.

FIG. 14 is a diagrammatic representation of a hammerhead ribozyme showing base numbering. Each N and N' can be the same or different.

FIG. 15 is a diagrammatic representation of two hairpin ribozymes active on HIV RNA.

Target Sites

The genome of HIV-1 is subject to rapid genetic drift by virtue of its RNA content and the nature of errors in reverse transcription. Those regions (genes) of the genome which are essential for virus replication, however, are expected to maintain a constant sequence (i.e., are conserved) over extensive periods of time. These regions are preferred target sites in this invention since they are more likely to be conserved between different types or strains of immunodeficiency viruses, and thus only one ribozyme is needed to destroy all such viruses. Thus, one ribozyme may be used to target all HIV-1 virus, as well as all HIV-2, SIV and FIV viruses. We have selected several such genes of HIV-1, and examined their nucleotide sequences for the presence of conserved regions which may be cleaved by ribozymes targeted to those regions. Two genes analyzed in detail are the vif and nef genes; the tat, rev and other genes noted above can be analyzed in a manner similar to that described below. Nucleotide sequences were acquired from the Los Alamos HIV gene bank.

Ribozymes targeting selected regions of the HIV genome are chosen to cleave the target RNA in a manner which inhibits translation of the RNA. Genes are selected such that inhibition of translation will inhibit viral replication, e.g., by inhibiting protein synthesis. Selection of effective target sites within these critical regions of HIV-1 RNA entails testing the accessibility of the target RNA to hybridization with various oligonucleotide probes. These studies can be performed using RNA probes and assaying accessibility by cleaving the hybrid molecule with RNaseH (see below). Alternatively, such a study can use ribozyme probes designed from secondary structure predictions of the RNAs, and assaying cleavage products by polyacrylamide gel electrophoresis (PAGE), to detect the presence of cleaved and uncleaved molecules.

The following is but one example of a method by which suitable target sites can be identified and is not limiting in this invention. Generally, the method involves identifying potential cleavage sites for a hammerhead ribozyme, and then testing each of these sites to determine their suitability as targets by ensuring that secondary structure formation is minimal.

Figure 2B:
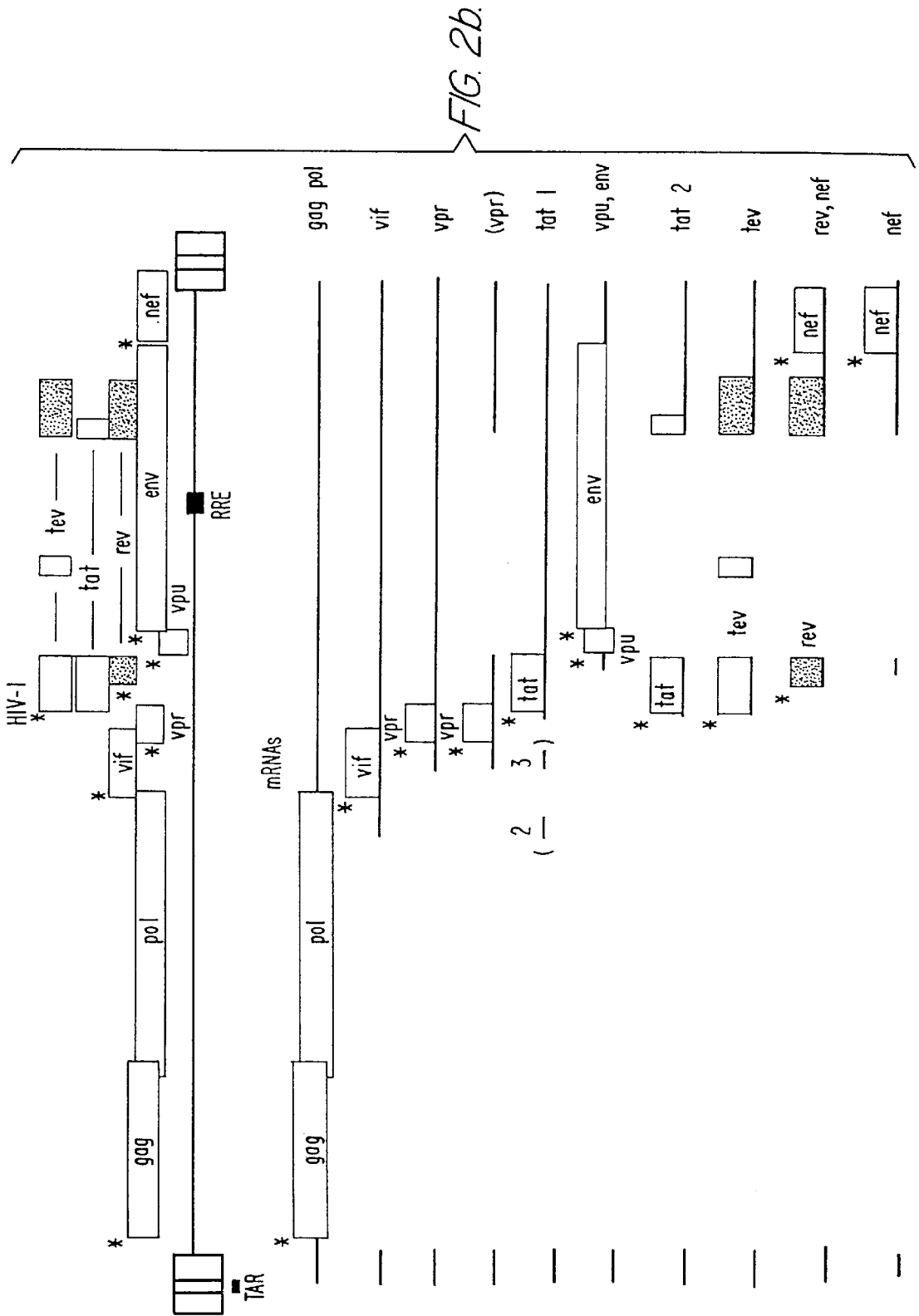
Figure 4A:
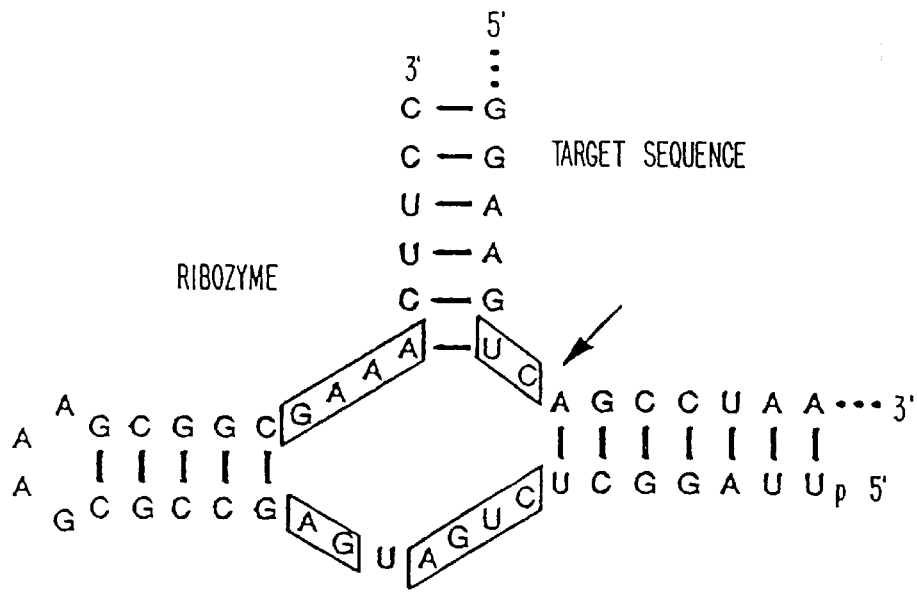
FIGS. 4A–4G are diagrammatic representations of chemically modified ribozymes of this invention (solid circles indicate modified bases). Specifically.
Figure 4B:
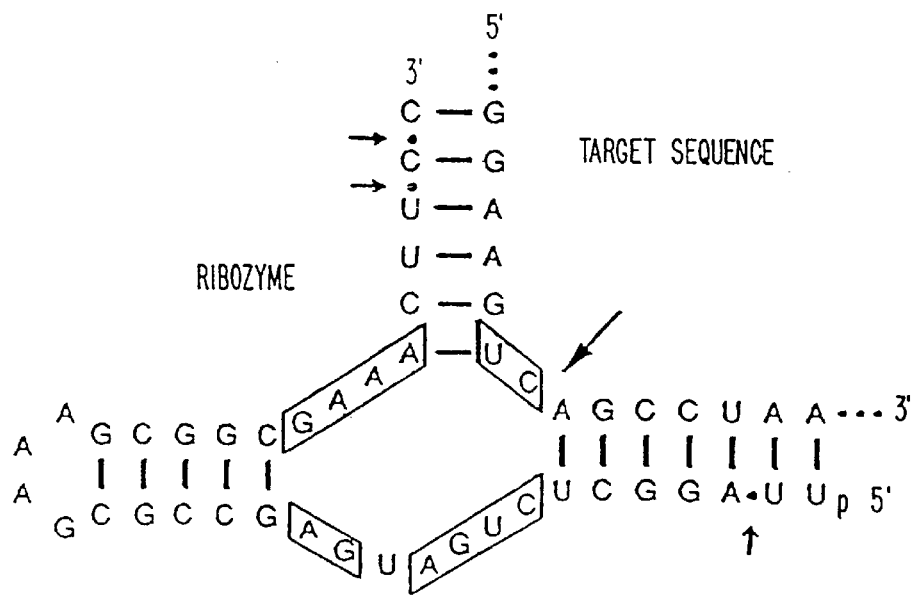
Figure 4C:
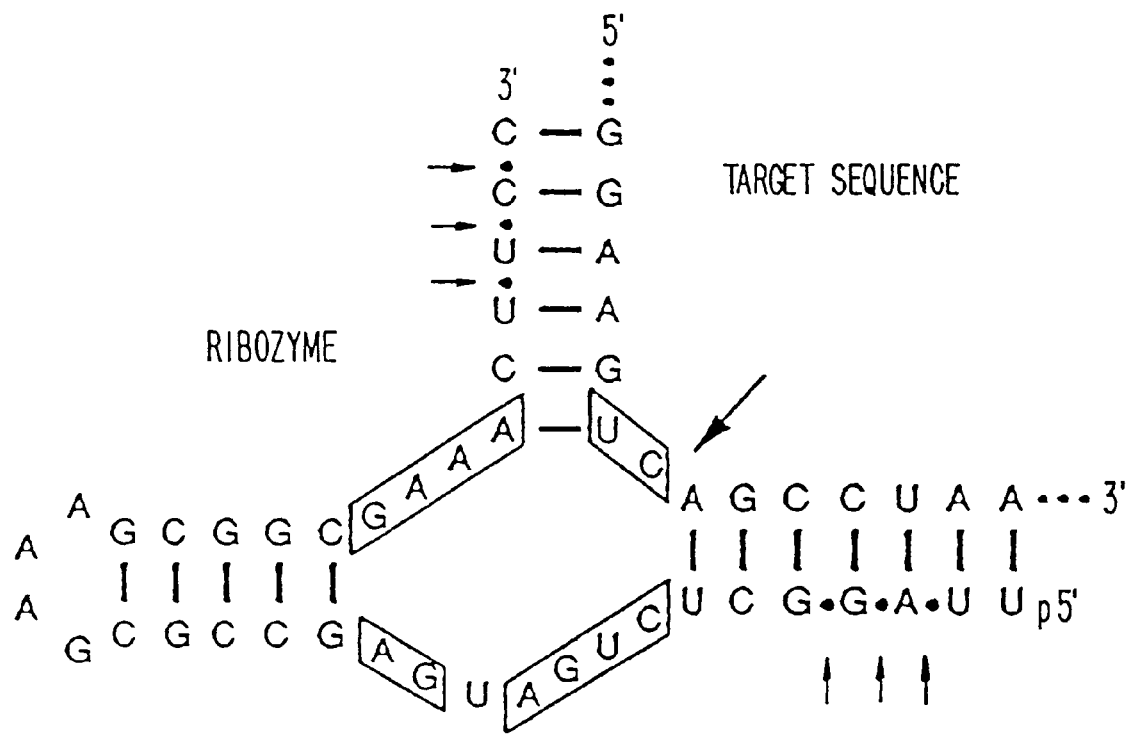
Figure 4D:
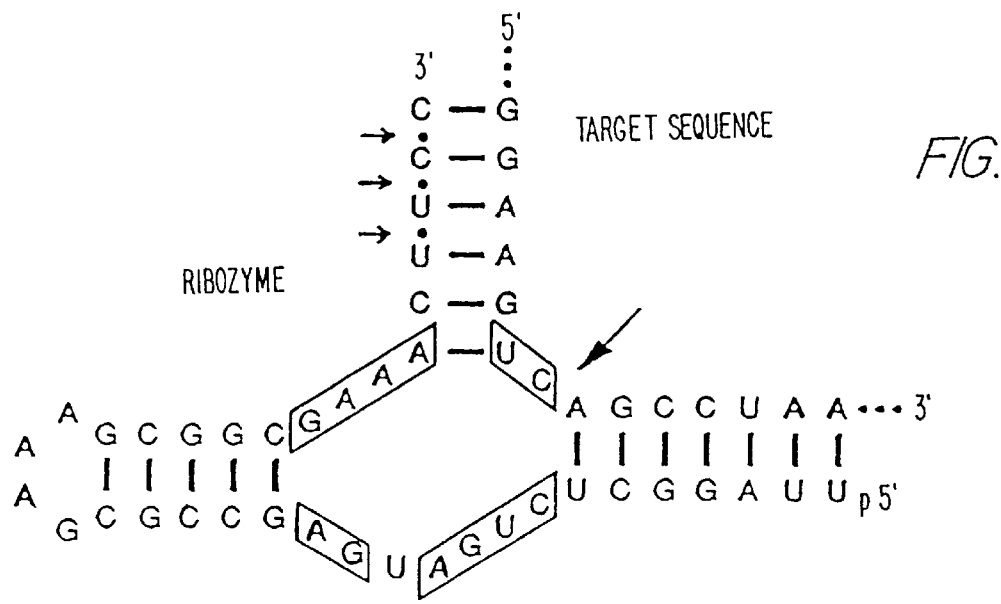
Figure 4E:
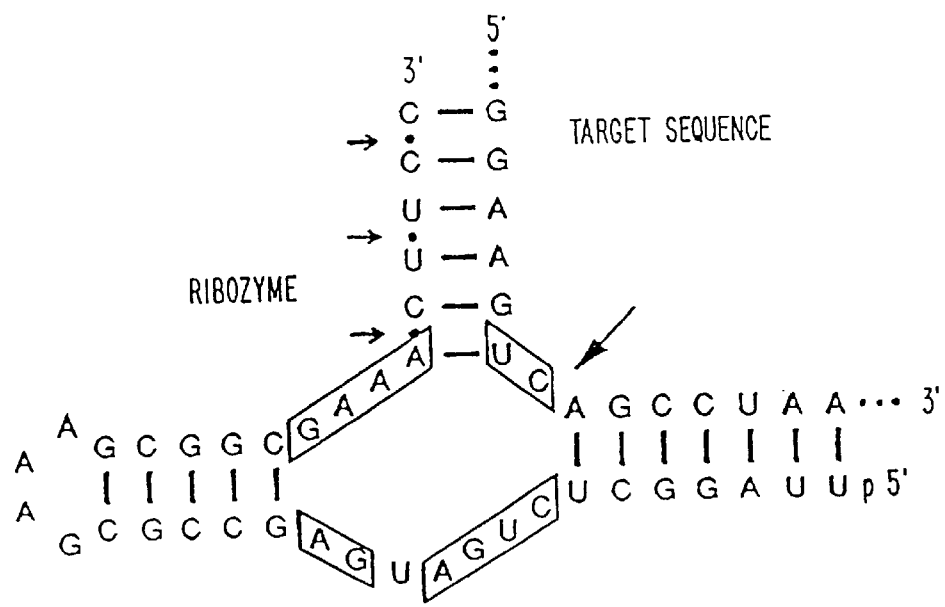
Figure 4F:
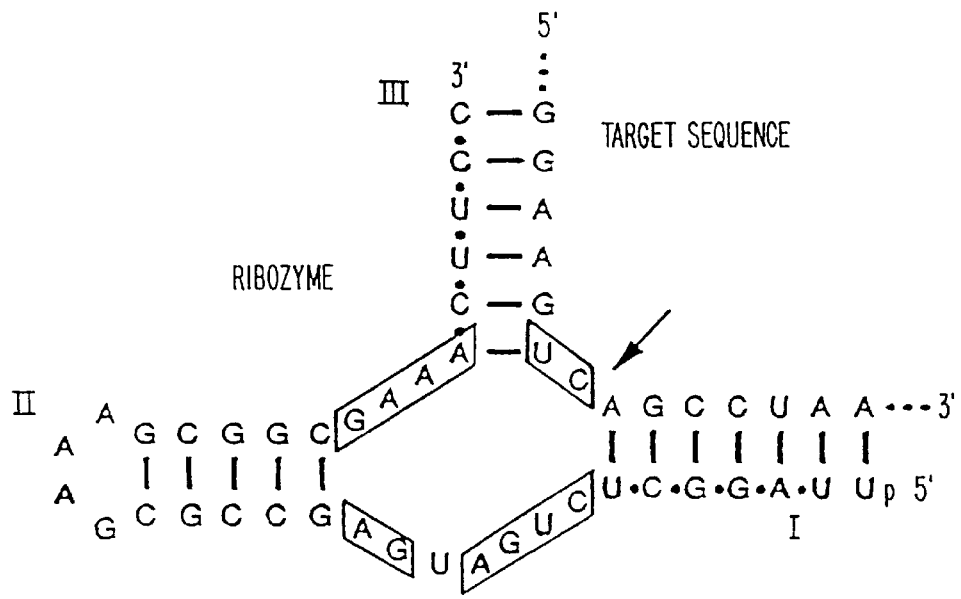
Figure 4G:
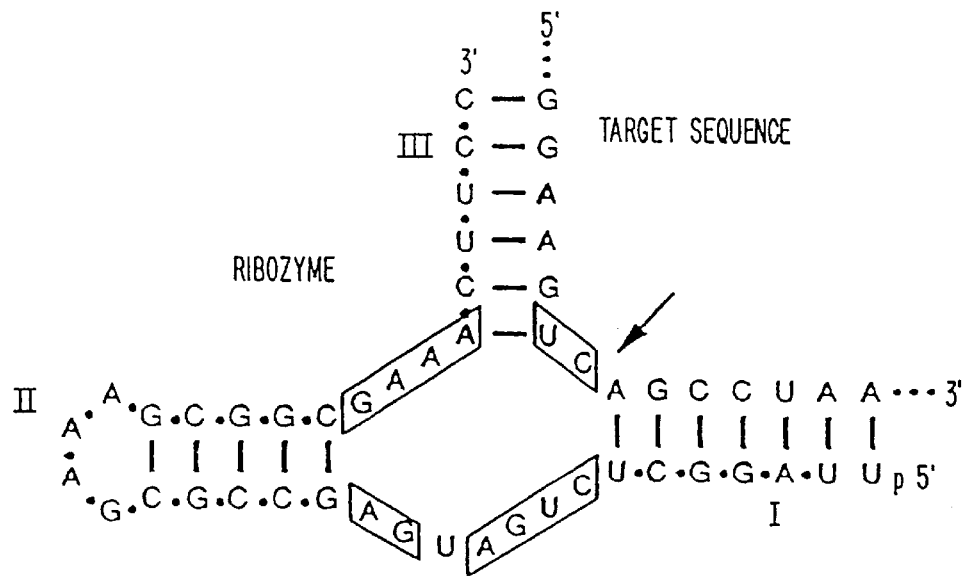

The HIV-1 genomic sequences of the Los Alamos data bank were compared in the regions encoding the vif and nef genes. Fifteen putative ribozyme cleavage sites were found to be highly conserved between the 11 strains of virus sequence. These sites represent the preferable sites for hammerhead ribozyme cleavage within these two target RNAS. Two of the nef gene sites overlap regions within the 3'-LTR of the HIV-1 genome, which represents another target of potential therapeutic value. All of the nef targets are present in all known HIV-1 mRNAs and may represent targets for cleavage which would disrupt 3' terminal control regions of the mRNA which may be required for efficient translation or export of the RNAs. In a similar manner, a number of the vif target sites are present in the pol, tat and vpr mRNAs (see FIG. 2).

Short RNA substrates corresponding to each of the vif and nef gene sites were designed. Each substrate was composed of two to three nucleotides at the 5' and 3' ends that would not base pair with a corresponding ribozyme recognition region. The unpaired regions flanked a central region of 12–14 nucleotides to which complementary arms in the ribozyme were designed.

The structure of each substrate sequence was predicted using a standard commercially available PC fold computer program. Sequences which gave a positive free energy of binding were accepted. Sequences which gave a negative free energy were modified by trimming one or two bases from each of the ends. If the modified sequences were still predicted to have a strong secondary structure, they were rejected.

After substrates were chosen, ribozymes were designed to each of the RNA substrates. Ribozyme folding was also analyzed using PC fold.

Figure 1:
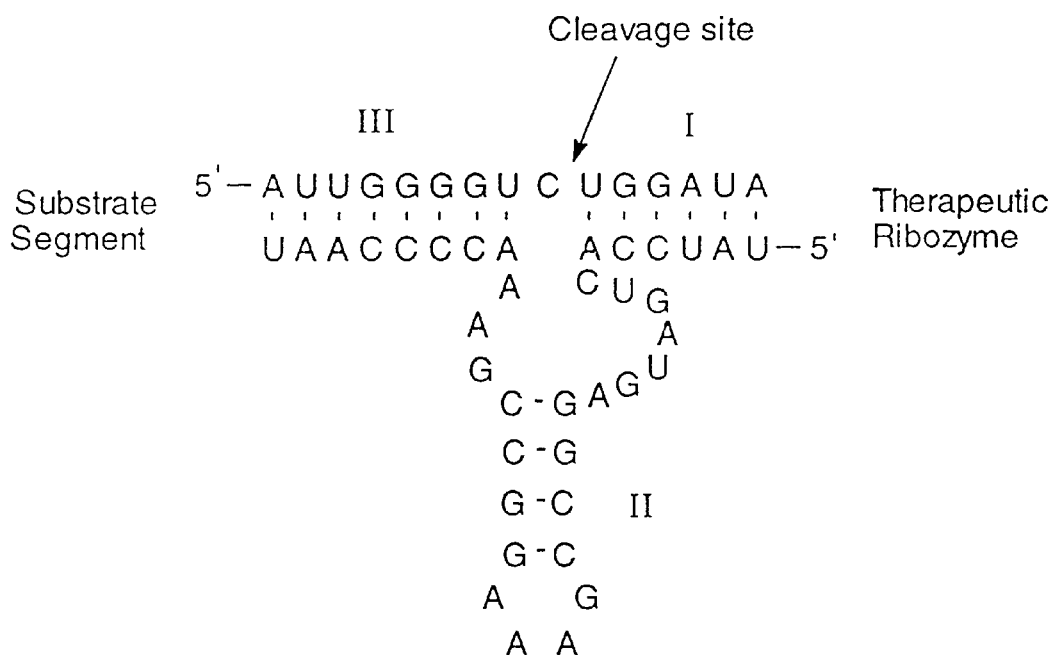

Ribozyme molecules were sought which formed hammerhead motif stem II (see FIG. 1) regions and contained flanking arms which were devoid of intramolecular base pairing. Often the ribozymes were modified by trimming a base from the ends of the ribozyme, or by introducing additional base pairs in stem II to achieve the desired fold. Ribozymes with incorrect folding were rejected. After substrate/ribozyme pairs were found to contain correct intramolecular structures, the molecules were folded together to predict intermolecular interactions. A schematic representation of a ribozyme with its coordinate base pairing to its cognate target sequence is shown in FIG. 1.

Using such analyses, the following predictions of effective target sites in the vif and nef genes of the HIV genome, based upon computer generated sequence comparisons, were obtained (see Table 1). The target sequence is listed first with the 5'-most nucleotide number, for reference. Bases in parentheses are alternative bases in the conserved patterns.

enhance shelf-life, half-life in vitro, stability, and ease of introduction of such ribozymes to the target site, e.g., to enhance penetration of cellular membranes, and confer the ability to recognize and bind to targeted cells.

TABLE 1

| Base numbers | RNA Target sequence | |
|---|---|---|
| nef gene | | |
| 8–23 | CAAGUGGU C AAAANG | |
| 93–107 | GGAGCAGU A UCUCGA | |
| | (A) | |
| 214–229 | CCNCAGGU A CCUUUA | |
| 283–297 | GGGGGACU G GAAGGG | (ALSO 3'LTR TARGET) |
| | (U) | |
| 430–444 | AAGCUAGU A CCAGUU | (ALSO 3'LTR TARGET) |
| vif gene | | |
| 67–81 | AGUUUAGU A AAACAC | |
| 80–95 | CCAUAUGU A UAUUUC | |
| | (G) | |
| 157–171 | UCAGAAGU A CACAUC | |
| 187–201 | AGAUUGGU A GUAANA | |
| | (C) (A) | |
| 205–220 | AUUGGGGU C UGCAUA | |
| 239–253 | AUCUGGGU C AGGGAG | |
| | (U) | |
| 247–261 | CAGGGAGU C UCCAUA | |
| 286–300 | ACACAAGU A GACCCU | |
| 418–432 | AACAAGGU A GGAUCU | |

Those targets thought to be useful as ribozyme targets can be tested to determine accessibility to nucleic acid probes in a ribonuciease H assay (see below) This assay provides a quick test of the use of the target site without requiring synthesis of a ribozyme. It can be used to screen for sites most suited for ribozyme attack.

Synthesis of Ribozymes

Ribozymes useful in this invention can be produced by gene transcription as described by Cech, supra, or by chemical synthesis. Chemical synthesis of RNA is similar to that for DNA synthesis. The additional 2'-OH group in RNA, however, requires a different protecting group strategy to deal with selective 3'-5' internucleotide bond formation, and with RNA susceptibility to degradation in the presence of bases. The recently developed method of RNA synthesis utilizing the t-butyldimethylsilyl group for the protection of the 2' hydroxyl is the most reliable method for synthesis of ribozymes. The method reproducibly yields RNA with the correct 3'-5' internucleotide linkages, with average coupling yields in excess of 99%, and requires only a two-step deprotection of the polymer.

A method, based upon H-phosphonate chemistry exhibits a relatively lower coupling efficiency than a method based upon phosphoramidite chemistry. This is a problem for synthesis of DNA as well. A promising approach to scale-up of automatic oligonucleotide synthesis has been described recently for the H-phosphonates. A combination of a proper coupling time and additional capping of "failure" sequences gave high yields in the synthesis of oligodeoxynucleotides in scales in the range of 14 μmoles with as little as 2 equivalents of a monomer in the coupling step. Another alternative approach is to use soluble polymeric supports (e.g., polyethylene glycols), instead of the conventional solid supports. This method can yield short oligonucleotides in hundred milligram quantities per batch utilizing about 3 equivalents of a monomer in a coupling step.

Various modifications to ribozyme structure can be made to enhance the utility of ribozymes. Such modifications will Exogenous delivery of ribozymes benefits from chemical modification of the backbone, e.g., by the overall negative charge of the ribozyme molecule being reduced to facilitate diffusion across the cell membrane. The present strategies for reducing the oligonucleotide charge include: modification of internucleotide linkages by methylphosphonates, use of phosphoramidites, linking oligonucleotides to positively charged molecules, and creating complex packages composed of oligonucleotides, lipids and specific receptors or effectors for targeted cells. Examples of such modifications include sulfur-containing ribozymes containing phosphorothioates and phosphorodithioates as internucleotide linkages in RNA. Synthesis of such sulfur-modified ribozymes is achieved by use of the sulfur-transfer reagent, $^3$H-1,2-benzenedithiol-3-one 1,1-dioxide. Ribozymes may also contain ribose modified ribonucleotides. Pyrimidine analogues are prepared from uridine using a procedure employing diethylamino sulphur trifluoride (DAST) as a starting reagent. Ribozymes can also be either electrostatically or covalently attached to polymeric cations for the purpose of reducing charge. The polymer can be attached to the ribozyme by simply converting the 3'-end to a ribonucleoside dialdehyde which is obtained by a periodate cleavage of the terminal 2', 3'-cis diol system. Depending on the specific requirements for delivery systems, other possible modifications may include different linker arms. containing carboxyl, amino or thiol functionalities. Yet further examples include use of methylphosphonates and 2'-O-methylribose and 5' or 3' capping or blocking with $m_7$GpppG or $m_3^{2,2,7}$GpppG.

For example, a kinased ribozyme is contacted with guanosine triphosphate and guanyltransferase to add a $m^3$G cap to the ribozyme. After such synthesis, the ribozyme can be gel purified using standard procedure. To ensure that the ribozyme has the desired activity, it may be tested with and without the 5' cap using standard procedures to assay both its enzymatic activity and its stability.

Synthetic ribozymes, including those containing various modifiers, can be purified by high pressure liquid chromatography (HPLC). Other liquid chromatography techniques, employing reverse phase columns and anion exchangers on silica and polymeric supports may also be used.

There follows an example of the synthesis of one ribozyme. A solid phase phosphoramidite chemistry was employed. Monomers used were 2'-tert-butyl-dimethylsilyl cyanoethylphosphoramidites of uridine, N-benzoyl-cytosine, N-phenoxyacetyl adenosine, and guanosine (Glen Research, Sterling, Va.).

Solid phase synthesis was carried out on either an ABI 394 or 380B DNA/RNA synthesizer using the standard protocol provided with each machine. The only exception was that the coupling step was increased from 10 to 12 minutes. The phosphoramidite concentration was 0.1 M. Synthesis was done on a 1 μmole scale using a 1 μmole RNA reaction column (Glen Research). The average coupling efficiencies were between 97% and 98% for the 394 model, and between 97% and 99% for the 380B model, as determined by a calorimetric measurement of the released trityl cation.

After synthesis, the blocked ribozymes were cleaved from the solid support (e.g., CPG), and the bases and diphospho-ester moiety deprotected in a sterile vial by incubation in dry ethanolic ammonia (2 mL) at 55° C. for 16 hours. The reaction mixture was cooled on dry ice. Later, the cold liquid was transferred into a sterile screw cap vial and lyophilized.

To remove the 2'-tert-butyl-dimethylsilyl groups from the ribozyme, the obtained residue was suspended in 1 M tetra-n-butylammonium fluoride in dry THF (TBAF), using a 20-fold excess of the reagent for every silyl group, for 16 hours at ambient temperature (about 15–25° C.). The reaction was quenched by adding an equal volume of sterile 1 M triethylamine acetate, pH 6.5. The sample was cooled and concentrated on a SpeedVac to half the initial volume.

The ribozymes were purified in two steps by HPLC on a C4 300 Å 5 μm DeltaPak column in an acetonitrile gradient.

The first step, or "trityl on" step, was a separation of 5'-DMT-protected ribozyme(s) from failure sequences lacking a 5'-DMT group. Solvents used for this step were: A (0.1 M Triethylammonium acetate, pH 6.8) and B (acetonitrile). The elution profile was: 20% B for 10 minutes, followed by a linear gradient of 20% B to 50% B over 50 minutes, 50% B for 10 minutes, a linear gradient of 50% B to 100% B over 10 minutes, and a linear gradient of 100% B to 0% B over 10 minutes.

The second step was a purification of a completely deblocked ribozyme by a treatment of 2% trifluoroacetic acid on a C4 300 Å 5 μm DeltaPak column in an acetonitrile gradient. Solvents used for this second step were: A (0.1 M Triethylammonium acetate, pH 6.8) and B (80% acetonitrile, 0.1 M triethylammonium acetate, pH 6.8). The elution profile was: 5% B for 5 minutes, a linear gradient of 5% B to 15% B over 60 minutes, 15% B for 10 minutes, and a linear gradient of 15% B to 0% B over 10 minutes.

The fraction containing ribozyme, which is in the triethylammonium salt form, was cooled and lyophilized on a SpeedVac. Solid residue was dissolved in a minimum amount of ethanol and ribozyme in sodium salt form was precipitated by addition of sodium perchlorate in acetone. ($K^+$ or $Mg^{2+}$ salts can be produced in an equivalent manner.) The ribozyme was collected by centrifugation, washed three times with acetone, and lyophilized.

Expression Vector

While synthetic ribozymes are preferred in this invention, those produced by expression vectors can also be used. In designing a suitable ribozyme expression vector the following factors are important to consider. The final ribozyme must be kept as small as possible to minimize unwanted secondary structure within the ribozyme. A promoter (e.g., the human cytomegalovirus immediate early region (HCMV ie1) promoter) should be chosen to be a relatively strong promoter, and expressible both in vitro and in vivo. Such a promoter should express the ribozyme at a level suitable to effect production of enough ribozyme to destroy a target RNA, but not at too high a level to prevent other cellular activities from occurring (unless cell death itself is desired).

A hairpin at the 5' end of the ribozyme is useful to ensure that the required transcription initiation sequence (GG or GGG or GGGAG) does not bind to some other part of the ribozyme and thus affect regulation of the transcription process. The 5' hairpin is also useful to protect the ribozyme from 5'-3' exonucleases. A selected hairpin at the 3' end of the ribozyme gene is useful since it acts as a transcription termination signal, and as a protection from 3'-5' exonuclease activity. One example of a known termination signal is that present on the T7 RNA polymerase system. This signal is about 30 nucleotides in length. Other 3' hairpins of shorter length can be used to provide good termination and RNA stability. Such hairpins can be inserted within the vector sequences to allow standard ribozymes to be placed in an appropriate orientation and expressed with such sequences attached.

Poly(A) tails are also useful to protect the 3' end of the ribozyme. These can be provided by either including a poly(A) signal site in the expression vector (to signal a cell to add the poly(A) tail in vivo), or by introducing a poly(A) sequence directly into the expression vector. In the first approach, the signal must be located to prevent unwanted secondary structure formation with other parts of the ribozyme. In the second approach, the poly(A) stretch may reduce in size over time when expressed in vivo, and thus the vector may need to be checked over time. Care must be taken in addition of a poly(A) tail which binds poly(A) binding proteins which prevent the ribozyme from acting upon their target sequence.

Ribozyme Testing

Once the desired ribozymes are selected, synthesized and purified, they are tested in kinetic and other experiments to determine their utility. An example of such a procedure is provided below.

Preparation of Ribozyme

Crude synthetic ribozyme (typically 350 μg at a time) is purified by separation on a 15% denaturing polyacrylamide gel (0.75 mm thick, 40 cm long) and visualized by UV shadowing. Once excised, gel slices containing full length ribozyme are soaked in 5 ml gel elution buffer (0.5 M $NH_4OAc$, 1 mM EDTA) overnight with shaking at 4° C. The eluent is desalted over a C-18 matrix (Sep-Pak cartridges, Millipore, Milford, Mass.) and vacuum dried. The dried RNA is resuspended in 50–100 μl TE (TRIS 10 mM, EDTA 1 mM, pH 7.2). An aliquot of this solution is diluted 100-fold into 1 ml TE, half of which is used to spectrophotometrically quantitate the ribozyme solution. The concentration of this dilute stock is typically 150–800 nM. Purity of the ribozyme is confirmed by the presence of a single band on a denaturing polyacrylamide gel.

A ribozyme may advantageously be synthesized in two or more portions. Each portion of a ribozyme will generally have only limited or no enzymatic activity, and the activity will increase substantially (by at least 5–10 fold) when all portions are ligated (or otherwise juxtaposed) together. A specific example of hammerhead ribozyme synthesis is provided below.

The method involves synthesis of two (or more) shorter "half" ribozymes and ligation of them together using T4 RNA ligase. For example, to make a 34 mer ribozyme, two 17 mers are synthesized, one is phosphorylated, and both are gel purified. These purified 17 mers are then annealed to a DNA splint strand complementary to the two 17 mers. This DNA splint has a sequence designed to locate the two 17 mer portions with one end of each adjacent each other. The juxtaposed RNA molecules are then treated with T4 RNA ligase in the presence of ATP. Alternatively, the DNA splint strand may be omitted from the ligation reaction if the complementary binding affects favorable ligation of the two RNA molecules. The 34 mer RNA so formed is then HPLC purified.

Preparation of Substrates

Approximately 10–30 pmoles of unpurified substrate is radioactively 5' end-labeled with T4 polynucleotide kinase using 25 pmoles of [$\gamma$-$^{32}$P] ATP. The entire labeling mix is separated on a 20% denaturing polyacrylamide gel and visualized by autoradiography. The full length band is excised and soaked overnight at 4° C. in 100 $\mu$l of TE (10 mM Tris-HCl pH 7.6, 0.1 mM EDTA).

Kinetic Reactions

For reactions using short substrates (between 8 and 16 bases) a substrate solution is made 1× in assay buffer (75 mM Tris-HCl, pH 7.6; 0.1 mM EDTA, 10 mM MgCl$_2$) such that the concentration of substrate is less than 1 nM. A ribozyme solution (typically 20 nM) is made 1× in assay buffer and four dilutions are made using 1× assay buffer. Fifteen $\mu$l of each ribozyme dilution (i.e., 20, 16, 12, 8 and 4 nM) is placed in a separate tube. These tubes and the substrate tube are pre-incubated at 37° C. for at least five minutes.

The reaction is started by mixing 15 $\mu$l of substrate into each ribozyme tube by rapid pipetting (note that final ribozyme concentrations are 10, 8, 6, 4, 2 nM). Five $\mu$l aliquots are removed at 15 or 30 second intervals and quenched with 5 $\mu$l stop solution (95% formamide, 20 mM EDTA xylene cyanol, and bromphenol blue dyes). Following the final ribozyme time point, an aliquot of the remaining substrate is removed as a zero ribozyme control.

The samples are separated on either 15% or 20% polyacrylamide gels. Each gel is visualized and quantitated with an Ambis beta scanner (Ambis Systems, San Diego, Calif.).

For the most active ribozymes, kinetic analyses are performed in substrate excess to determine $K_m$ and $K_{cat}$ values.

For kinetic reactions with long RNA substrates (greater than 15 bases in length) the substrates are prepared by transcription using T7 RNA polymerase and defined templates containing a T7 promoter, and DNA encoding appropriate nucleotides of the HIV-1 RNA. The substrate solution is made 1× in assay buffer (75 mM Tris-HCl, pH 7.6; 0.1 mM EDTA; 10 mM MgCl$_2$) and contains 58 nanomolar concentration of the long RNA molecules. The reaction is started by addition of gel purified ribozymes to 1 $\mu$M concentration. Aliquots are removed at 20, 40, 60, 80 and 100 minutes, then quenched by the addition of 5 $\mu$l stop solution. Cleavage products are separated using denaturing PAGE. The bands are visualized and quantitated with an Ambis beta scanner.

Kinetic Analysis

A simple reaction mechanism for ribozyme-mediated cleavage is:

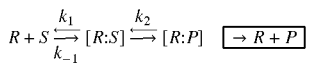

where R=ribozyme, S=substrate, and P=products. The boxed step is important only in substrate excess. Because ribozyme concentration is in excess over substrate concentration, the concentration of the ribozyme-substrate complex ([R:S]) is constant over time except during the very brief time when the complex is being initially formed, i.e.,:

$$\frac{d[R:S]}{dt} = 0$$

where t=time, and thus:

$$(R)(S)k_1 = (RS)(k_2 + k_{-1}).$$

The rate of the reaction is the rate of disappearance of substrate with time:

$$\text{Rate} = \frac{-d(S)}{dt} = k_2(RS)$$

Substituting these expressions:

$$(R)(S)k_1 = 1/k_2 \frac{-d(S)}{dt}(k_2 + k_1)$$

or:

$$\frac{-d(S)}{S} = \frac{k_1 k_2}{(k_2 + k_1)}(R)dt$$

Integrating this expression with respect to time yields:

$$-\ln\frac{S}{S_0} = \frac{k_1 k_2}{(k_2 + k_1)}(R)t$$

where $S_0$=initial substrate. Therefore, a plot of the negative log of fraction substrate uncut versus time (in minutes) yields a straight line with slope:

$$\text{slope} = \frac{k_1 k_2}{(k_2 + k_1)}(R) = k_{obs}$$

where $k_{obs}$=observed rate constant. A plot of slope ($k_{obs}$) versus ribozyme concentration yields a straight line with a slope which is:

$$\text{slope} = \frac{k_1 k_2}{(k_2 + k_1)} \quad \text{which is} \quad \frac{k_{cat}}{K_m}$$

Using these equations the data obtained from the kinetic experiments provides the necessary information to determine which ribozyme tested is most useful, or active. Such ribozymes can be selected and tested in in vivo or ex vivo systems.

Liposome Preparation

Lipid molecules were dissolved in a volatile organic solvent (CHCl$_3$, methanol, diethylether, ethanol, etc.). The organic solvent was removed by evaporation. The lipid was hydrated into suspension with 0.1× phosphate buffered saline (PBS), then freeze-thawed 3× using liquid nitrogen and incubation at room temperature. The suspension was extruded sequentially through a 0.4 μm, 0.2 μm and 0.1 μm polycarbonate filters at maximum pressure of 800 psi. The ribozyme was mixed with the extruded liposome suspension and lyophilized to dryness. The lipid/ribozyme powder was rehydrated with water to one-tenth the original volume. The suspension was diluted to the minimum volume required for extrusion (0.4 ml for 1.5 ml barrel and 1.5 ml for 10 ml barrel) with 1×PBS and re-extruded through 0.4 μm, 0.2 μm, 0.1 μm polycarbonate filters. The liposome entrapped ribozyme was separated from untrapped ribozyme by gel filtration chromatography (SEPHAROSE CL-4B, BIOGEL A5M). The liposome extractions were pooled and sterilized by filtration through a 0.2 μm filter. The free ribozyme was pooled and recovered by ethanol precipitation. The liposome concentration was determined by incorporation of a radioactive lipid. The ribozyme concentration was determined by labeling with $^{32}$. Rossi et al., 1992, supra (and references cited therein), describe other methods suitable for preparation of liposomes.

In experiments with a liposome formulation composed of a synthetic lipid derivative disteraoyl-phosphatidylethylamidothioacetyl succinimide (DSPE-ATS) co-formulated with dipalmitoylphosphatidyl choline and cholesterol we observed uptake of 100 and 200 nm diameter liposomes with similar kinetics. The larger particles accommodated a larger number of entrapped molecules, or larger molecular weight molecules, such as an expression plasmid. These particles showed a linear relationship between the lipid dose offered and the mean log fluorescence (calcein was used to follow liposome uptake). No cytotoxicity was observed even with a 200 μM dose. These liposomes are particularly useful for delivery to CD4 cell populations.

In Vivo Assay

The efficacy of action of a chosen ribozyme may be tested in vivo by use of cell cultures sensitive to HIV-1 or a related virus, using standard procedures. For example, monolayer cultures of HIV-sensitive cells are grown by established procedures. Cells are grown in 6 or 96 well tissue culture plates. Prior to infection with HIV, cultures are treated for 3 to 24 hours with ribozyme-containing liposomes. Cells are then rinsed with phosphate buffered saline (PBS) and virus added at a multiplicity of 1–100 pfu/cell. After a one-hour adsorption, free virus is rinsed away using PBS, and the cells are treated for three to five days with appropriate liposome preparations. Cells are then re-fed with fresh medium and re-incubated. Virus is harvested from cells into the overlying medium. Cells are broken by three cycles of incubation at −70° C. and 37° C. for 30 minutes at each temperature, and viral titers determined by plaque assay using established procedures.

Ribonuclease Protection Assay

The accumulation of target mRNA in cells or the cleavage of the RNA by ribozymes or RNaseH (in vitro or in vivo) can be quantified using an RNase protection assay.

In this method, antisense riboprobes are transcribed from template DNA using T7 RNA polymerase (U.S. Biochemical) in 20 μl reactions containing 1× transcription buffer (supplied by the manufacturer), 0.2 mM ATP, GTP and UTP, 1 U/μl pancreatic RNase inhibitor (Boehringer Mannheim Biochemicals) and 200 μCi $^{32}$P-labeled CTP (800 Ci/mmol, New England Nuclear) for 1 hour at 37° C. Template DNA is digested with 1 U RNase-free DNaseI (U.S. Biochemical, Cleveland, Ohio) at 37° C. for 15 minutes and unincorporated nucleotides removed by G-50 SEPHADEX spin chromatography.

In a manner similar to the transcription of antisense probe, the target RNA can be transcribed in vitro using a suitable DNA template. The transcript is purified by standard methods and digested with ribozyme at 37° C. according to methods described later.

Alternatively, virus-infected cells are harvested into 1 ml of PBS, transferred to a 1.5 ml EPPENDORF tube, pelleted for 30 seconds at low speed in a microcentrifuge, and lysed in 70 μl of hybridization buffer (4 M guanidine isothiocyanate, 0.1% sarcosyl, 25 mM sodium citrate, pH 7.5). Cell lysate (45 μl) or defined amounts of in vitro transcript (also in hybridization buffer) is then combined with 5 μl of hybridization buffer containing 5×10$^5$ cpm of each antisense riboprobe in 0.5 ml Eppendorf tubes, overlaid with 25 Ml mineral oil, and hybridization accomplished by heating overnight at 55° C. The hybridization reactions are diluted into 0.5 ml RNase solution (20 U/ml RNaseA, 2 U/ml RNaseT1, 10 U/ml RNase-free DNaseI in 0.4 M NaCl), heated for 30 minutes at 37° C., and 10 μl of 20% SDS and 10 μl of Proteinase K (10 mg/ml) added, followed by an additional 30 minutes incubation at 37° C. Hybrids are partially purified by extraction with 0.5 ml of a 1:1 mixture of phenol/chloroform; aqueous phases are combined with 0.5 ml isopropanol, and RNase-resistant hybrids pelleted for 10 minutes at room temperature (about 20° C.) in a microcentrifuge. Pellets are dissolved in 10 μl loading buffer (95% formamide, 1×TBE, 0.1% bromophenol blue, 0.1% xylene cylanol), heated to 95° C. for five minutes, cooled on ice, and analyzed on 4% polyacrylamide/7 M urea gels under denaturing conditions.

Ribozyme Stability

The chosen ribozyme can be tested to determine its stability, and thus its potential utility. Such a test can also be used to determine the effect of various chemical modifications (e.g., addition of a poly(A) tail) on the ribozyme stability and thus aid selection of a more stable ribozyme. For example, a reaction mixture contains 1 to 5 pmoles of 5' (kinased) and/or 3' labeled ribozyme, 15 μg of cytosolic extract and 2.5 mM MgCl$_2$ in a total volume of 100 Ml. The reaction is incubated at 37° C. Eight μl aliquots are taken at timed intervals and mixed with 8 μl of a stop mix (20 mM EDTA, 95% formamide). Samples are separated on a 15% acrylamide sequencing gel, exposed to film, and scanned with an Ambis.

A 3'-labeled ribozyme can be formed by incorporation of the $^{32}$P-labeled cordycepin at the 3' OH using poly(A) polymerase. For example, the poly(A) polymerase reaction contains 40 mM Tris, pH 8, 10 mM MgCl$_2$, 250 mM NaCl, 2.5 mM MnCl$_2$; 3 μl P$^{32}$ cordycepin, 500 Ci/mM; and 6 units poly(A) polymerase in a total volume of 50 μl. The reaction mixture is incubated for 30 minutes at 37° C.

Effect of Liposome Surface Modifications on Lymphocyte and MacroPhage Uptake

Liposomes containing distearoylphosphatidyl ethanolamidomethyl thioacetate can be prepared. The thiol group can be deprotected using hydroxylamine and the reactive thiol can then be modified with thiol reactive groups to alter the surface properties of the liposomes. Reaction with N-ethylmaleimide leads to lymphocyte and macrophage uptake. This modification results in liposome uptake by CD4$^-$ and CD4$^+$ lymphocytes.

Modification with iodoacetamide and iodoacetic acid were tested for uptake. Iodactamide modification showed that the liposomes were toxic in that the lymphocyte cell number decreased with time. However, the acetate uptake was 5-fold greater than that observed for succinimide. Uptake was monitored-by both uptake of a $^3$H-hexadecylcholesterol ether and an entrapped water soluble fluorophore, calcein. Both confirmed that the liposomes were being taken up by the cells over a 72 hour period. The uptake was assayed in lymphoblasts which had been stimulated for 72 hours with phytohemagglutinin. The uptake curve was biphasic in that within the first 8 hours, only cell surface binding was observed whereas after 24 hours, uptake was linear for up to 72 hours. This was observed for a 200 μM dose. The 100 μM lipid dose showed only cell surface binding.

Effect of Base Substitution Upon Ribozyme Activity

To determine which primary structural characteristics could change ribozyme cleavage of substrate, minor base changes can be made in the substrate cleavage region recognized by a specific ribozyme. For example, the substrate sequences can be changed at the central "C" nucleotide, changing the cleavage site from a GUC to a GUA motif. The $K_{cat}/K_m$ values for cleavage using each substrate are then analyzed to determine if such a change increases ribozyme cleavage rates. Similar experiments can be performed to address the effects of changing bases complementary to the ribozyme binding arms. Changes predicted to maintain strong binding to the complementary substrate are preferred. Minor changes in nucleotide content can alter ribozyme/substrate interactions in ways which are unpredictable based upon binding strength alone. Structures in the catalytic core region of the ribozyme recognize trivial changes in either substrate structure or the three dimensional structure of the ribozyme/substrate complex.

To begin optimizing ribozyme design, the cleavage rates of ribozymes containing varied arm lengths, but targeted to the same length of short RNA substrate can be tested. Minimal arm lengths are required and effective cleavage varies with ribozyme/substrate combinations.

The cleavage activity of selected ribozymes can be assessed using HIV-1-homologous substrates. The assays are performed in ribozyme excess and approximate $K_{cat}/K_{min}$ values obtained. Comparison of values obtained with short and long substrates indicates utility in vivo of *a ribozyme.

Intracellular Stability of Liposome-delivered Ribozymes

To test the stability of a chosen ribozyme in vivo the following test is useful. Ribozymes are $^{32}$P-end-labeled, entrapped in liposomes and delivered to HIV-1 sensitive cells for three hours. The cells are fractionated and ribozyme is purified by phenol/chloroform extraction. Alternatively, cells (1×10$^7$, T-175 flask) are scraped from the surface of the flask and washed twice with cold PBS. The cells are homogenized by douncing 35 times in 4 ml of TSE (10 mM Tris, pH 7.4, 0.25 M Sucrose, 1 mM EDTA). Nuclei are pelleted at 100×g for 10 minutes. Subcellular organelles (the membrane fraction) are pelleted at 200,000×g for two hours using an SW60 rotor. The pellet is resuspended in 1 ml of H buffer (0.25 M Sucrose, 50 mM HEPES, pH 7.4). The supernatant contains the cytoplasmic fraction (in approximately 3.7 ml). The nuclear pellet is resuspended in 1 ml of 65% sucrose in TM (50 mM Tris, pH 7.4, 2.5 mM $MgCl_2$) and banded on a sucrose step gradient (1 ml nuclei in 65% sucrose TM, 1 ml 60% sucrose TM, 1 ml 55% sucrose TM, 50% sucrose TM, 300 μl 25% sucrose TM) for one hour at 37,000×g with an SW60 rotor. The nuclear band is harvested and diluted to 10% sucrose with TM buffer. Nuclei are pelleted at 37,000×g using an SW60 rotor for 15 minutes and the pellet resuspended in 1 ml of TM buffer. Aliquots are size fractionated on denaturing polyacrylamide gels and the intracellular localization determined. By comparison to the migration rate of newly synthesized ribozyme, the various fraction containing intact ribozyme can be determined.

To investigate modifications which would lengthen the half-life of ribozyme molecules intracellularly, the cells may be fractioned as above and the purity of each fraction assessed by assaying enzyme activity known to exist in that fraction.

The various cell fractions are frozen at −70° C. and used to determine relative nuclease resistances of modified ribozyme molecules. Ribozyme molecules may be synthesized with 5 phosphorothioate (ps), or 2'-O-methyl (2'-OMe) modifications at each end of the molecule. These molecules and a phosphodiester version of the ribozyme are end-labeled with $^{32}$P and ATP using T4 polynucleotide kinase. Equal concentrations are added to the cell cytoplasmic extracts and aliquots of each taken at 10 minute intervals. The samples are size fractionated by denaturing PAGE and relative rates of nuclease resistance analyzed by scanning the gel with an Ambis β-scanner. The results show whether the ribozymes are digested by the cytoplasmic extract, and which versions are relatively more nuclease resistant. Modified ribozymes generally maintain 80–90% of the catalytic activity of the native ribozyme when short RNA substrates are employed.

Unlabeled, 5' end-labeled or 3' end-labeled ribozymes can be used in the assays. These experiments can also be performed with human cell extracts to verify the observations.

HeLa (CD4$^+$) and Vero cells are used by many investigators to screen antiviral chemicals in pre-clinical trials. Ribozymes and antisense DNAs depend upon their nuclease stability to maintain therapeutic levels in infected cells. To design chemical modifications which increase the nuclease stability of ribozymes, we have prepared nuclear, cytoplasmic and membranous lysates from various cell types and compared the relative specific activity (units of nuclease/mg protein) and cation optima ($Mg^{+2}$-, $Mn^{+2}$-, $Ca^{+2}$- or $Zn^{+2}$-activation) of the nuclease populations within these fractions. Nuclease activities vary significantly among the cell fractions studied (Tables 2 and 3, and FIG. 6; +++ indicates high nuclease activity, ++ and + indicate lower levels, and − indicates no nuclease activity as tested by standard methodology), but the nuclease population present in HeLa cells was dissimilar to that observed in both monocyte and lymphocyte preparations (Table 4, standard units are noted in the table for comparison only and are not reflective of a specific level of nuclease activity).

TABLE 2

RELATIVE ACTIVITY OF CYTOPLASMIC EXTRACTS

| Cell Type | Units/10 ug of protein | Divalent cation Requirement |
|---|---|---|
| Vero | 1 | $Mg^{++}$ |
| HeLa | 5.8 | $Zn^{++}$ |
| Cervical Epithelial | 4.7 | $Zn^{++}$ |
| Monocyte enriched | 12.9 | none |
| T Lymphocytes | 23.5 | none |
| Keratinocytes | 4.8 | $Zn^{++}$ |

TABLE 3

Divalent cation effect on RNA degradative activity in HeLa fractions

| HeLa cell fractions | Divalent cation (1 mM) | | | |
|---|---|---|---|---|
| | $MgCl_2$ | $MnCl_2$ | $CaCl_2$ | $ZnCl_2$ |
| Cytoplasmic | + | + | + | +++ |
| Membrane | +++ | +++ | + | − |
| Nuclear | +++ | ++ | +++ | ++ |

TABLE 4

Divalent cation effect on RNA degradative activity in Vero fraction

| Vero cell fractions | Divalent Cation (1 mM) | | | |
|---|---|---|---|---|
| | $MgCl_2$ | $MnCl_2$ | $CaCl_2$ | $ZnCl_2$ |
| Cytoplasmic | +++ | +++ | − | − |
| Membrane | +++ | +++ | − | − |
| Nuclear | +++ | +++ | ++ | − |

HeLa nucleases were maximally active in the presence of added $Zn^{+2}$, while added cation did not enhance nuclease activities in monocyte and lymphocyte lysates. The relative nuclease levels in the monocyte and lymphocyte lysates were 2.2 and 4 times higher, respectively, than in activated HeLa lysates.

Figure 8:
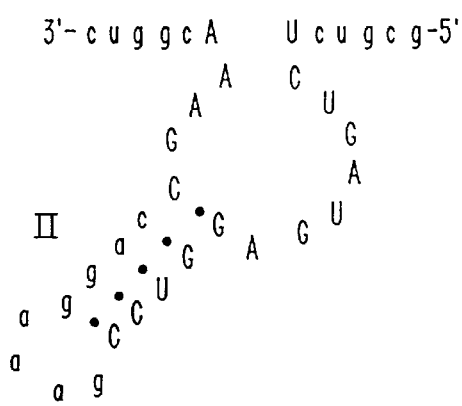

Various chemical modifications to ribozymes were tested for their ability to increase nuclease activity while maintaining catalytic activity of the ribozyme. FIG. 7 shows the effects of various modifications upon the catalytic activity of a selected ribozyme. The modifications which decreased activity (1315, 1371, and 1285) were dropped from further analyses. Chemical modifications to ribozymes resulted in cell-specific patterns of ribozyme stability, and 2'-O-methyl sugar substitution gave the best overall enhancement of ribozyme stability across lysates. Relative resistance of ribozymes to digestion by lymphocyte and monocyte cytoplasmic lysates are shown in FIG. 8. The digestion rates of the ribozymes are similar when the ribozymes are labeled at either the 5'- or 3'-ends of the molecule, demonstrating that the degradation is not due to endogenous phosphatase activity in the lysates.

Figure 9:
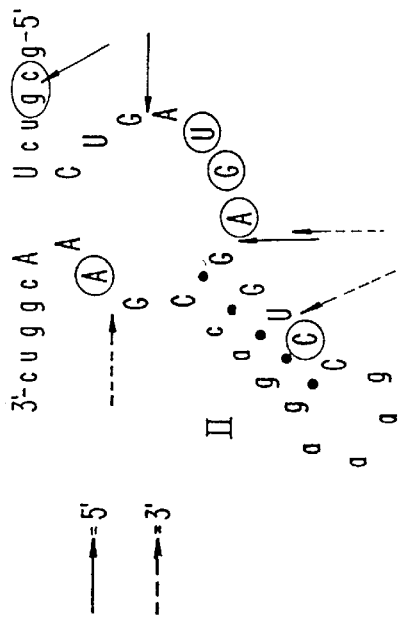

Various reports have suggested that modifications to hammerhead motif ribozymes in the binding arms (stems I and III) will give much enhanced protection from nuclease digestion. As shown in FIG. 9, we observe different results. There appear to be nuclease resistant sites at the positions 2.4, 2.5, 7, 8, 9, 10.4, and 13. The 2.4, 2.5 and 10.4 position resistance may be specific to the ribozyme tested and more sequences need to be tested before a conclusion can be reached concerning the nuclease sensitivity of these sites, but the positions 7, 8, 9 and 13 are conserved nucleotides in this motif and appear to be sites at which nuclease digestion stops, as demonstrated by the appropriate stable fragments produced in lysate digestion experiments. Interestingly, although there seems to be much more nuclease in the lymphocyte and monocyte lysates, no stable fragments were observed when similar experiments were performed using an activated HeLa cytoplasmic lysate. Observations of ribozyme efficacy in HeLa $CD4^+$ cells should be re-examined in lymphocytes before the therapeutic relevance can be determined.

EXAMPLE 1

HIV tat Ribozymes

The 5' exon of tat contains the following potential cleavage sites: 2 GUC sites, 3 GUA sites, 5 AUC sites, 3 UCC sites, and 5 CUC sites. All 18 sites were examined by computer folding and by RNaseH cleavage assay.

A measure of the accessibility of each site to binding by a 13-mer oligonucleotide was preferred in the following way:

(a) The first 425 nucleotides of the clone V sequence (this clone was made available by Dr. Rossi and includes the 5' tat exon at nucleotides 151–366) was folded on RNAFOLD 4.0 (a generally available program) and examined for the presence of folding domains, i.e., self-contained structures closed by a stem.

(b) For each potential cleavage site, the domain containing that site was folded to confirm that it folded as in part (a); then the domain was refolded while forcing the cleavage site and surrounding nucleotides (11–16 nucleotides in all) to remain unpaired. The difference in these two folding free energies was taken as the cost of melting out that region for base-pairing by a ribozyme or DNA oligonucleotide.

(c) The lengths of DNA oligonucleotides were adjusted to give predicted delta-G (binding) of −17 to −18 kcal/mole. Thus, differences in overall binding energy was predicted to be reflected in the free energy differences calculated in part (b). The calculations are shown in Table 5.

TABLE 5

| Total Start Seq | # | Site | Delta G Melting Structure | Length | Delta G Binding Oligo | Delta G Binding |
|---|---|---|---|---|---|---|
| 194 | GUC | 1 (@200) | +8.6 | 11 | −17.2 | −8.6 |
| 332 | GUC | 2 (@338) | +8.2 | 11 | −17.3 | −9.1 |
| 156 | GUA | 3 (@163) | +7.5 | 12 | −17.7 | −10.2 |
| 211 | GUA | 4 (@218) | +8.0 | 13 | −17.5 | −9.7 |
| 225 | GUA | 5 (@233) | +6.8 | 15 | −16.3 | −9.5 |
| 161 | AUC | 6 (@167) | +5.4 | 13 | −18.0 | −12.6 |
| 186 | AUC | 7 (@192) | +1.6 | 11 | −17.7 | −16.1 |
| 280 | AUC | 8 (@286) | +5.5 | 11 | −17.9 | −12.4 |
| 340 | AUC | 9 (@347) | +7.1 | 13 | −17.0 | −9.9 |
| 352 | AUC | 10 (@360) | +1.7 | 14 | −17.4 | −15.7 |
| 240 | UUC | 11 (@248) | +11.7 | 14 | −17.4 | −5.7 |
| 257 | UUC | 12 (@265) | +10.7 | 16 | −17.4 | −6.7 |
| 346 | UUC | 13 (@354) | +9.7 | 14 | −17.2 | −7.5 |
| 281 | CUC | 14 (@288) | +5.5 | 12 | −17.6 | −12.1 |
| 319 | CUC | 15 (@326) | +11.9 | 11 | −17.1 | −5.2 |
| 322 | CUC | 16 (@329) | +13.8 | 11 | −17.5 | −3.7 |
| 337 | CUC | 17 (@344) | +6.3 | 12 | −17.2 | −10.9 |
| 349 | CUC | 18 (@356) | +10.6 | 14 | −17.2 | −6.6 |

[site refers to nucleotide 5' of cleaved phosphate]

Eighteen DNA oligonucleotides were made to target the 18 target sites listed in Table 5. RNaseH experiments were performed using approximately 100 nM body labeled RNA transcript (clone V), 0.08 U/µl RNaseH (excess RNaseH) and a 2× dilution of 1 mM, 10 µM or 1 µM DNA oligonucleotide. The results are shown in Table 5. Eight out of 18 sites had greater than 40% cleavage at 5 μM after 10 minutes incubation. Three ribozymes were designed against the three most active sequences (H332, H337b, H352, see Table 6).

phoramidite nucleotides used in place of standard nucleotides. Ribozyme activity was determined in the manner described above with PAGE analysis.

TABLE 6

| Oligo Name | Sequence (5'—>3') | Core | Length | Binding | Melting | Net | 1 mM/30* | 10 μM/10* | 1 μM/10* |
|---|---|---|---|---|---|---|---|---|---|
| | | | | | | | ENERGIES | | % CLEAVAGE |
| H156 | GATCTACTGGCT | GUA | 12 | -18.5 | 7.5 | -11 | 83 | 36 | 0 |
| H161 | GTCTAGGATCTAC | AUC | 13 | -18.8 | 5.4 | -13.4 | 12 | 0 | 0 |
| H186 | TCCTGGATGCT | AUC | 11 | -18.3 | 9.4 | -8.9 | 82 | 0 | 0 |
| H194b | GGCTGACTTCC | GUC | 11 | -18.6 | 8.6 | -10 | 99 | 84 | 0 |
| H211v2 | ATTGGTACAAGCA | GUA | 13 | -18 | 8 | -10 | 61 | 21 | 0 |
| H225 | ACTTTTTACAATAGC | GUA | 15 | -17 | 6.8 | -10.2 | 47 | 0 | 0 |
| H240 | GCAATGAAAGCAAC | UUC | 13 | -19.4 | 11.7 | -7.7 | 25 | 0 | 0 |
| H257 | TTGTTATGAAACAAAC | UUC | 16 | -18 | 10.7 | -7.3 | 100 | 0 | 0 |
| H280 | AGGAGATGCCT | AUC | 11 | -18.2 | 5.5 | -12.7 | 96 | 60 | 0 |
| H281 | ATAGGAGATGCC | CUC | 12 | -18.5 | 6.3 | -12.2 | 84 | 11 | 0 |
| H319 | GAGGAGGTCTT | CUC | 11 | -17.4 | 11.9 | -5.5 | 87 | 40 | 0 |
| H322 | CTTGAGGAGGT | CUC | 11 | -16.9 | 13.,8 | -3.1 | 94 | 8 | 0 |
| H332 | GTCTGACTGCC | GUC | 11 | -18.7 | 8.2 | -10.5 | 94 | 88 | 0 |
| H337b | TGATGAGTCTGA | CUC | 12 | -17.6 | 6.3 | -11.3 | 100 | 99 | 80 |
| H340v2 | AACTTGATGAGTC | AUC | 13 | -17.4 | 7.1 | -10.3 | 99 | 66 | 0 |
| H346 | ATAGAGAAACTTGA | UUC | 14 | -17.2 | 9.7 | -7.5 | 69 | 10 | 0 |
| H349 | TTGATAGAGAAACT | CUC | 14 | -17.2 | 10.6 | -6.6 | 55 | 23 | 0 |
| H352 | GCTTTGATAGAGAA | AUC | 14 | -18.5 | 1.7 | -16.8 | 94 | 100 | 84 |

These three ribozymes are shown in FIGS. 3A, B and C, labeled respectively HDH, HEH and HFH.

EXAMPLE 2
Ribozymes Containing Thiophosphate

The purpose of this example was to evaluate the activity of ribozymes containing substitutions of thiophosphate for phosphate at some backbone positions.

Ribozymes to the HIV-1 tat gene were synthesized on an ABI synthesizer using standard phosphoramidite chemistry, however, at steps where thiophosphate was to be incorporated in the backbone the standard oxidation step (involving Iodine) was replaced with an oxidation step utilizing the Beaucage sulfur transfer reagent. Deprotected and desalted RNA was gel purified, eluted, kinased and sequenced to ensure that the sequence was correct. The end-labeled RNA was also treated with $H_2O_2$ which preferentially promotes cleavage at positions containing thiophosphate.

Ribozyme activity was tested against cleavage of a short (12 nucleotides) end-labeled substrate RNA. Substrate concentration was approximately 1 nM; ribozyme concentration was 5–100 nM; incubation was at 37° C. in 75 mM Tris (pH 7.5), 0.1 mM EDTA, 10 mM $MgCl_2$ for 2–40 minutes. Cleavage extents were determined by gel electrophoresis (PAGE) followed by quantitation on the AMBIS.

The ribozymes are shown in FIGS. 4A–4G. The following ribozymes showed essentially 100% activity: r37 (unmodified), r37s2 (1 thio on 5' arm, 2 on 3' arm), r37s4 (3 thio modifications on each arm), s37A (3 modifications on 3' arm), s37B (3 modifications alternating on 3' arm).

Ribozymes that are fully modified showed some decrease in activity, for example, s37C (almost completely modified on substrate binding arms) showed a 3x reduction in activity relative to unmodified, s37D (thio modifications in stem I, II and III) showed about a 9x reduction in activity relative to unmodified.

EXAMPLE 3
2'-O-methyl-containing Ribozymes

Figure 5:
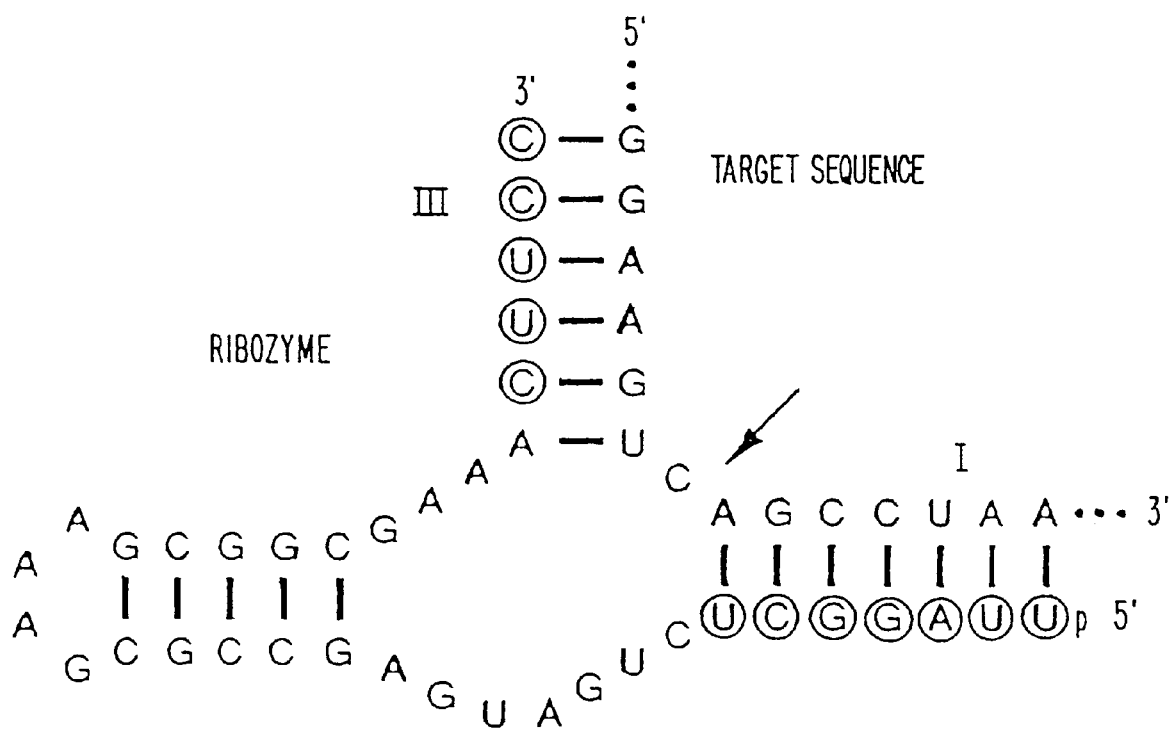
FIG. 5 is a diagrammatic representation of a chemically modified ribozyme of this invention (circled bases are modified with 2'-O-methyl), specifically the ribozyme is 2'-O-methyl HCH-037A.
Figure 6A:
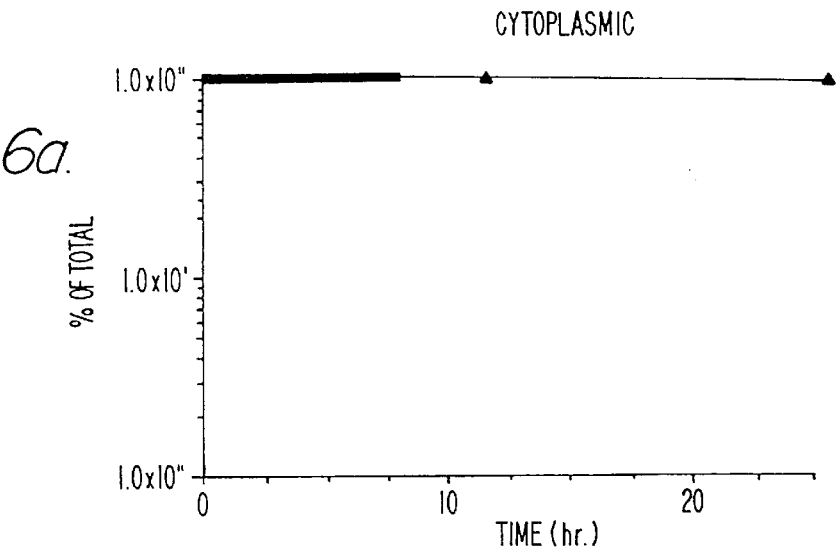
FIG. 6 is a graphical representation of ribozyme stability in Vero cell or HeLa cell extracts from cytoplasm, membrane, and nucleus.
Figure 6B:
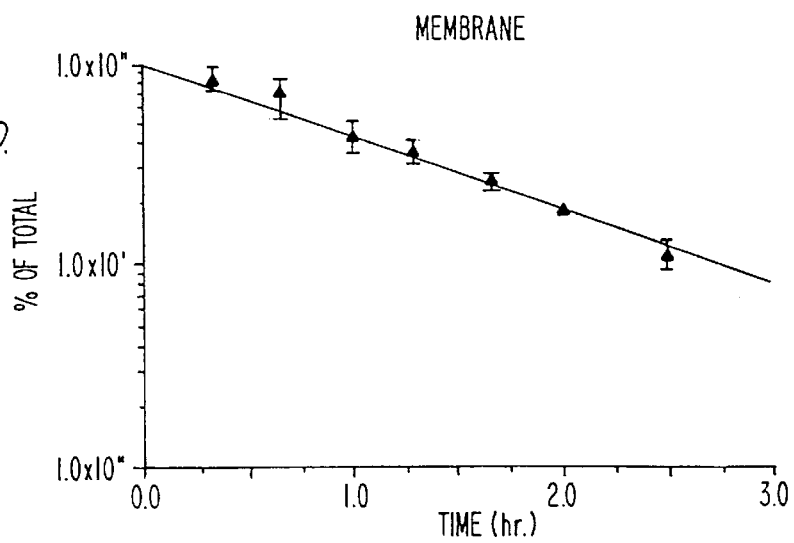
Figure 6C:
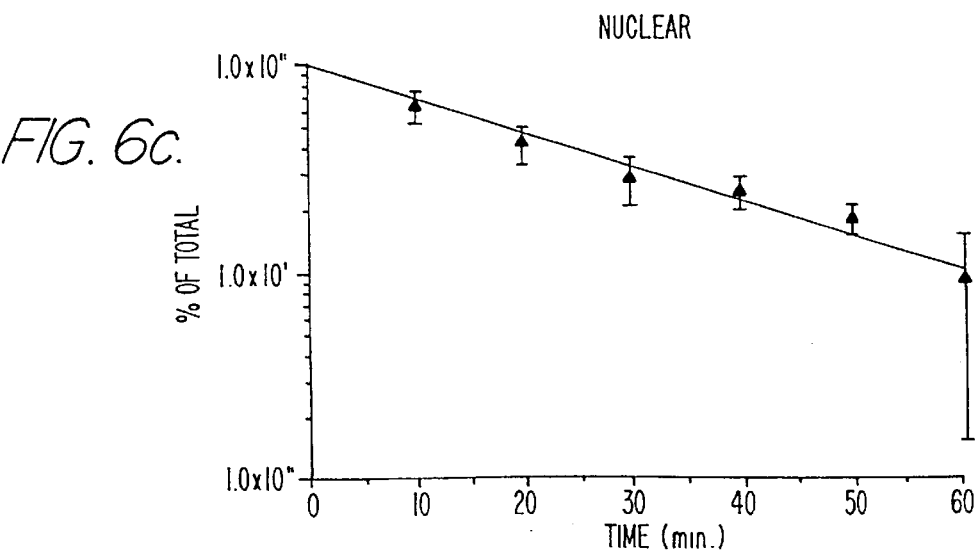
Figure 6D:
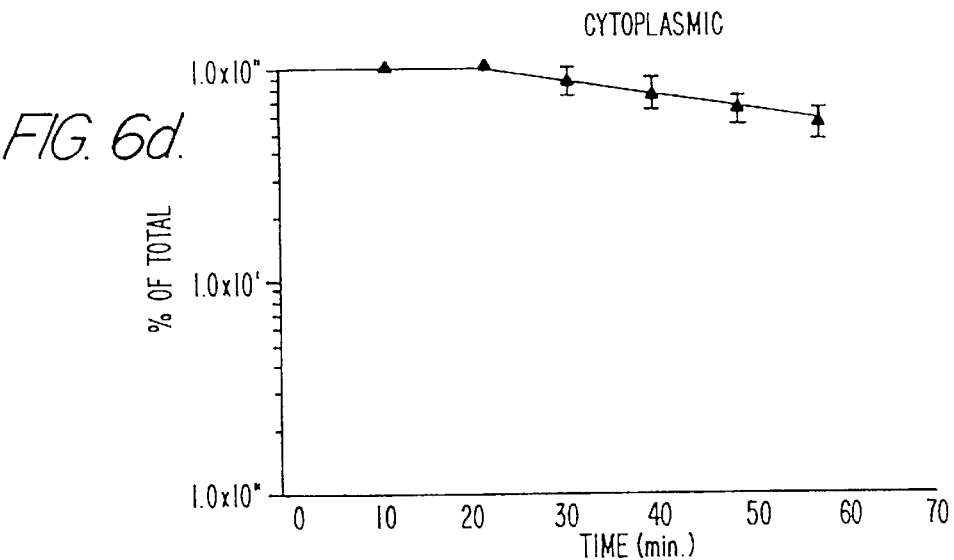
Figure 6E:
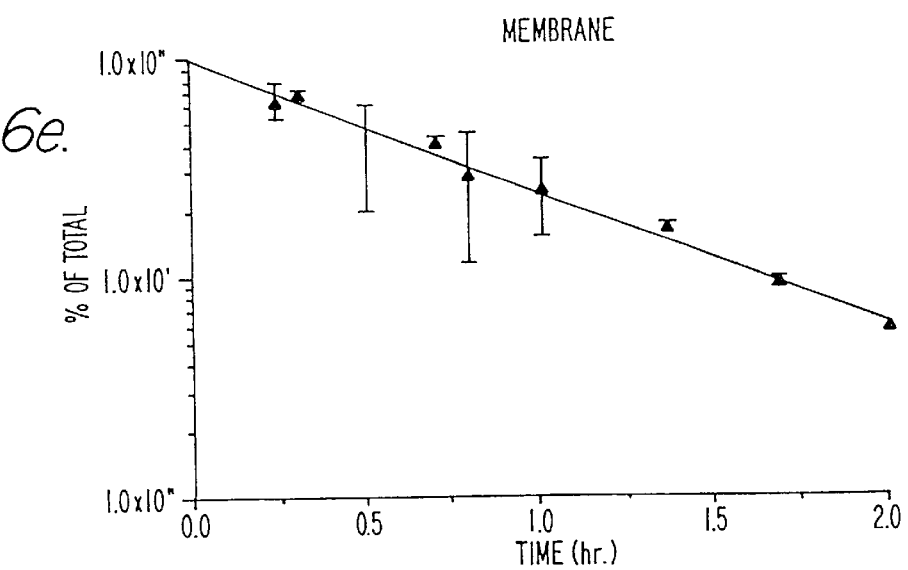
Figure 6F:
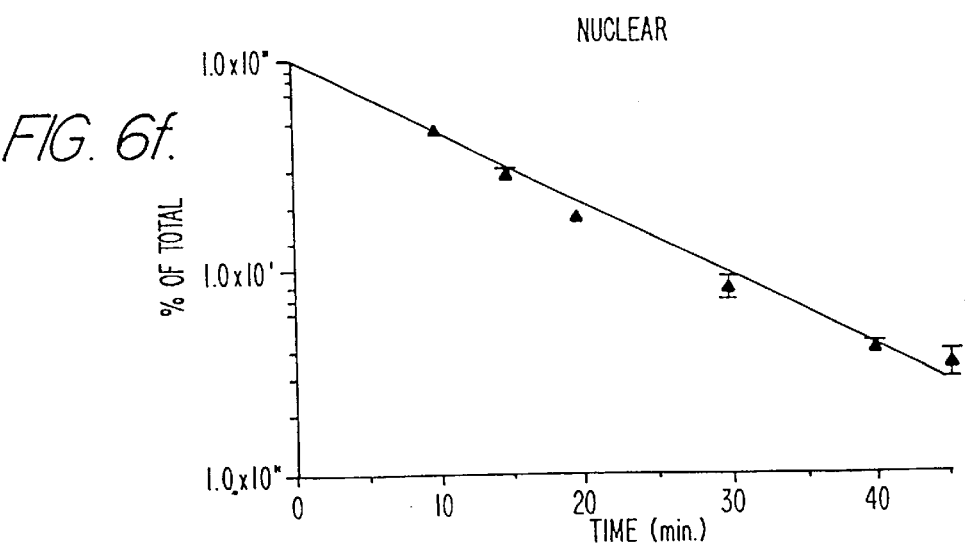

Ribozymes were made on an ABI synthesizer using standard phosphoramidite chemistry with 2'-O-methyl phos- Referring to FIG. 5, a ribozyme containing 2'-O-methyl at all positions that base-pair with substrate (except for the A at the 5' side of stem III) was synthesized. The Kcat/Km for the 2'-O-methyl ribozyme was $44 \times 10^6$ $M^{-1}$ $min^{-1}$ compared to $41 \times 10^6$ $m^{-1}$ $min^{-1}$ for the unmodified, and $32 \times 10^6$ for a thiophosphate modified ribozyme. Thus, the 2'-O-methyl ribozyme retains 100% activity.

EXAMPLE 4
Targeting the LTR and TAT Regions of HIV-1

The following example extends those provided above to show useful ribozymes targeted to the LTR and TAT regions of HIV-1. Details of methodology used herein are provided in Stinchcomb et al., Methods and Compositions for Treatment of Restenosis and Cancer Using Ribozymes, U.S. Ser. No. 08/245,466, filed May 18, 1994 hereby incorporated by reference herein. Such details are not required to practice the invention. Numbering of bases is according to GenBank Nos. K03455 (HIVHXB2) (numbered from transcription start site).

Screening LTR region for HH Ribozyme Sites

The LTR is among the most conserved regions within the HIV-1 genome. Also, the LTR region is present in all the transcripts generated during HIV-1 life cycle. So, ribozymes that cleave LTR targets will potentially block HIV replication.

There are 43 potential hammerhead (HH) ribozyme sites within the HIV-1 LTR. Ten hammerhead ribozymes were synthesized based on a) proper folding of the ribozyme with its target and b) conservation of target sequence among all HIV-1 strains.

RNA Synthesis

Ribozymes with 7/7 binding arms were synthesized using RNA phosphoramadite chemistry. Ribozymes were deprotected and purified as described above.

Target RNA used in this study was 613 nt long and contained cleavage sites for all the 10 HH ribozymes targeted against LTR. A template containing T7 RNA polymerase promoter upstream of LTR target sequence, was PCR amplified from an HIV-1 pro-DNA clone. Other such clones can be readily constructed. Target RNA was transcribed from this PCR amplified template using T7 RNA polymerase. The transcript was internally labeled during transcription by including [$\alpha$-$^{32}$P] CTP as one of the four ribonucleotide triphosphates. The transcription mixture was treated with DNase-1, following transcription at 37° C. for 2 hours, to digest away the DNA template used in the transcription. RNA was precipitated with isopropanol and the pellet was washed two times with 70% ethanol to get rid of salt and nucleotides used in the transcription reaction. RNA is resuspended in DEPC-treated water and stored at 4° C.

Ribozyme Cleavage Reactions

Reactions were carried out under ribozyme excess ($_{cat}$/ K$_m$) conditions (Herschlag and Cech (1990) *Biochemistry* 29, 10159–10171). Briefly, 1,000 nM ribozyme and 10 nM internally labeled target RNA were denatured separately by heating to 90° C. for 2 min in the presence of 50 mM Tris.HCl, pH 7.5 and 10 mM MgCl$_2$. The RNAs were renatured by cooling to 37° C. for 10–20 min. Cleavage reaction was initiated by mixing the ribozyme and target RNA at 37° C. Aliquots of 5 μl were taken at regular intervals of time and the reaction was quenched by adding equal volume of stop buffer and freezing on dry ice. The samples were resolved on sequencing gel.

Results

Figure 10:
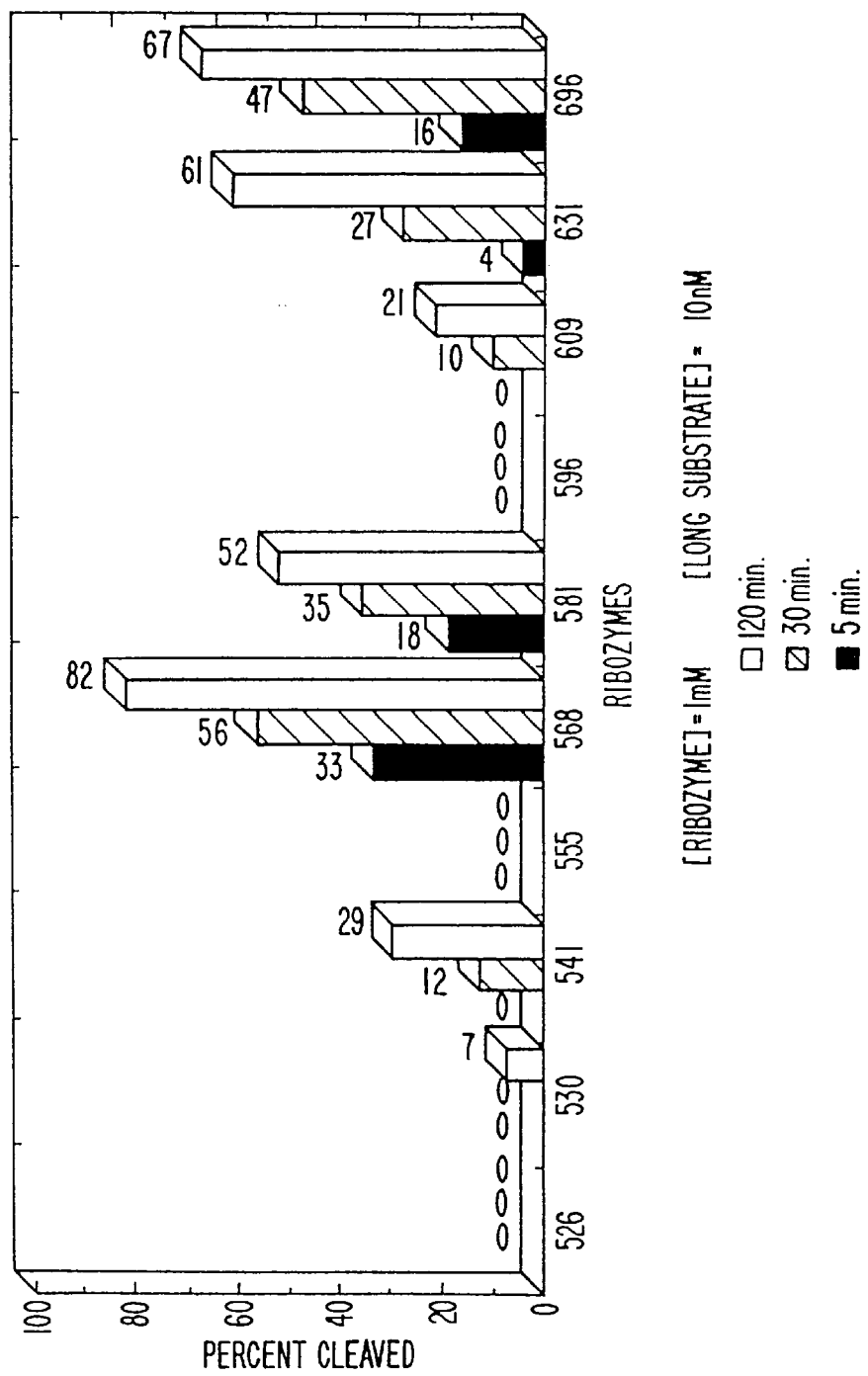
FIG. 10 is a graphical representation of activity of various LTR-targeted ribozymes.

As shown in FIG. 10, of the ten ribozymes that were tested individually, only four HH ribozymes (568, 581, 631, 696) cleaved the LTR RNA. Other target sites appear to be inaccessible to ribozyme binding and cleavage. Site 568 is also referred to as site 115 and has been targeted for hammerhead ribozyme cleavage by Drouplic et al., 66 *J. Virol.* 1432–1441, 1992 and Heidenreich and Eckstein, 267 *J. Biol. Chem.* 1904–1909, 1992.

Figure 11:
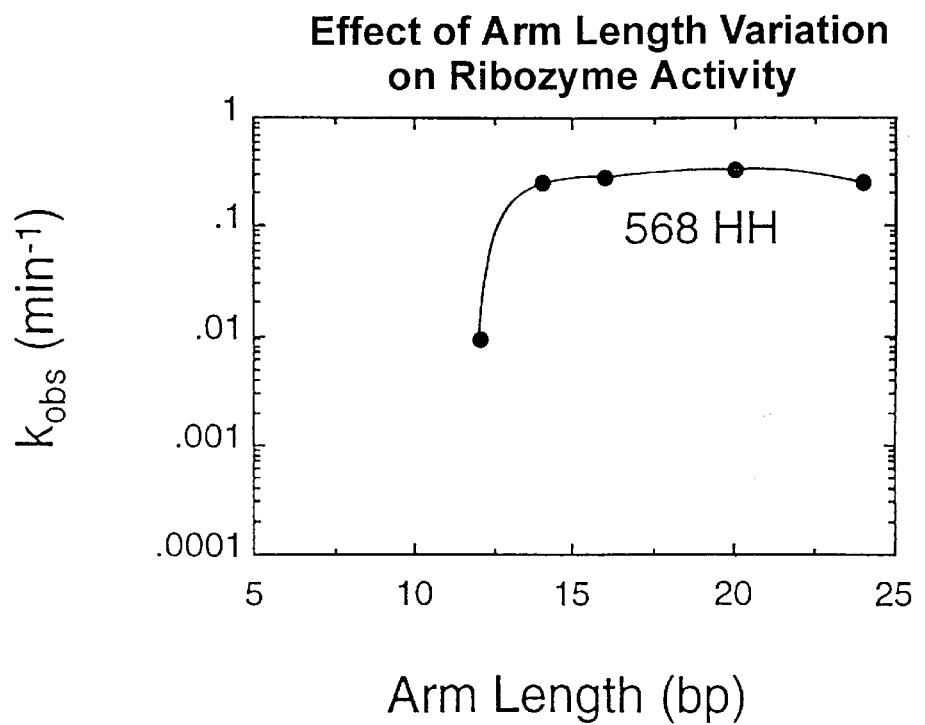
FIG. 11 is a graphical representation of activity of ribozymes of various arm lengths.

Since 568 HH ribozyme was cleaving its target to a greater extent than the others, we were interested in optimizing the length of binding arms of this HH ribozyme. As shown in FIG. 11, the rate of ribozyme cleavage increased significantly when the length of the binding arm was increased from 12 to 14 base pairs (total). There was no significant improvement in the activity of ribozymes with binding arms longer than 14 base pairs.

Chemical modification of HH ribozymes targeted to a specific site can significantly improve the stability of the ribozyme in human serum. Further, these modifications do not seem to have any significant effect on the catalytic activity of the ribozyme. All the 2' hydroxyl groups within the ribozyme, with the exception of positions U4, G5, A6, U7, G8, G12 and A15.1 (using standard nomenclature, See FIG. 14), were modified with 2'-O-methyl groups. The 2' hydroxyl groups at U4 and U7 were modified with either 2'amino, 2'-C-allyl, 2'-O-methyl or 2'ara-flouro. See Usman et al., 2'-Deoxy 2'-alkylnucleotide containing Nucleic Acid, U.S. Ser. No. 08/218,934, filed Mar. 29, 1994, hereby incorporated by reference herein.

Figure 12:
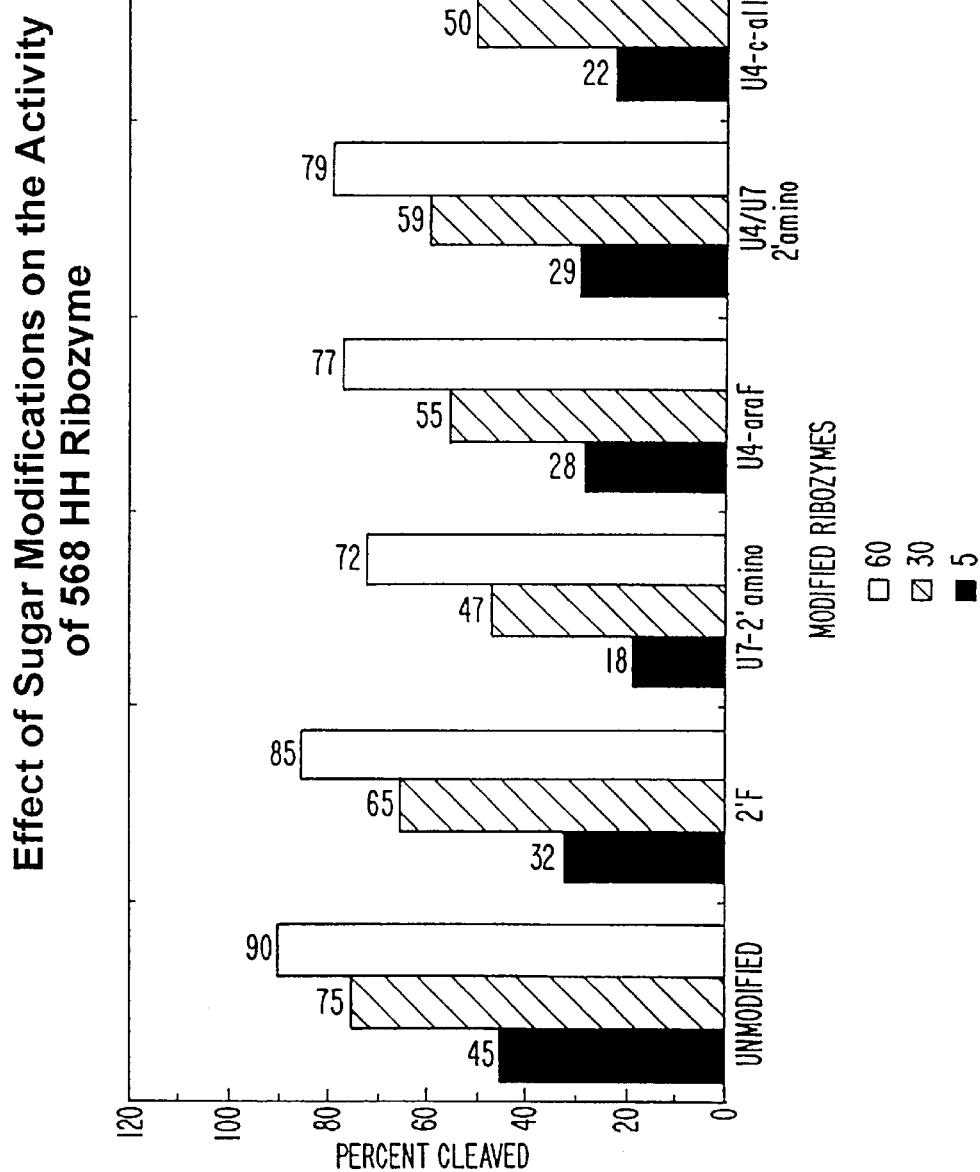
FIG. 12 is a graphical representation of ribozymes with different sugar modifications.

Referring to FIG. 12, the 568 HH ribozyme could be stabilized by chemical modification of the sugar moeity of various bases (similar to the ones listed above). The 568 HH ribozyme was extensively modified with one of the following compounds: 2'flouro, 2'amino at the U7 position, araflouro at U4 position, 2'amino at U4 and U7 positions, c-allyl at U4 position. None of the above modifications had any deleterious effect on the ribozyme activity.

Transfection of cells with 568 HH ribozyme (with U4 and U7 positions containing 2'amino modifications) blocks the replication of HIV-1 replication.

Screening TAT Region for HH Ribozyme Sites

A region of the TAT mRNA is present in the majority of the transcripts generated during HIV-1 life cycle. So, ribozymes that cleave TAT targets will potentially block HIV replication.

There are 54 potential HH ribozyme site within the HIV-1 TAT regions (between 5776 nt and 6044 nt). Nine hammerhead ribozymes were synthesized based on a) proper folding of the ribozyme with its target and b) conservation of target sequence among all HIV-1 strains.

RNA synthesis and ribozyme cleavage reactions were carried out as described above. Target RNA used in this study was 422 nt long.

Figure 13:
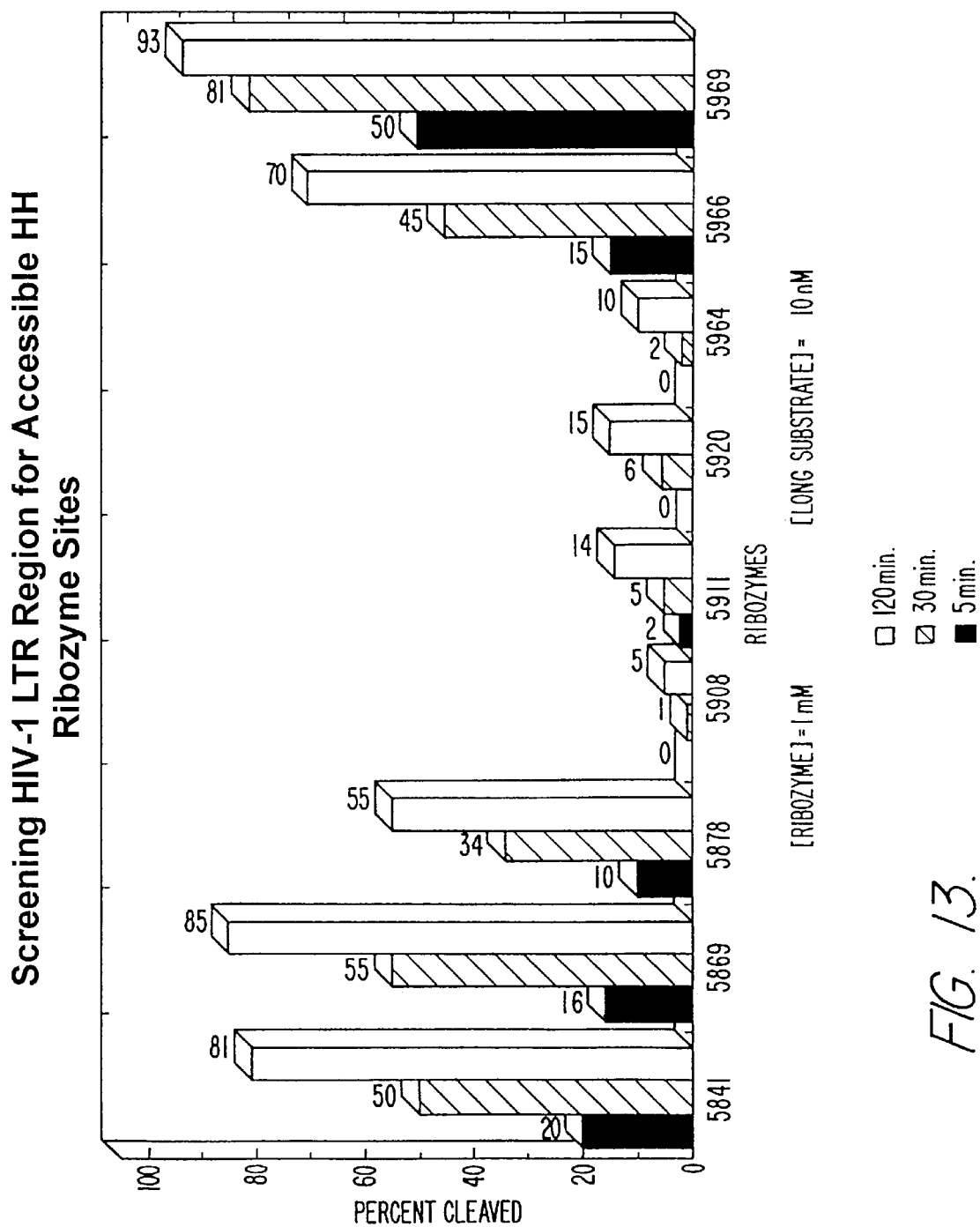
FIG. 13 is a graphical representation of activity of various TAT-targeted ribozymes.

As shown in FIG. 13, five sites (5841, 5869, 5878, 5966, 5969) are cleaved more readily than the others. None of these hammerhead sites have previously been targeted.

Screening HIV-1 Genome for Hairpin Ribozyme Sites

Referring to Table VIII and FIG. 15, there are 27 potential hairpin (HP) ribozyme sites in the HIV-1 genome. Ribozymes shown in the table were synthesized and tested. Modifications to various regions of the hairpin structure can be made without deleterious effect, e.g., in those targetted to n.t. positions 565 and 4398 two extra bases can be inserted in place of GGCA (3rd col.) to GGCACA; and GCAG to GCAGUC respectively.

Site 565 within the LTR region (Ojwang et al., (1992) PNAS. USA. 89, 10802–10806; Yu et al., (1993) PNAS. USA. 90, 6340–6344) and 4398 within the POL region of the HIV-1 genome (Joseph and Burke (1993) J. Biol. Chem. 268, 24515–24518) have been shown to be accessible to HP ribozyme binding and cleavage. We have also found that HP ribozymes targeted towards 565 and 4398 sites are active.

The best HH and HP ribozymes are shown in Table VII, with their associated cleavage and target sites.

Administration of Ribozyme

Selected ribozymes can be administered prophylactically, or to HIV-1 infected patients, e.g., by exogenous delivery of the ribozyme to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of ribozymes are also suitable.

The specific delivery route of any selected ribozyme will depend on the use of the ribozyme. Generally, a specific delivery program for each ribozyme will focus on unmodified ribozyme uptake with regard to intracellular localization, followed by demonstration of efficacy. Alternatively, delivery to these same cells in an organ or tissue of an animal can be pursued. Uptake studies will include uptake assays to evaluate cellular ribozyme uptake, regardless of the delivery vehicle or strategy. Such assays will also determine the intracellular localization of the ribozyme following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:

a. encapsulation in liposomes, b. transduction by retroviral vectors, c. conjugation with cholesterol, d. localization to nuclear compartment utilizing antigen binding or nuclear targeting site found on most snRNAs or nuclear proteins, e. neutralization of charge of ribozyme by using nucleotide derivatives, and f. use of blood stem cells to distribute ribozymes throughout the body.

At least three types of delivery strategies are useful in the present invention, including: ribozyme modifications, particle carrier drug delivery vehicles, and retroviral expression vectors. Unmodified ribozymes, like most small molecules, are taken up by cells, albeit slowly. To enhance cellular uptake, the ribozyme may be modified essentially at random, in ways which reduce its charge but maintains specific functional groups. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge allowing free diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein. In another study, an antibody targeted liposome delivery system containing an RNA molecule 3,500 nucleotides in length and antisense to a structural protein of HIV, inhibited virus proliferation in a sequence specific manner. Not only did the antibody target the liposomes to the infected cells, but it also triggered the internalization of the liposomes by the infected cells. Triggering the endocytosis is useful for viral inhibition. Finally, liposome delivered synthetic ribozymes have been shown to concentrate in the nucleus of H9 (an example of an HIV-sensitive cell) cells and are functional as evidenced by their intracellular cleavage of the sequence. Liposome delivery to other cell types using smaller ribozymes (less than 142 nucleotides in length) exhibit different intracellular localizations.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell. This method is particularly useful for treating AIDS using anti-HIV ribozymes of this invention.

Also preferred in AIDS therapy is the use of a liposome formulation which can deliver oligonucleotides to lymphocytes and macrophages. This oligonucleotide delivery system inhibits HIV proliferation in infected primary immune cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration. This formulation offers an excellent delivery vehicle for anti-AIDS ribozymes for two reasons. First, T-helper lymphocytes and macrophages are the primary cells infected by the virus, and second, a subcutaneous administration delivers the ribozymes to the resident HIV-infected lymphocytes and macrophages in the lymph node. The liposomes then exit the lymphatic system, enter the circulation, and accumulate in the spleen, where the ribozyme is delivered to the resident lymphocytes and macrophages.

Intraperitoneal administration also leads to entry into the circulation, with once again, the molecular weight or size of the ribozyme-delivery vehicle complex controlling the rate of entry.

Liposomes injected intravenously show accumulation in the liver, lung and spleen. The composition and size can be adjusted so that this accumulation represents 30% to 40% of the injected dose. The remaining dose circulates in the blood stream for up to 24 hours.

The chosen method of delivery should result in cytoplasmic accumulation in the afflicted cells and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogues may require different dosaging. Descriptions of useful systems are provided in the art cited above, all of which is hereby incorporated by reference herein.

The claimed ribozymes are also useful as diagnostic tools to specifically or non-specifically detect the presence of a target RNA in a sample. That is, the target RNA, if present in the sample, will be specifically cleaved by the ribozyme, and thus can be readily and specifically detected as smaller RNA species. The presence of such smaller RNA species is indicative of the presence of the target RNA in the sample.

Other embodiments are within the following claims.

TABLE VII

HIV (Strain HXB-2) Ribozyme and Target Sequences that Have Been Screened and Tested In Vitro

| Type | nt. Position | Hairpin Ribozyme Sequence | Substrate Sequence |
|---|---|---|---|
| HP | 121 | CACCAUCCAAAG AGAA GUGG ACCAGAGAAACACACGUUGUGGUACAUUACCUGGUA | CCACU GAC CUUUGGAUGGUG |
| HP | 515 | UAUUGAGGCUUA AAGA GUGG ACCAGAGAAACACACGUUGUGGUACAUUACCUGGUA | CCACU GCU UAAGCCUCAAUA |
| HP | 565 | AGUCACACAACA AGAA GGCA ACCAGAGAAACACACGUUGUGGUACAUUACCUGGUA | UGCCC GUC UGUUGUGUGACU |
| HP | 565 | AGUCACACAACA AGAAGGCACAACCAGAGAAACACACGUUGUGGUACAUUACCUGGUA | UGCCC GUC UGUUGUGUGACU |
| HP | 2025 | UUCCACAUUUCC AAGA GCCC ACCAGAGAAACACACGUUGUGGUACAUUACCUGGUA | GGGCU GUU GGAAAUGUGGAA |
| HP | 4398 | GCCAUAUUCCUG AGAAGCAGUCACCAGAGAAACACACGUUGUGGUACAUUACCUGGUA | CUGUA GUC CAGGAAUAUGGC |
| HP | 4398 | GCCAUAUUCCUG AGAA GCAG ACCAGAGAAACACACGUUGUGGUACAUUACCUGGUA | CUGUA GUC CAGGAAUAUGGC |
| HP | 9205 | CACCAUCGAAAG AGAA GUGG ACCAGAGAAACACACGUUGUGGUACAUUACCUGGUA | CCACU GAC CUUUGGAUGGUG |
| HP | 9599 | UAUUGAGGCUUA AAGA GUGG ACCAGAGAAACACACGUUGUGGUACAUUACCUGGUA | CCACU GCU UAAGCCUCAAUA |
| HP | 9649 | AGUCACACAACA AGAA GGCA ACCAGAGAAACACACGUUGUGGUACAUUACCUGGUA | UGCCC GUC UGUUGUGUGACU |

| Type | nt. Position | Hammerhead Ribozyme Sequence | Substrate Sequence |
|---|---|---|---|
| HH | 520 | UUUAUUGAGGCU CUGAUGAGGCCGAAAGGCCGAA AAGCAGUGGGUU | AACCCACUGCUUA AGCCUCAAUAAA |
| HH | 526 | GCAAGCUUUAUU CUGAUGAGGCCGAAAGGCCGAA AGGCUUAAGCAG | CUGCUUAAGCCUC AAUAAAGCUUGC |
| HH | 530 | CAAGGCAAGCUU CUGAUGAGGCCGAAAGGCCGAA AUUGAGGCUUAA | UUAAGCCUCAAUA AAGCUUGCCUUG |
| HH | 541 | CUUGAAGCACUC CUGAUGAGGCCGAAAGGCCGAA AGGCAAGCUUUA | UAAAGCUUGCCUU GAGUGCUUCAAG |
| HH | 555 | ACGGGCACACAC CUGAUGAGGCCGAAAGGCCGAA ACUUGAAGCACU | AGUGCUUCAAGUA GUGUGUGCCCGU |
| HH | 568 | AGUCACACAACA CUGAUGAGGCCGAAAGGCCGAA ACGGGCACACAC | GUGUGUGCCCGUC UGUUGUGUGACU |
| HH | 581 | CUCUAGUUACCA CUGAUGAGGCCGAAAGGCCGAA AGUCACACAACA | UGUUGUGUGACUC UGGUAACUAGAG |
| HH | 596 | AAGGGUCUGAGG CUGAUGAGGCCGAAAGGCCGAA AUCUCUAGUUAC | GUAACUAGAGAUC CCUCAGACCCUU |
| HH | 609 | CCACACUGACUA CUGAUGAGGCCGAAAGGCCGAA AAGGGUCUGAGG | CCUCAGACCCUUU UAGUCAGUGUGG |
| HH | 631 | GGGCGCCACUGC CUGAUGAGGCCGAAAGGCCGAA AGAGAUUUCCA | UGGAAAAUCUCUA GCAGUGGCGCCC |
| HH | 696 | CUUCAGCAAGCC CUGAUGAGGCCGAAAGGCCGAA AGUCCUGCGUCG | CGACGCAGGACUC GGCUUGCUGAAG |

TABLE VII-continued

HIV (Strain HXB-2) Ribozyme and Target Sequences that Have Been Screened and Tested In Vitro

| | | | | |
|---|---|---|---|---|
| HH | 805 | CCGCUUAAUACU | CUGAUGAGGCCGAAAGGCCGAA | ACGCUCUCGCAC | GUGCGAGAGCGUC AGUAUUAAGCGG |
| HH | 2028 | UUCCACAUUUCC | CUGAUGAGGCCGAAAGGCCGAA | ACAGCCCUUUUU | AAAAAGGGCUGUU GGAAAUGUGGAA |
| HH | 4398 | AUAUUCCUGGAC | CUGAUGAGGCCGAAAGGCCGAA | ACAGUCUACUUG | CAAGUAGACUGUA GUCCAGGAAUAU |
| HH | 5841 | UAGUCUAGGAUC | CUGAUGAGGCCGAAAGGCCGAA | ACUGGCUCCAUU | AAUGGAGCCAGUA GAUCCUAGACUA |
| HH | 5869 | GCUGACUUCCUG | CUGAUGAGGCCGAAAGGCCGAA | AUGCUUCCAGGG | CCCUGGAAGCACC CAGGAAGUCAGC |
| HH | 5878 | CAGUUUUAGGCU | CUGAUGAGGCCGAAAGGCCGAA | ACUUCCUGGAUG | CAUCCAGGAAGUC AGCCUAAAACUG |
| HH | 5908 | AACACUUUUUAC | CUGAUGAGGCCGAGAGGCCGAA | AUAGCAAUUGGU | ACCAAUUGCUAUU GUAAAAAGUGUU |
| HH | 5911 | AGCAACACUUUU | CUGAUGAGGCCGAAAGGCCGAA | ACAAUAGCAAUU | AAUUGCUAUUGUA AAAAGUGUUGCU |
| HH | 5920 | GGCAAUGAAAGC | CUGAUGAGGCCGAAAGGCCGAA | ACACUUUUUACA | UGUAAAAAGUGUU GCUUUCAUUGCC |
| HH | 5964 | CCUGCCAUAGGA | CUGAUGAGGCCGAAAGGCCGAA | AUGCCUAAGGCU | AGCCUUAGCCAUC UCCUAUGGCAGG |
| HH | 5966 | UUCCUGCCAUAG | CUGAUGAGGCCGAAAGGCCGAA | AGAUGCCUAAGG | CCUUAGGCAUCUC CUAUGGCAGGAA |
| HH | 5969 | UUCUUCCUGCCA | CUGAUGAGGCCGAAAGGCCGAA | AGGAGAUGCCUA | UAGGCAUCUCCUA UGGGAGCAAGAA |
| HH | 9604 | UUUAUUGAGGCU | CUGAUGAGGCCGAAAGGCCGAA | AAGCAGUGGGUU | AACCCACUGUUUA AGCCUCAAUAAA |
| HH | 9610 | GCAAGCUUUAUU | CUGAUGAGGCCGAAAGGCCGAA | AGGCUUAAGCAG | CUGCUUAAGCCUC AAUAAAGCUUGC |
| HH | 9614 | CAAGACAAGCUU | CUGAUGAGGCCGAAAGGCCGAA | AUUGAGGCUUAA | UUAAGCCUCAAUA AAGCUUGCCUUG |
| HH | 9625 | CUUGAAGCACUC | CUGAUGAGGCCGAAAGGCCGAA | AGGCAAGCUUUA | UAAAGCUUGCCUU GAGUGCUUCAAG |
| HH | 9639 | ACGGGCACACAC | CUGAUGAGGCCGAAAGGCCGAA | ACUUGAAGCACU | AGUGCUUCAAGUA GUGUGUGCCCGU |
| HH | 9652 | AGUCACACAACA | CUGAUGAGGCCGAAAGGCCGAA | ACGGGCACACAC | GUGUGUGCCCGUC UGUUGUGUGACU |
| HH | 9665 | CUCUAGUUACCA | CUGAUGAGGCCGAAAGGCCGAA | AGUCACACAACA | UGUUGUGUGACUC UGGUAACUAGAG |
| HH | 9680 | AAGGGUCUGAGG | CUGAUGAGGCCGAAAGGCCGAA | AUCUCUAGUUAC | GUAACUAGAGAUC CCUCAGACCCUU |
| HH | 9693 | CCACACUGACUA | CUGAUGAGGCCGAAAGGCCGAA | AAGGGUCUGAGG | CCUCAGACCCUUU UAGUCAGUGUGG |

TABLE VIII

HIV (Strain HXB2) Hairpin Ribozyme Sqequence

| nt. Position | Hairpin Ribozyme Sequence | Substrate Sequence |
|---|---|---|
| 121 | CACCAUCCAAAG AGAA GUGG ACCAGAGAAACACACGUUGUGGUACAUUACCUGGUA | CCACU GAC CUUUGGAUGGUG |
| 270 | GAAAUGCUAGGC AGAA GUCA ACCAGAGAAACACACGUUGUGGUACAUUACCUGGUA | UGACA GCC GCCUAGCAUUUC |
| 273 | GAUGAAAUGCUA AGAA GCUG ACCAGAGAAACACACGUUGUGGUACAUUACCUGGGA | CAGCC GCC UAGCAUUUCAUC |
| 515 | UAUUGAGGGUUA AAGA GUGG ACCAGAGAAACACACGUUGUGGUACAUUACCUGGGA | CCACU GCU UAAGCCUCAAUA |
| 565 | AGUCACACAACA AGAA GGCA ACCAGAGAAACACACGUUGUGGUACAUUACCUGGUA | UGCCC GUC UGUUGUGUGACU |
| 565 | AGUCACACAACA AGAAGGCACA ACCAGAGAAACACACGUUGUGGUACAUUACCUGGUA | UGCCC GUC UGUUGUGUGACU |
| 2025 | UUCCACAUUUCC AAGA GCCC ACCAGAGAAACACACGUUGUGGUACAUUACCUGGUA | GGGGU GUU GGAAAUGUGGAA |
| 3273 | GGCAGCACUAUA AGAA GUAC ACCAGAGAAACACACGUUGUGGUACAUUACCUGGUA | GUACA GCC UAUAGUGCUGCC |
| 3720 | UCCUUUUGUAUG AGAA GUUU ACCAGAGAAACACACGUUGUGGUACAUUACCUGGUA | AAACU GCC CAUACAAAAGGA |
| 4039 | UGCAUAUUGUGA AGAA GUUA ACCAGAGAAACACACGUUGUGGUACAUUACCUGGUA | UAACA GUC UCACAAUAUGCA |
| 4398 | GCCAUAUUCCUG AGAA GCAG ACCAGAGAAACACACGUUGUGGUACAUUACCUGGUA | CUGUA GUC CAGGAAUAUGGC |
| 4398 | GCCAUAUUCCUG AGAAGCAGUC ACCAGAGAAACACACGUUGUGGUACAUUACCUGGUA | CUGUA GUC CAGGAAUAUGGC |
| 4612 | CGCCCACCAACA AGAA GCCC ACCAGAGAAACACACGUUGUGCUACAUUACCUGGGA | GGGCC GCC UGUUGGUGGGCG |
| 5348 | AUGAAUUAGUUG AGAA GCUA ACCAGAGAAACACACGUUGUGGUACAUUACCUGGUA | UAGCA GCC CAACUAAUUCAU |
| 5379 | CAGAGUCUGAAA AGAA GUCA ACCAGAGAAACACACGUUGUGGUACAUUACCUGGUA | UGACU GUU UUUCAGACUCUG |
| 5760 | UGAAAAUGGAUA AGAA GCAG ACCAGAGAAACACACGUUGUGGUACAUUACCUGGGA | CUGCU GUU UAUCCAUUUUCA |
| 6334 | UACCCCAUAAUA AGAA GUGA ACCAGAGAAACACACGUUGUGGUACAUUACCUGGGA | UCACA GUC UAUUAUGGGGUA |
| 6454 | UUGUGGGUUGGG AGAA GUGG ACCAGAGAAACACACGUUGUGGUACAUUACCUGGUA | CCACA GCC CCCAACCCACAA |
| 7013 | CUUCUUCUGCUA AGAA GCCA ACCAGAGAAACACACGUUGUGGUACAUUACCUGGGA | UGGCA GUC UAGCAGAAGAAG |
| 7346 | CUCCACAAUAAA AGAA GUGC ACCAGAGAAACACACGUUGUGGUACAUUACCUGGUA | GCACA GUU UUAAUUGUGGAG |
| 7392 | CAAGUACUAUUA AGAA GUUG ACCAGAGAAACACACGUUGUGGUACAUUACCUGGUA | CAACU GUU UAAUAGUACUUG |
| 7819 | CAGCGUCAUUGA AGAA GCGC ACCAGAGAAACACACGUUGUGGUACAUUACCUGGUA | GCGCA GCC UCAAUGACGCUG |
| 7833 | CUGGCCUGUACC AGAA GCGU ACCAGAGAAACACACGUUGUGGUACAUUACCUGGUA | ACGGU GAC GGUACAGGCCAG |
| 7930 | CUUGAUGCCCCA AGAA GUGA ACCAGAGAAACACACGUUGUGGUACAUUACCUGGUA | UCACA GUC UGGGGCAUCAAG |
| 9205 | CACCAUCCAAAG AGAA GUGG ACCAGAGAAACACACGUUGUGGUACAUUACCUGGUA | CCACU GAC CUUUGGAUGGUG |
| 9354 | GAAAUGCUAGGC AGAA GUCA ACCAGAGAAACACACGUUGUGGUACAUUACCUGGUA | UGACA GCC GCCUAGCAUUUC |
| 9357 | GAUGAAAUGCUA AGAA GCUG ACCAGAGAAACACACGUUGUGGUACAUUACCUGGUA | CAGCC GCC UAGCAUUUCAUC |
| 9599 | UAUUGAGGCUUA AAGA GUGG ACCAGAGAAACACACGUUGUGGUACAUUACCUGGUA | CCACU GCU UAAGCCUCAAUA |
| 9649 | AGUCACACAACA AGAA GGCA ACCAGAGAAACACACGUUGUGGUACAUUACCUGGUA | UGCCC GUC UGUUGUGUGACU |

We claim:

1. An enzymatic nucleic acid molecule which specifically cleaves RNA encoded by the nef gene of human immunodeficiency virus.

2. The enzymatic nucleic acid molecule of claim 1, wherein said enzymatic nucleic acid molecule is in a hammerhead motif.

3. The enzymatic nucleic acid molecule of claim 1, wherein said enzymatic nucleic acid molecule is in a hairpin motif.

4. The enzymatic nucleic acid molecule of claim 1, wherein said enzymatic nucleic acid molecule is in a group I intron, group II intron, hepatitis delta virus ribozyme or RNase P M1 RNA motif.

5. The enzymatic nucleic acid molecule of claim 1, wherein said enzymatic nucleic acid molecule comprises a substrate binding site having between 12 and 100 nucleotides complementary to said nef RNA.

6. The enzymatic nucleic acid molecule of claim 1, wherein said enzymatic nucleic acid molecule comprises a substrate binding site having between 14 and 24 nucleotides complementary to said nef RNA.

7. An expression vector comprising nucleic acid sequence encoding one or more enzymatic nucleic acid molecule of claim 1 in a manner which allows expression of said enzymatic nucleic acid molecules.

8. The expression vector of claim 7, wherein said expression vector is a viral vector.

9. The expression vector of claim 8, wherein said viral vector is a retrovirus vector.

10. The enzymatic nucleic acid molecule of claim 1, wherein said enzymatic nucleic acid molecule is chemically synthesized.

11. The enzymatic nucleic acid molecule of claim 1, wherein said enzymatic nucleic molecule is in a purified form.

12. The enzymatic nucleic acid molecule of claim 1, wherein said enzymatic RNA molecule is active in the presence of divalent metal ions.

13. The enzymatic nucleic acid molecule of claim 12, wherein said divalent metal ion is magnesium.

14. The enzymatic nucleic acid molecule of claim 1, wherein said enzymatic nucleic molecule comprises a sugar modification.

15. The expression vector of claim 7, wherein said nucleic acid sequence encoding said enzymatic RNA molecule is under the control of a mammalian transcription promoter.

16. The expression vector of claim 15, wherein said mammalian transcription promoter is from a cytomegalovirus.

17. A method of cleaving RNA encoded by the nef gene comprising the step of contacting said RNA with the enzymatic nucleic acid molecule of claim 1 under conditions suitable for the cleavage of said RNA.

18. A mammalian cell including the enzymatic nucleic acid molecule of claim 1, wherein the mammalian cell is not part of a mammal.

19. The mammalian cell of claim 18, wherein said mammalian cell is a human cell.

20. A mammalian cell including the expression vector of claim 7.

21. The mammalian cell of claim 20, wherein said mammalian cell is a human cell.

22. The enzymatic nucleic acid molecule of claim 1, wherein said enzymatic nucleic acid molecule comprises a poly A tail.

* * * * *

SEQUENCE LISTING (1) GENERAL INFORMATION:

(iii) NUMBER OF SEQUENCES: 232

(2) INFORMATION FOR SEQ ID NO:1:

(i) SEQUENCE CHARACTERISTICS:
      (A) LENGTH: 40 base pairs (B) TYPE:            nucleic acid
            (C) STRANDEDNESS:    single
            (D) TOPOLOGY:        linear (xi) SEQUENCE DESCRIPTION: SEQ ID NO:1:

AGAAGAAAAG CAAAGAUCAU UAGGGAUUAU GGAAAACAGA                              40

(2) INFORMATION FOR SEQ ID NO:2:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:2:

AGUUUAGUAA AACAC                                                        15

(2) INFORMATION FOR SEQ ID NO:3:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:3:

CCAUAUGUAU AUUUC                                                        15

(2) INFORMATION FOR SEQ ID NO:4:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:4:

UCAGAAGUAC ACAUC                                                        15

(2) INFORMATION FOR SEQ ID NO:5:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any
                base.

(xi) SEQUENCE DESCRIPTION: SEQ ID NO:5:

AGAUUGGUAG UAANA                                                        15

(2) INFORMATION FOR SEQ ID NO:6:

(i) SEQUENCE CHARACTERISTICS:
            (A) LENGTH:          16 base pairs
            (B) TYPE:            nucleic acid
            (C) STRANDEDNESS:    single
            (D) TOPOLOGY:        linear (xi) SEQUENCE DESCRIPTION: SEQ ID NO:6:

AAUAACAACA UAUUGG                                                       16

(2) INFORMATION FOR SEQ ID NO:7:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:7:

AUUGGGGUCU GCAUA                                                         15

(2) INFORMATION FOR SEQ ID NO:8:

(i) SEQUENCE CHARACTERISTICS:
        (A) LENGTH:        28 base pairs
        (B) TYPE:          nucleic acid
        (C) STRANDEDNESS:  single
        (D) TOPOLOGY:      linear (xi) SEQUENCE DESCRIPTION: SEQ ID NO:8:

AUACAGGAGA AAGAGACUGG CAUUUGGG                                           28

(2) INFORMATION FOR SEQ ID NO:9:

(i) SEQUENCE CHARACTERISTICS:
        (A) LENGTH:        23 base pairs
        (B) TYPE:          nucleic acid
        (C) STRANDEDNESS:  single
        (D) TOPOLOGY:      linear (xi) SEQUENCE DESCRIPTION: SEQ ID NO:9:

AUCUGGGUCA GGGAGUCUCC AUA                                                23

(2) INFORMATION FOR SEQ ID NO:10:

(i) SEQUENCE CHARACTERISTICS:
        (A) LENGTH:        30 base pairs
        (B) TYPE:          nucleic acid
        (C) STRANDEDNESS:  single
        (D) TOPOLOGY:      linear (xi) SEQUENCE DESCRIPTION: SEQ ID NO:10:

AAAAAGAGAU AUAGCACACA AGUAGACCCU                                         30

(2) INFORMATION FOR SEQ ID NO:11:

(i) SEQUENCE CHARACTERISTICS:
        (A) LENGTH:        42 base pairs
        (B) TYPE:          nucleic acid
        (C) STRANDEDNESS:  single
        (D) TOPOLOGY:      linear (xi) SEQUENCE DESCRIPTION: SEQ ID NO:11:

UGAAUAUCAA GCAGGACAUA ACAAGGUAGG AUCUCUACAA UA                           42

(2) INFORMATION FOR SEQ ID NO:12:

(i) SEQUENCE CHARACTERISTICS:
        (A) LENGTH:        44 base pairs
        (B) TYPE:          nucleic acid
        (C) STRANDEDNESS:  single
        (D) TOPOLOGY:      linear (xi) SEQUENCE DESCRIPTION: SEQ ID NO:12:

AUACUUGGCA CUAGCAGCAU UAAUAACACC AAAAAAGAUA AAGC                         44

(2) INFORMATION FOR SEQ ID NO:13:

(i) SEQUENCE CHARACTERISTICS:
        (A) LENGTH:        19 base pairs

```
        (B) TYPE:           nucleic acid
        (C) STRANDEDNESS:   single
        (D) TOPOLOGY:       linear (xi) SEQUENCE DESCRIPTION: SEQ ID NO:13:

CACAAUGAAU GGACACUAG                                                  19

(2) INFORMATION FOR SEQ ID NO:14:

(i) SEQUENCE CHARACTERISTICS:
        (A) LENGTH:         11 base pairs
        (B) TYPE:           nucleic acid
        (C) STRANDEDNESS:   single
        (D) TOPOLOGY:       linear (xi) SEQUENCE DESCRIPTION: SEQ ID NO:14:

AAGCUGUUAG A                                                          11

(2) INFORMATION FOR SEQ ID NO:15:

(i) SEQUENCE CHARACTERISTICS:
        (A) LENGTH:         25 base pairs
        (B) TYPE:           nucleic acid
        (C) STRANDEDNESS:   single
        (D) TOPOLOGY:       linear (xi) SEQUENCE DESCRIPTION: SEQ ID NO:15:

UAGGGCAACA UAUCUAUGAA ACUUA                                           25

(2) INFORMATION FOR SEQ ID NO:16:

(i) SEQUENCE CHARACTERISTICS:
        (A) LENGTH:         13 base pairs
        (B) TYPE:           nucleic acid
        (C) STRANDEDNESS:   single
        (D) TOPOLOGY:       linear (xi) SEQUENCE DESCRIPTION: SEQ ID NO:16:

GCCAUAAUAA GAA                                                        13

(2) INFORMATION FOR SEQ ID NO:17:

(i) SEQUENCE CHARACTERISTICS:
        (A) LENGTH:         11 base pairs
        (B) TYPE:           nucleic acid
        (C) STRANDEDNESS:   single
        (D) TOPOLOGY:       linear (xi) SEQUENCE DESCRIPTION: SEQ ID NO:17:

AUAGGCGUUA C                                                          11

(2) INFORMATION FOR SEQ ID NO:18:

(i) SEQUENCE CHARACTERISTICS:
        (A) LENGTH:         11 base pairs
        (B) TYPE:           nucleic acid
        (C) STRANDEDNESS:   single
        (D) TOPOLOGY:       linear (xi) SEQUENCE DESCRIPTION: SEQ ID NO:18:

GAAAUGGAGC C                                                          11

(2) INFORMATION FOR SEQ ID NO:19:

(i) SEQUENCE CHARACTERISTICS:
        (A) LENGTH:         15 base pairs
        (B) TYPE:           nucleic acid
        (C) STRANDEDNESS:   single
```

(D) TOPOLOGY:     linear (xi) SEQUENCE DESCRIPTION: SEQ ID NO:19:

AUCCUAGACU AGAGC                                                          15

(2) INFORMATION FOR SEQ ID NO:20:

(i) SEQUENCE CHARACTERISTICS:
            (A) LENGTH:       14 base pairs
            (B) TYPE:         nucleic acid
            (C) STRANDEDNESS: single
            (D) TOPOLOGY:     linear (xi) SEQUENCE DESCRIPTION: SEQ ID NO:20:

AAGUCAGCCU AAAA                                                           14

(2) INFORMATION FOR SEQ ID NO:21:

(i) SEQUENCE CHARACTERISTICS:
            (A) LENGTH:       26 base pairs
            (B) TYPE:         nucleic acid
            (C) STRANDEDNESS: single
            (D) TOPOLOGY:     linear (xi) SEQUENCE DESCRIPTION: SEQ ID NO:21:

UGUACCAAUU GCUAUUGUAA AAAGUG                                              26

(2) INFORMATION FOR SEQ ID NO:22:

(i) SEQUENCE CHARACTERISTICS:
            (A) LENGTH:       12 base pairs
            (B) TYPE:         nucleic acid
            (C) STRANDEDNESS: single
            (D) TOPOLOGY:     linear (xi) SEQUENCE DESCRIPTION: SEQ ID NO:22:

UUCAUUGCCA AG                                                             12

(2) INFORMATION FOR SEQ ID NO:23:

(i) SEQUENCE CHARACTERISTICS:
            (A) LENGTH:       44 base pairs
            (B) TYPE:         nucleic acid
            (C) STRANDEDNESS: single
            (D) TOPOLOGY:     linear (xi) SEQUENCE DESCRIPTION: SEQ ID NO:23:

GUUUGUUUCA UAACAAAAGC CUUAGGCAUC UCCUAUGGCA GGAA                           44

(2) INFORMATION FOR SEQ ID NO:24:

(i) SEQUENCE CHARACTERISTICS:
            (A) LENGTH:       15 base pairs
            (B) TYPE:         nucleic acid
            (C) STRANDEDNESS: single
            (D) TOPOLOGY:     linear (xi) SEQUENCE DESCRIPTION: SEQ ID NO:24:

GACAGCGACG AAGAG                                                          15

(2) INFORMATION FOR SEQ ID NO:25:

(i) SEQUENCE CHARACTERISTICS:
            (A) LENGTH:       14 base pairs
            (B) TYPE:         nucleic acid
            (C) STRANDEDNESS: single
            (D) TOPOLOGY:     linear (xi) SEQUENCE DESCRIPTION: SEQ ID NO:25:

AAGACCUCCU CAAG                                                         14

(2) INFORMATION FOR SEQ ID NO:26:

(i) SEQUENCE CHARACTERISTICS:
      (A) LENGTH:        26 base pairs
      (B) TYPE:          nucleic acid
      (C) STRANDEDNESS:  single
      (D) TOPOLOGY:      linear (xi) SEQUENCE DESCRIPTION: SEQ ID NO:26:

GGCAGUCAGA CUCAUCAAGU UUCUCU                                            26

(2) INFORMATION FOR SEQ ID NO:27:

(i) SEQUENCE CHARACTERISTICS:
      (A) LENGTH:        11 base pairs
      (B) TYPE:          nucleic acid
      (C) STRANDEDNESS:  single
      (D) TOPOLOGY:      linear (xi) SEQUENCE DESCRIPTION: SEQ ID NO:27:

AUCAAAGCAA C                                                            11

(2) INFORMATION FOR SEQ ID NO:28:

(i) SEQUENCE CHARACTERISTICS:
      (A) LENGTH:        44 base pairs
      (B) TYPE:          nucleic acid
      (C) STRANDEDNESS:  single
      (D) TOPOLOGY:      linear (xi) SEQUENCE DESCRIPTION: SEQ ID NO:28:

UCCCAAUCCC GAGGGGACCC GACAGGCCCG AAGGAAUAGA AGAA                         44

(2) INFORMATION FOR SEQ ID NO:29:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:29:

CAUUCGAUUA GUGAA                                                        15

(2) INFORMATION FOR SEQ ID NO:30:

(i) SEQUENCE CHARACTERISTICS:
      (A) LENGTH:        22 base pairs
      (B) TYPE:          nucleic acid
      (C) STRANDEDNESS:  single
      (D) TOPOLOGY:      linear (xi) SEQUENCE DESCRIPTION: SEQ ID NO:30:

GGACGAUCUG CGGAGCCUGU GC                                                22

(2) INFORMATION FOR SEQ ID NO:31:

(i) SEQUENCE CHARACTERISTICS:
      (A) LENGTH:        29 base pairs
      (B) TYPE:          nucleic acid
      (C) STRANDEDNESS:  single
      (D) TOPOLOGY:      linear (xi) SEQUENCE DESCRIPTION: SEQ ID NO:31:

GGGAAGCCCU CAAAUAUUGG UGGAAUCUC                                  29

(2) INFORMATION FOR SEQ ID NO:32:

(i) SEQUENCE CHARACTERISTICS:
        (A) LENGTH:          12 base pairs
        (B) TYPE:            nucleic acid
        (C) STRANDEDNESS:    single
        (D) TOPOLOGY:        linear (xi) SEQUENCE DESCRIPTION: SEQ ID NO:32:

AGAAUAGUGC UG                                                    12

(2) INFORMATION FOR SEQ ID NO:33:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO:33:

UGCCACAGCU AUAGCA                                                16

(2) INFORMATION FOR SEQ ID NO:34:

(i) SEQUENCE CHARACTERISTICS:
        (A) LENGTH:          23 base pairs
        (B) TYPE:            nucleic acid
        (C) STRANDEDNESS:    single
        (D) TOPOLOGY:        linear (xi) SEQUENCE DESCRIPTION: SEQ ID NO:34:

AAGUAGUACA AGAAGCUUAU AGA                                        23

(2) INFORMATION FOR SEQ ID NO:35:

(i) SEQUENCE CHARACTERISTICS:
        (A) LENGTH:          34 base pairs
        (B) TYPE:            nucleic acid
        (C) STRANDEDNESS:    single
        (D) TOPOLOGY:        linear (xi) SEQUENCE DESCRIPTION: SEQ ID NO:35:

UACCUAGAAG AAUAAGACAG GGCUUGGAAA GGAU                            34

(2) INFORMATION FOR SEQ ID NO:36:

(i) SEQUENCE CHARACTERISTICS:
        (A) LENGTH:          14 base pairs
        (B) TYPE:            nucleic acid
        (C) STRANDEDNESS:    single
        (D) TOPOLOGY:        linear (xi) SEQUENCE DESCRIPTION: SEQ ID NO:36:

UGGUCAAAAA GUAG                                                  14

(2) INFORMATION FOR SEQ ID NO:37:

(i) SEQUENCE CHARACTERISTICS:
        (A) LENGTH:          22 base pairs
        (B) TYPE:            nucleic acid
        (C) STRANDEDNESS:    single
        (D) TOPOLOGY:        linear (xi) SEQUENCE DESCRIPTION: SEQ ID NO:37:

AAGAAUGAGA CGAGCUGAGC CA                                         22

(2) INFORMATION FOR SEQ ID NO:38:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:38:

GGAGCAGUAU CUCGA  15

(2) INFORMATION FOR SEQ ID NO:39:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:39:

AGACCUAGAA AAACAUGGAG CAAUCACA  28

(2) INFORMATION FOR SEQ ID NO:40:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:40:

CCUGGCUAGA AGCACAAGAG GAGGAGAAGG UGGG  34

(2) INFORMATION FOR SEQ ID NO:41:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:41:

ACACCUCAGG UACCUUUAAG ACCAAUGACU UACAAG  36

(2) INFORMATION FOR SEQ ID NO:42:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:42:

GCAGCUGUAG AUCUUAGCCA CUUUUUAAAA GAAAAGGGGG  40

(2) INFORMATION FOR SEQ ID NO:43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:43:

GGGGGACUGG AAGGG  15

(2) INFORMATION FOR SEQ ID NO:44:

```
    (i) SEQUENCE CHARACTERISTICS:
        (A) LENGTH:        19 base pairs
        (B) TYPE:          nucleic acid
        (C) STRANDEDNESS:  single
        (D) TOPOLOGY:      linear (xi) SEQUENCE DESCRIPTION: SEQ ID NO:44:

GCUAAUUCAC UCCCAACGA                                                    19

(2) INFORMATION FOR SEQ ID NO:45:

(i) SEQUENCE CHARACTERISTICS:
        (A) LENGTH:        34 base pairs
        (B) TYPE:          nucleic acid
        (C) STRANDEDNESS:  single
        (D) TOPOLOGY:      linear (xi) SEQUENCE DESCRIPTION: SEQ ID NO:45:

AGACAAGAUA UCCUUGAUCU GUGGAUCUAC CACA                                   34

(2) INFORMATION FOR SEQ ID NO:46:

(i) SEQUENCE CHARACTERISTICS:
        (A) LENGTH:        24 base pairs
        (B) TYPE:          nucleic acid
        (C) STRANDEDNESS:  single
        (D) TOPOLOGY:      linear (xi) SEQUENCE DESCRIPTION: SEQ ID NO:46:

AUUGGCAGAA CUACACACCA GGAC                                              24

(2) INFORMATION FOR SEQ ID NO:47:

(i) SEQUENCE CHARACTERISTICS:
        (A) LENGTH:        11 base pairs
        (B) TYPE:          nucleic acid
        (C) STRANDEDNESS:  single
        (D) TOPOLOGY:      linear (xi) SEQUENCE DESCRIPTION: SEQ ID NO:47:

UCAGAUAUCC A                                                            11

(2) INFORMATION FOR SEQ ID NO:48:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:48:

AAGCUAGUAC CAGUU                                                        15

(2) INFORMATION FOR SEQ ID NO:49:

(i) SEQUENCE CHARACTERISTICS:
        (A) LENGTH:        14 base pairs
        (B) TYPE:          nucleic acid
        (C) STRANDEDNESS:  single
        (D) TOPOLOGY:      linear (xi) SEQUENCE DESCRIPTION: SEQ ID NO:49:

GAGAACACCA GCUU                                                         14

(2) INFORMATION FOR SEQ ID NO:50:

(i) SEQUENCE CHARACTERISTICS:
```

```
        (A) LENGTH:          29 base pairs
        (B) TYPE:            nucleic acid
        (C) STRANDEDNESS:    single
        (D) TOPOLOGY:        linear (xi) SEQUENCE DESCRIPTION: SEQ ID NO:50:

ACCCUGUGAG CCUGCAUGGA AUGGAUGAC                                          29

(2) INFORMATION FOR SEQ ID NO:51:

(i) SEQUENCE CHARACTERISTICS:
        (A) LENGTH:          20 base pairs
        (B) TYPE:            nucleic acid
        (C) STRANDEDNESS:    single
        (D) TOPOLOGY:        linear (xi) SEQUENCE DESCRIPTION: SEQ ID NO:51:

AGUGGAGGUU UGACAGCCGC                                                    20

(2) INFORMATION FOR SEQ ID NO:52:

(i) SEQUENCE CHARACTERISTICS:
        (A) LENGTH:          42 base pairs
        (B) TYPE:            nucleic acid
        (C) STRANDEDNESS:    single
        (D) TOPOLOGY:        linear (xi) SEQUENCE DESCRIPTION: SEQ ID NO:52:

AGUACUUCAA GAACUGCUGA UAUCGAGCUU GCUACAAGGG AC                            42

(2) INFORMATION FOR SEQ ID NO:53:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO:53:

CUGCUUUUUG CCUGUAC                                                       17

(2) INFORMATION FOR SEQ ID NO:54:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO:54:

UCUGAGCCUG GGAGCUC                                                       17

(2) INFORMATION FOR SEQ ID NO:55:

(i) SEQUENCE CHARACTERISTICS:
        (A) LENGTH:          11 base pairs
        (B) TYPE:            nucleic acid
        (C) STRANDEDNESS:    single
        (D) TOPOLOGY:        linear (xi) SEQUENCE DESCRIPTION: SEQ ID NO:55:

UAAAGCUUGC C                                                             11

(2) INFORMATION FOR SEQ ID NO:56:

(i) SEQUENCE CHARACTERISTICS:
        (A) LENGTH:          18 base pairs
        (B) TYPE:            nucleic acid
```

(C) STRANDEDNESS:    single
            (D) TOPOLOGY:        linear (xi) SEQUENCE DESCRIPTION: SEQ ID NO:56:

UGCCUGUAGA UCCUAGAC                                                        18

(2) INFORMATION FOR SEQ ID NO:57:

(i) SEQUENCE CHARACTERISTICS:
            (A) LENGTH:          19 base pairs
            (B) TYPE:            nucleic acid
            (C) STRANDEDNESS:    single
            (D) TOPOLOGY:        linear (xi) SEQUENCE DESCRIPTION: SEQ ID NO:57:

AGCAUCCAGG AAGUCAGCC                                                       19

(2) INFORMATION FOR SEQ ID NO:58:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any
                base.

(xi) SEQUENCE DESCRIPTION: SEQ ID NO:58:

CAAGUGGUCA AAANG                                                           15

(2) INFORMATION FOR SEQ ID NO:59:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (ix) FEATURE:
            (D) OTHER INFORMATION:   The letter "R" stands for G or A.

(xi) SEQUENCE DESCRIPTION: SEQ ID NO:59:

GGAGCAGUAU CUCRA                                                           15

(2) INFORMATION FOR SEQ ID NO:60:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any
                base.

(xi) SEQUENCE DESCRIPTION: SEQ ID NO:60:

CCNCAGGUAC CUUUA                                                           15

(2) INFORMATION FOR SEQ ID NO:61:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (ix) FEATURE:

(D) OTHER INFORMATION: The letter "W" stands for A or U.

(xi) SEQUENCE DESCRIPTION: SEQ ID NO:61:

GGGGGACUGG AWGGG                                                              15

(2) INFORMATION FOR SEQ ID NO:62:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (ix) FEATURE:
            (D) OTHER INFORMATION: The letter "R" stands for A or G.

(xi) SEQUENCE DESCRIPTION: SEQ ID NO:62:

CCAUAUGUAU RUUUC                                                              15

(2) INFORMATION FOR SEQ ID NO:63:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (ix) FEATURE:
            (D) OTHER INFORMATION: The letter "Y" stands for U or C.
                The letter "R" stands for G or A.
                The letter "N" stands for any
                base.

(xi) SEQUENCE DESCRIPTION: SEQ ID NO:63:

AGAYUGGUAR UAANA                                                              15

(2) INFORMATION FOR SEQ ID NO:64:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:64:

AUCUGGGUCA GGGAG                                                              15

(2) INFORMATION FOR SEQ ID NO:65:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:65:

AUUUGGGUCA GGGAG                                                              15

(2) INFORMATION FOR SEQ ID NO:66:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:66:

CAGGGAGUCU CCAUA                                                              15

(2) INFORMATION FOR SEQ ID NO:67:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:67:

ACACAAGUAG ACCCU                                                      15

(2) INFORMATION FOR SEQ ID NO:68:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:68:

AACAAGGUAG GAUCU                                                      15

(2) INFORMATION FOR SEQ ID NO:69:

(i) SEQUENCE CHARACTERISTICS:
        (A) LENGTH:       56 base pairs
        (B) TYPE:         nucleic acid
        (C) STRANDEDNESS:  single
        (D) TOPOLOGY:     linear (xi) SEQUENCE DESCRIPTION: SEQ ID NO:69:

CACCAUCCAA AGAGAAGUGG ACCAGAGAAA CACACGUUGU GGUACAUUAC CUGGUA        56

(2) INFORMATION FOR SEQ ID NO:70:

(i) SEQUENCE CHARACTERISTICS:
        (A) LENGTH:       56 base pairs
        (B) TYPE:         nucleic acid
        (C) STRANDEDNESS:  single
        (D) TOPOLOGY:     linear (xi) SEQUENCE DESCRIPTION: SEQ ID NO:70:

UAUUGAGGCU UAAAGAGUGG ACCAGAGAAA CACACGUUGU GGUACAUUAC CUGGUA        56

(2) INFORMATION FOR SEQ ID NO:71:

(i) SEQUENCE CHARACTERISTICS:
        (A) LENGTH:       56 base pairs
        (B) TYPE:         nucleic acid
        (C) STRANDEDNESS:  single
        (D) TOPOLOGY:     linear (xi) SEQUENCE DESCRIPTION: SEQ ID NO:71:

AGUCACACAA CAAGAAGGCA ACCAGAGAAA CACACGUUGU GGUACAUUAC CUGGUA        56

(2) INFORMATION FOR SEQ ID NO:72:

(i) SEQUENCE CHARACTERISTICS:
        (A) LENGTH:       58 base pairs
        (B) TYPE:         nucleic acid
        (C) STRANDEDNESS:  single
        (D) TOPOLOGY:     linear (xi) SEQUENCE DESCRIPTION: SEQ ID NO:72:

AGUCACACAA CAAGAAGGCA CAACCAGAGA AACACACGUU GUGGUACAUU ACCUGGUA      58

(2) INFORMATION FOR SEQ ID NO:73:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:73:

UUCCACAUUU CCAAGAGCCC ACCAGAGAAA CACACGUUGU GGUACAUUAC CUGGUA          56

(2) INFORMATION FOR SEQ ID NO:74:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:74:

GCCAUAUUCC UGAGAAGCAG ACCAGAGAAA CACACGUUGU GGUACAUUAC CUGGUA          56

(2) INFORMATION FOR SEQ ID NO:75:

(i) SEQUENCE CHARACTERISTICS:
        (A) LENGTH:         58 base pairs
        (B) TYPE:           nucleic acid
        (C) STRANDEDNESS:   single
        (D) TOPOLOGY:       linear (xi) SEQUENCE DESCRIPTION: SEQ ID NO:75:

GCCAUAUUCC UGAGAAGCAG UCACCAGAGA AACACACGUU GUGGUACAUU ACCUGGUA        58

(2) INFORMATION FOR SEQ ID NO:76:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:76:

CACCAUCCAA AGAGAAGUGG ACCAGAGAAA CACACGUUGU GGUACAUUAC CUGGUA          56

(2) INFORMATION FOR SEQ ID NO:77:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:77:

UAUUGAGGCU UAAAGAGUGG ACCAGAGAAA CACACGUUGU GGUACAUUAC CUGGUA          56

(2) INFORMATION FOR SEQ ID NO:78:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:78:

AGUCACACAA CAAGAAGGCA ACCAGAGAAA CACACGUUGU GGUACAUUAC CUGGUA          56

(2) INFORMATION FOR SEQ ID NO:79:

(i) SEQUENCE CHARACTERISTICS:

```
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:79:

CCACUGACCU UUGGAUGGUG                                                      20

(2) INFORMATION FOR SEQ ID NO:80:

(i) SEQUENCE CHARACTERISTICS:
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:80:

CCACUGCUUA AGCCUCAAUA                                                      20

(2) INFORMATION FOR SEQ ID NO:81:

(i) SEQUENCE CHARACTERISTICS:
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:81:

UGCCCGUCUG UUGUGUGACU                                                      20

(2) INFORMATION FOR SEQ ID NO:82:

(i) SEQUENCE CHARACTERISTICS:
          (A) LENGTH:          22 base pairs
          (B) TYPE:            nucleic acid
          (C) STRANDEDNESS:    single
          (D) TOPOLOGY:        linear (xi) SEQUENCE DESCRIPTION: SEQ ID NO:82:

UGUGCCCGUC UGUUGUGUGA CU                                                   22

(2) INFORMATION FOR SEQ ID NO:83:

(i) SEQUENCE CHARACTERISTICS:
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:83:

GGGCUGUUGG AAAUGUGGAA                                                      20

(2) INFORMATION FOR SEQ ID NO:84:

(i) SEQUENCE CHARACTERISTICS:
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:84:

CUGUAGUCCA GGAAUAUGGC                                                      20

(2) INFORMATION FOR SEQ ID NO:85:

(i) SEQUENCE CHARACTERISTICS:
          (A) LENGTH:          22 base pairs
          (B) TYPE:            nucleic acid
```

```
          (C) STRANDEDNESS:    single
          (D) TOPOLOGY:        linear (xi) SEQUENCE DESCRIPTION: SEQ ID NO:85:

GACUGUAGUC CAGGAAUAUG GC                                              22

(2) INFORMATION FOR SEQ ID NO:86:

(i) SEQUENCE CHARACTERISTICS:
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:86:

CCACUGACCU UUGGAUGGUG                                                 20

(2) INFORMATION FOR SEQ ID NO:87:

(i) SEQUENCE CHARACTERISTICS:
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:87:

CCACUGCUUA AGCCUCAAUA                                                 20

(2) INFORMATION FOR SEQ ID NO:88:

(i) SEQUENCE CHARACTERISTICS:
          (A) LENGTH:          20 base pairs
          (B) TYPE:            nucleic acid
          (C) STRANDEDNESS:    single
          (D) TOPOLOGY:        linear (xi) SEQUENCE DESCRIPTION: SEQ ID NO:88:

UGCCCGUCUG UUGUGUGACU                                                 20

(2) INFORMATION FOR SEQ ID NO:89:

(i) SEQUENCE CHARACTERISTICS:
          (A) LENGTH:          46 base pairs
          (B) TYPE:            nucleic acid
          (C) STRANDEDNESS:    single
          (D) TOPOLOGY:        linear (xi) SEQUENCE DESCRIPTION: SEQ ID NO:89:

UUUAUUGAGG CUCUGAUGAG GCCGAAAGGC CGAAAAGCAG UGGGUU                    46

(2) INFORMATION FOR SEQ ID NO:90:

(i) SEQUENCE CHARACTERISTICS:
          (A) LENGTH:          46 base pairs
          (B) TYPE:            nucleic acid
          (C) STRANDEDNESS:    single
          (D) TOPOLOGY:        linear (xi) SEQUENCE DESCRIPTION: SEQ ID NO:90:

GCAAGCUUUA UUCUGAUGAG GCCGAAAGGC CGAAAGGCUU AAGCAG                    46

(2) INFORMATION FOR SEQ ID NO:91:

(i) SEQUENCE CHARACTERISTICS:
          (A) LENGTH:          46 base pairs
          (B) TYPE:            nucleic acid
          (C) STRANDEDNESS:    single
          (D) TOPOLOGY:        linear
```

(xi) SEQUENCE DESCRIPTION: SEQ ID NO:91:

CAAGGCAAGC UUCUGAUGAG GCCGAAAGGC CGAAAUUGAG GCUUAA                                46

(2) INFORMATION FOR SEQ ID NO:92:

(i) SEQUENCE CHARACTERISTICS:
        (A) LENGTH:        46 base pairs
        (B) TYPE:          nucleic acid
        (C) STRANDEDNESS:  single
        (D) TOPOLOGY:      linear (xi) SEQUENCE DESCRIPTION: SEQ ID NO:92:

CUUGAAGCAC UCCUGAUGAG GCCGAAAGGC CGAAAGGCAA GCUUUA                                46

(2) INFORMATION FOR SEQ ID NO:93:

(i) SEQUENCE CHARACTERISTICS:
        (A) LENGTH:        46 base pairs
        (B) TYPE:          nucleic acid
        (C) STRANDEDNESS:  single
        (D) TOPOLOGY:      linear (xi) SEQUENCE DESCRIPTION: SEQ ID NO:93:

ACGGGCACAC ACCUGAUGAG GCCGAAAGGC CGAAACUUGA AGCACU                                46

(2) INFORMATION FOR SEQ ID NO:94:

(i) SEQUENCE CHARACTERISTICS:
        (A) LENGTH:        46 base pairs
        (B) TYPE:          nucleic acid
        (C) STRANDEDNESS:  single
        (D) TOPOLOGY:      linear (xi) SEQUENCE DESCRIPTION: SEQ ID NO:94:

AGUCACACAA CACUGAUGAG GCCGAAAGGC CGAAACGGGC ACACAC                                46

(2) INFORMATION FOR SEQ ID NO:95:

(i) SEQUENCE CHARACTERISTICS:
        (A) LENGTH:        46 base pairs
        (B) TYPE:          nucleic acid
        (C) STRANDEDNESS:  single
        (D) TOPOLOGY:      linear (xi) SEQUENCE DESCRIPTION: SEQ ID NO:95:

CUCUAGUUAC CACUGAUGAG GCCGAAAGGC CGAAAGUCAC ACAACA                                46

(2) INFORMATION FOR SEQ ID NO:96:

(i) SEQUENCE CHARACTERISTICS:
        (A) LENGTH:        46 base pairs
        (B) TYPE:          nucleic acid
        (C) STRANDEDNESS:  single
        (D) TOPOLOGY:      linear (xi) SEQUENCE DESCRIPTION: SEQ ID NO:96:

AAGGGUCUGA GGCUGAUGAG GCCGAAAGGC CGAAAUCUCU AGUUAC                                46

(2) INFORMATION FOR SEQ ID NO:97:

(i) SEQUENCE CHARACTERISTICS:
        (A) LENGTH:        46 base pairs
        (B) TYPE:          nucleic acid
        (C) STRANDEDNESS:  single
        (D) TOPOLOGY:      linear (xi) SEQUENCE DESCRIPTION: SEQ ID NO:97:

CCACACUGAC UACUGAUGAG GCCGAAAGGC CGAAAAGGGU CUGAGG        46

(2) INFORMATION FOR SEQ ID NO:98:

(i) SEQUENCE CHARACTERISTICS:
       (A) LENGTH:         46 base pairs
       (B) TYPE:           nucleic acid
       (C) STRANDEDNESS:   single
       (D) TOPOLOGY:       linear (xi) SEQUENCE DESCRIPTION: SEQ ID NO:98:

GGGCGCCACU GCCUGAUGAG GCCGAAAGGC CGAAAGAGAU UUUCCA        46

(2) INFORMATION FOR SEQ ID NO:99:

(i) SEQUENCE CHARACTERISTICS:
       (A) LENGTH:         46 base pairs
       (B) TYPE:           nucleic acid
       (C) STRANDEDNESS:   single
       (D) TOPOLOGY:       linear (xi) SEQUENCE DESCRIPTION: SEQ ID NO:99:

CUUCAGCAAG CCCUGAUGAG GCCGAAAGGC CGAAAGUCCU GCGUCG        46

(2) INFORMATION FOR SEQ ID NO:100:

(i) SEQUENCE CHARACTERISTICS:
       (A) LENGTH:         46 base pairs
       (B) TYPE:           nucleic acid
       (C) STRANDEDNESS:   single
       (D) TOPOLOGY:       linear (xi) SEQUENCE DESCRIPTION: SEQ ID NO:100:

CCGCUUAAUA CUCUGAUGAG GCCGAAAGGC CGAAACGCUC UCGCAC        46

(2) INFORMATION FOR SEQ ID NO:101:

(i) SEQUENCE CHARACTERISTICS:
       (A) LENGTH:         46 base pairs
       (B) TYPE:           nucleic acid
       (C) STRANDEDNESS:   single
       (D) TOPOLOGY:       linear (xi) SEQUENCE DESCRIPTION: SEQ ID NO:101:

UUCCACAUUU CCCUGAUGAG GCCGAAAGGC CGAAACAGCC CUUUUU        46

(2) INFORMATION FOR SEQ ID NO:102:

(i) SEQUENCE CHARACTERISTICS:
       (A) LENGTH:         46 base pairs
       (B) TYPE:           nucleic acid
       (C) STRANDEDNESS:   single
       (D) TOPOLOGY:       linear (xi) SEQUENCE DESCRIPTION: SEQ ID NO:102:

AUAUUCCUGG ACCUGAUGAG GCCGAAAGGC CGAAACAGUC UACUUG        46

(2) INFORMATION FOR SEQ ID NO:103:

(i) SEQUENCE CHARACTERISTICS:
       (A) LENGTH:         46 base pairs
       (B) TYPE:           nucleic acid
       (C) STRANDEDNESS:   single
       (D) TOPOLOGY:       linear (xi) SEQUENCE DESCRIPTION: SEQ ID NO:103:

UAGUCUAGGA UCCUGAUGAG GCCGAAAGGC CGAAACUGGC UCCAUU        46

(2) INFORMATION FOR SEQ ID NO:104:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:104:

GCUGACUUCC UGCUGAUGAG GCCGAAAGGC CGAAAUGCUU CCAGGG      46

(2) INFORMATION FOR SEQ ID NO:105:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:105:

CAGUUUUAGG CUCUGAUGAG GCCGAAAGGC CGAAACUUCC UGGAUG      46

(2) INFORMATION FOR SEQ ID NO:106:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:106:

AACACUUUUU ACCUGAUGAG GCCGAAAGGC CGAAAUAGCA AUUGGU      46

(2) INFORMATION FOR SEQ ID NO:107:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:107:

AGCAACACUU UUCUGAUGAG GCCGAAAGGC CGAAACAAUA GCAAUU      46

(2) INFORMATION FOR SEQ ID NO:108:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:108:

GGCAAUGAAA GCCUGAUGAG GCCGAAAGGC CGAAACACUU UUUACA      46

(2) INFORMATION FOR SEQ ID NO:109:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:109:

CCUGCCAUAG GACUGAUGAG GCCGAAAGGC CGAAAUGCCU AAGGCU      46

(2) INFORMATION FOR SEQ ID NO:110:

(i) SEQUENCE CHARACTERISTICS:
        (A) LENGTH:      46 base pairs
        (B) TYPE:        nucleic acid
        (C) STRANDEDNESS: single
        (D) TOPOLOGY:    linear (xi) SEQUENCE DESCRIPTION: SEQ ID NO:110:

UUCCUGCCAU AGCUGAUGAG GCCGAAAGGC CGAAAGAUGC CUAAGG          46

(2) INFORMATION FOR SEQ ID NO:111:

(i) SEQUENCE CHARACTERISTICS:
        (A) LENGTH:      46 base pairs
        (B) TYPE:        nucleic acid
        (C) STRANDEDNESS: single
        (D) TOPOLOGY:    linear (xi) SEQUENCE DESCRIPTION: SEQ ID NO:111:

UUCUUCCUGC CACUGAUGAG GCCGAAAGGC CGAAAGGAGA UGCCUA          46

(2) INFORMATION FOR SEQ ID NO:112:

(i) SEQUENCE CHARACTERISTICS:
        (A) LENGTH:      46 base pairs
        (B) TYPE:        nucleic acid
        (C) STRANDEDNESS: single
        (D) TOPOLOGY:    linear (xi) SEQUENCE DESCRIPTION: SEQ ID NO:112:

UUUAUUGAGG CUCUGAUGAG GCCGAAAGGC CGAAAAGCAG UGGGUU          46

(2) INFORMATION FOR SEQ ID NO:113:

(i) SEQUENCE CHARACTERISTICS:
        (A) LENGTH:      46 base pairs
        (B) TYPE:        nucleic acid
        (C) STRANDEDNESS: single
        (D) TOPOLOGY:    linear (xi) SEQUENCE DESCRIPTION: SEQ ID NO:113:

GCAAGCUUUA UUCUGAUGAG GCCGAAAGGC CGAAAGGCUU AAGCAG          46

(2) INFORMATION FOR SEQ ID NO:114:

(i) SEQUENCE CHARACTERISTICS:
        (A) LENGTH:      46 base pairs
        (B) TYPE:        nucleic acid
        (C) STRANDEDNESS: single
        (D) TOPOLOGY:    linear (xi) SEQUENCE DESCRIPTION: SEQ ID NO:114:

CAAGGCAAGC UUCUGAUGAG GCCGAAAGGC CGAAAUUGAG GCUUAA          46

(2) INFORMATION FOR SEQ ID NO:115:

(i) SEQUENCE CHARACTERISTICS:
        (A) LENGTH:      46 base pairs
        (B) TYPE:        nucleic acid
        (C) STRANDEDNESS: single
        (D) TOPOLOGY:    linear (xi) SEQUENCE DESCRIPTION: SEQ ID NO:115:

CUUGAAGCAC UCCUGAUGAG GCCGAAAGGC CGAAAGGCAA GCUUUA          46

(2) INFORMATION FOR SEQ ID NO:116:

(i) SEQUENCE CHARACTERISTICS:
    (A) LENGTH:         46 base pairs
    (B) TYPE:           nucleic acid
    (C) STRANDEDNESS:   single
    (D) TOPOLOGY:       linear (xi) SEQUENCE DESCRIPTION: SEQ ID NO:116:

ACGGGCACAC ACCUGAUGAG GCCGAAAGGC CGAAACUUGA AGCACU          46

(2) INFORMATION FOR SEQ ID NO:117:

(i) SEQUENCE CHARACTERISTICS:
        (A) LENGTH:         46 base pairs
        (B) TYPE:           nucleic acid
        (C) STRANDEDNESS:   single
        (D) TOPOLOGY:       linear (xi) SEQUENCE DESCRIPTION: SEQ ID NO:117:

AGUCACACAA CACUGAUGAG GCCGAAAGGC CGAAACGGGC ACACAC          46

(2) INFORMATION FOR SEQ ID NO:118:

(i) SEQUENCE CHARACTERISTICS:
        (A) LENGTH:         46 base pairs
        (B) TYPE:           nucleic acid
        (C) STRANDEDNESS:   single
        (D) TOPOLOGY:       linear (xi) SEQUENCE DESCRIPTION: SEQ ID NO:118:

CUCUAGUUAC CACUGAUGAG GCCGAAAGGC CGAAAGUCAC ACAACA          46

(2) INFORMATION FOR SEQ ID NO:119:

(i) SEQUENCE CHARACTERISTICS:
        (A) LENGTH:         46 base pairs
        (B) TYPE:           nucleic acid
        (C) STRANDEDNESS:   single
        (D) TOPOLOGY:       linear (xi) SEQUENCE DESCRIPTION: SEQ ID NO:119:

AAGGGUCUGA GGCUGAUGAG GCCGAAAGGC CGAAAUCUCU AGUUAC          46

(2) INFORMATION FOR SEQ ID NO:120:

(i) SEQUENCE CHARACTERISTICS:
        (A) LENGTH:         46 base pairs
        (B) TYPE:           nucleic acid
        (C) STRANDEDNESS:   single
        (D) TOPOLOGY:       linear (xi) SEQUENCE DESCRIPTION: SEQ ID NO:120:

CCACACUGAC UACUGAUGAG GCCGAAAGGC CGAAAAGGGU CUGAGG          46

(2) INFORMATION FOR SEQ ID NO:121:

(i) SEQUENCE CHARACTERISTICS:
        (A) LENGTH:         25 base pairs
        (B) TYPE:           nucleic acid
        (C) STRANDEDNESS:   single
        (D) TOPOLOGY:       linear (xi) SEQUENCE DESCRIPTION: SEQ ID NO:121:

AACCCACUGC UUAAGCCUCA AUAAA                                 25

(2) INFORMATION FOR SEQ ID NO:122:

(i) SEQUENCE CHARACTERISTICS:
        (A) LENGTH:         25 base pairs (B) TYPE:          nucleic acid
              (C) STRANDEDNESS:  single
              (D) TOPOLOGY:      linear (xi) SEQUENCE DESCRIPTION: SEQ ID NO:122:

CUGCUUAAGC CUCAAUAAAG CUUGC                                                 25

(2) INFORMATION FOR SEQ ID NO:123:

(i) SEQUENCE CHARACTERISTICS:
              (A) LENGTH:        25 base pairs
              (B) TYPE:          nucleic acid
              (C) STRANDEDNESS:  single
              (D) TOPOLOGY:      linear (xi) SEQUENCE DESCRIPTION: SEQ ID NO:123:

UUAAGCCUCA AUAAAGCUUG CCUUG                                                 25

(2) INFORMATION FOR SEQ ID NO:124:

(i) SEQUENCE CHARACTERISTICS:
              (A) LENGTH:        25 base pairs
              (B) TYPE:          nucleic acid
              (C) STRANDEDNESS:  single
              (D) TOPOLOGY:      linear (xi) SEQUENCE DESCRIPTION: SEQ ID NO:124:

UAAAGCUUGC CUUGAGUGCU UCAAG                                                 25

(2) INFORMATION FOR SEQ ID NO:125:

(i) SEQUENCE CHARACTERISTICS:
              (A) LENGTH:        25 base pairs
              (B) TYPE:          nucleic acid
              (C) STRANDEDNESS:  single
              (D) TOPOLOGY:      linear (xi) SEQUENCE DESCRIPTION: SEQ ID NO:125:

AGUGCUUCAA GUAGUGUGUG CCCGU                                                 25

(2) INFORMATION FOR SEQ ID NO:126:

(i) SEQUENCE CHARACTERISTICS:
              (A) LENGTH:        25 base pairs
              (B) TYPE:          nucleic acid
              (C) STRANDEDNESS:  single
              (D) TOPOLOGY:      linear (xi) SEQUENCE DESCRIPTION: SEQ ID NO:126:

GUGUGUGCCC GUCUGUUGUG UGACU                                                 25

(2) INFORMATION FOR SEQ ID NO:127:

(i) SEQUENCE CHARACTERISTICS:
              (A) LENGTH:        25 base pairs
              (B) TYPE:          nucleic acid
              (C) STRANDEDNESS:  single
              (D) TOPOLOGY:      linear (xi) SEQUENCE DESCRIPTION: SEQ ID NO:127:

UGUUGUGUGA CUCUGGUAAC UAGAG                                                 25

(2) INFORMATION FOR SEQ ID NO:128:

(i) SEQUENCE CHARACTERISTICS:
              (A) LENGTH:        25 base pairs
              (B) TYPE:          nucleic acid
              (C) STRANDEDNESS:  single (D) TOPOLOGY:      linear (xi) SEQUENCE DESCRIPTION: SEQ ID NO:128:

GUAACUAGAG AUCCCUCAGA CCCUU                                                25

(2) INFORMATION FOR SEQ ID NO:129:

(i) SEQUENCE CHARACTERISTICS:
            (A) LENGTH:        25 base pairs
            (B) TYPE:          nucleic acid
            (C) STRANDEDNESS:  single
            (D) TOPOLOGY:      linear (xi) SEQUENCE DESCRIPTION: SEQ ID NO:129:

CCUCAGACCC UUUUAGUCAG UGUGG                                                25

(2) INFORMATION FOR SEQ ID NO:130:

(i) SEQUENCE CHARACTERISTICS:
            (A) LENGTH:        25 base pairs
            (B) TYPE:          nucleic acid
            (C) STRANDEDNESS:  single
            (D) TOPOLOGY:      linear (xi) SEQUENCE DESCRIPTION: SEQ ID NO:130:

UGGAAAAUCU CUAGCAGUGG CGCCC                                                25

(2) INFORMATION FOR SEQ ID NO:131:

(i) SEQUENCE CHARACTERISTICS:
            (A) LENGTH:        25 base pairs
            (B) TYPE:          nucleic acid
            (C) STRANDEDNESS:  single
            (D) TOPOLOGY:      linear (xi) SEQUENCE DESCRIPTION: SEQ ID NO:131:

CGACGCAGGA CUCGGCUUGC UGAAG                                                25

(2) INFORMATION FOR SEQ ID NO:132:

(i) SEQUENCE CHARACTERISTICS:
            (A) LENGTH:        25 base pairs
            (B) TYPE:          nucleic acid
            (C) STRANDEDNESS:  single
            (D) TOPOLOGY:      linear (xi) SEQUENCE DESCRIPTION: SEQ ID NO:132:

GUGCGAGAGC GUCAGUAUUA AGCGG                                                25

(2) INFORMATION FOR SEQ ID NO:133:

(i) SEQUENCE CHARACTERISTICS:
            (A) LENGTH:        25 base pairs
            (B) TYPE:          nucleic acid
            (C) STRANDEDNESS:  single
            (D) TOPOLOGY:      linear (xi) SEQUENCE DESCRIPTION: SEQ ID NO:133:

AAAAAGGGCU GUUGGAAAUG UGGAA                                                25

(2) INFORMATION FOR SEQ ID NO:134:

(i) SEQUENCE CHARACTERISTICS:
            (A) LENGTH:        25 base pairs
            (B) TYPE:          nucleic acid
            (C) STRANDEDNESS:  single
            (D) TOPOLOGY:      linear (xi) SEQUENCE DESCRIPTION: SEQ ID NO:134:

CAAGUAGACU GUAGUCCAGG AAUAU                                              25

(2) INFORMATION FOR SEQ ID NO:135:

(i) SEQUENCE CHARACTERISTICS:
              (A) LENGTH:         25 base pairs
              (B) TYPE:           nucleic acid
              (C) STRANDEDNESS:   single
              (D) TOPOLOGY:       linear (xi) SEQUENCE DESCRIPTION: SEQ ID NO:135:

AAUGGAGCCA GUAGAUCCUA GACUA                                              25

(2) INFORMATION FOR SEQ ID NO:136:

(i) SEQUENCE CHARACTERISTICS:
              (A) LENGTH:         25 base pairs
              (B) TYPE:           nucleic acid
              (C) STRANDEDNESS:   single
              (D) TOPOLOGY:       linear (xi) SEQUENCE DESCRIPTION: SEQ ID NO:136:

CCCUGGAAGC AUCCAGGAAG UCAGC                                              25

(2) INFORMATION FOR SEQ ID NO:137:

(i) SEQUENCE CHARACTERISTICS:
              (A) LENGTH:         25 base pairs
              (B) TYPE:           nucleic acid
              (C) STRANDEDNESS:   single
              (D) TOPOLOGY:       linear (xi) SEQUENCE DESCRIPTION: SEQ ID NO:137:

CAUCCAGGAA GUCAGCCUAA AACUG                                              25

(2) INFORMATION FOR SEQ ID NO:138:

(i) SEQUENCE CHARACTERISTICS:
              (A) LENGTH:         25 base pairs
              (B) TYPE:           nucleic acid
              (C) STRANDEDNESS:   single
              (D) TOPOLOGY:       linear (xi) SEQUENCE DESCRIPTION: SEQ ID NO:138:

ACCAAUUGCU AUUGUAAAAA GUGUU                                              25

(2) INFORMATION FOR SEQ ID NO:139:

(i) SEQUENCE CHARACTERISTICS:
              (A) LENGTH:         25 base pairs
              (B) TYPE:           nucleic acid
              (C) STRANDEDNESS:   single
              (D) TOPOLOGY:       linear (xi) SEQUENCE DESCRIPTION: SEQ ID NO:139:

AAUUGCUAUU GUAAAAGUG UUGCU                                               25

(2) INFORMATION FOR SEQ ID NO:140:

(i) SEQUENCE CHARACTERISTICS:
              (A) LENGTH:         25 base pairs
              (B) TYPE:           nucleic acid
              (C) STRANDEDNESS:   single
              (D) TOPOLOGY:       linear (xi) SEQUENCE DESCRIPTION: SEQ ID NO:140:

UGUAAAAAGU GUUGCUUUCA UUGCC                                              25

(2) INFORMATION FOR SEQ ID NO:141:

(i) SEQUENCE CHARACTERISTICS:
        (A) LENGTH:        25 base pairs
        (B) TYPE:          nucleic acid
        (C) STRANDEDNESS:  single
        (D) TOPOLOGY:      linear (xi) SEQUENCE DESCRIPTION: SEQ ID NO:141:

AGCCUUAGGC AUCUCCUAUG GCAGG                                              25

(2) INFORMATION FOR SEQ ID NO:142:

(i) SEQUENCE CHARACTERISTICS:
        (A) LENGTH:        25 base pairs
        (B) TYPE:          nucleic acid
        (C) STRANDEDNESS:  single
        (D) TOPOLOGY:      linear (xi) SEQUENCE DESCRIPTION: SEQ ID NO:142:

CCUUAGGCAU CUCCUAUGGC AGGAA                                              25

(2) INFORMATION FOR SEQ ID NO:143:

(i) SEQUENCE CHARACTERISTICS:
        (A) LENGTH:        25 base pairs
        (B) TYPE:          nucleic acid
        (C) STRANDEDNESS:  single
        (D) TOPOLOGY:      linear (xi) SEQUENCE DESCRIPTION: SEQ ID NO:143:

UAGGCAUCUC CUAUGGCAGG AAGAA                                              25

(2) INFORMATION FOR SEQ ID NO:144:

(i) SEQUENCE CHARACTERISTICS:
        (A) LENGTH:        25 base pairs
        (B) TYPE:          nucleic acid
        (C) STRANDEDNESS:  single
        (D) TOPOLOGY:      linear (xi) SEQUENCE DESCRIPTION: SEQ ID NO:144:

AACCCACUGC UUAAGCCUCA AUAAA                                              25

(2) INFORMATION FOR SEQ ID NO:145:

(i) SEQUENCE CHARACTERISTICS:
        (A) LENGTH:        25 base pairs
        (B) TYPE:          nucleic acid
        (C) STRANDEDNESS:  single
        (D) TOPOLOGY:      linear (xi) SEQUENCE DESCRIPTION: SEQ ID NO:145:

CUGCUUAAGC CUCAAUAAAG CUUGC                                              25

(2) INFORMATION FOR SEQ ID NO:146:

(i) SEQUENCE CHARACTERISTICS:
        (A) LENGTH:        25 base pairs
        (B) TYPE:          nucleic acid
        (C) STRANDEDNESS:  single
        (D) TOPOLOGY:      linear (xi) SEQUENCE DESCRIPTION: SEQ ID NO:146:

UUAAGCCUCA AUAAAGCUUG CCUUG                                              25

(2) INFORMATION FOR SEQ ID NO:147:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:147:

UAAAGCUUGC CUUGAGUGCU UCAAG        25

(2) INFORMATION FOR SEQ ID NO:148:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:148:

AGUGCUUCAA GUAGUGUGUG CCCGU        25

(2) INFORMATION FOR SEQ ID NO:149:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:149:

GUGUGUGCCC GUCUGUUGUG UGACU        25

(2) INFORMATION FOR SEQ ID NO:150:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:150:

UGUUGUGUGA CUCUGGUAAC UAGAG        25

(2) INFORMATION FOR SEQ ID NO:151:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:151:

GUAACUAGAG AUCCCUCAGA CCCUU        25

(2) INFORMATION FOR SEQ ID NO:152:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:152:

CCUCAGACCC UUUUAGUCAG UGUGG        25

(2) INFORMATION FOR SEQ ID NO:153:

(i) SEQUENCE CHARACTERISTICS:
    (A) LENGTH:        56 base pairs
    (B) TYPE:          nucleic acid
    (C) STRANDEDNESS:  single
    (D) TOPOLOGY:      linear (xi) SEQUENCE DESCRIPTION: SEQ ID NO:153:

GAAAUGCUAG GCAGAAGUCA ACCAGAGAAA CACACGUUGU GGUACAUUAC CUGGUA          56

(2) INFORMATION FOR SEQ ID NO:154:

(i) SEQUENCE CHARACTERISTICS:
        (A) LENGTH:        56 base pairs
        (B) TYPE:          nucleic acid
        (C) STRANDEDNESS:  single
        (D) TOPOLOGY:      linear (xi) SEQUENCE DESCRIPTION: SEQ ID NO:154:

GAUGAAAUGC UAAGAAGCUG ACCAGAGAAA CACACGUUGU GGUACAUUAC CUGGUA          56

(2) INFORMATION FOR SEQ ID NO:155:

(i) SEQUENCE CHARACTERISTICS:
        (A) LENGTH:        56 base pairs
        (B) TYPE:          nucleic acid
        (C) STRANDEDNESS:  single
        (D) TOPOLOGY:      linear (xi) SEQUENCE DESCRIPTION: SEQ ID NO:155:

GGCAGCACUA UAAGAAGUAC ACCAGAGAAA CACACGUUGU GGUACAUUAC CUGGUA          56

(2) INFORMATION FOR SEQ ID NO:156:

(i) SEQUENCE CHARACTERISTICS:
        (A) LENGTH:        56 base pairs
        (B) TYPE:          nucleic acid
        (C) STRANDEDNESS:  single
        (D) TOPOLOGY:      linear (xi) SEQUENCE DESCRIPTION: SEQ ID NO:156:

UCCUUUUGUA UGAGAAGUUU ACCAGAGAAA CACACGUUGU GGUACAUUAC CUGGUA          56

(2) INFORMATION FOR SEQ ID NO:157:

(i) SEQUENCE CHARACTERISTICS:
        (A) LENGTH:        56 base pairs
        (B) TYPE:          nucleic acid
        (C) STRANDEDNESS:  single
        (D) TOPOLOGY:      linear (xi) SEQUENCE DESCRIPTION: SEQ ID NO:157:

UGCAUAUUGU GAAGAAGUUA ACCAGAGAAA CACACGUUGU GGUACAUUAC CUGGUA          56

(2) INFORMATION FOR SEQ ID NO:158:

(i) SEQUENCE CHARACTERISTICS:
        (A) LENGTH:        56 base pairs
        (B) TYPE:          nucleic acid
        (C) STRANDEDNESS:  single
        (D) TOPOLOGY:      linear (xi) SEQUENCE DESCRIPTION: SEQ ID NO:158:

CGCCCACCAA CAAGAAGCCC ACCAGAGAAA CACACGUUGU GGUACAUUAC CUGGUA          56

(2) INFORMATION FOR SEQ ID NO:159:

(i) SEQUENCE CHARACTERISTICS:

```
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:159:

AUGAAUUAGU UGAGAAGCUA ACCAGAGAAA CACACGUUGU GGUACAUUAC CUGGUA          56

(2) INFORMATION FOR SEQ ID NO:160:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:160:

CAGAGUCUGA AAAGAAGUCA ACCAGAGAAA CACACGUUGU GGUACAUUAC CUGGUA          56

(2) INFORMATION FOR SEQ ID NO:161:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:161:

UGAAAAUGGA UAAGAAGCAG ACCAGAGAAA CACACGUUGU GGUACAUUAC CUGGUA          56

(2) INFORMATION FOR SEQ ID NO:162:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:162:

UACCCCAUAA UAAGAAGUGA ACCAGAGAAA CACACGUUGU GGUACAUUAC CUGGUA          56

(2) INFORMATION FOR SEQ ID NO:163:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:163:

UUGUGGGUUG GGAGAAGUGG ACCAGAGAAA CACACGUUGU GGUACAUUAC CUGGUA          56

(2) INFORMATION FOR SEQ ID NO:164:

(i) SEQUENCE CHARACTERISTICS:
        (A) LENGTH:         56 base pairs
        (B) TYPE:           nucleic acid
        (C) STRANDEDNESS:   single
        (D) TOPOLOGY:       linear (xi) SEQUENCE DESCRIPTION: SEQ ID NO:164:

CUUCUUCUGC UAAGAAGCCA ACCAGAGAAA CACACGUUGU GGUACAUUAC CUGGUA          56

(2) INFORMATION FOR SEQ ID NO:165:

(i) SEQUENCE CHARACTERISTICS:
        (A) LENGTH:         56 base pairs
        (B) TYPE:           nucleic acid
```

```
            (C) STRANDEDNESS:     single
            (D) TOPOLOGY:         linear (xi) SEQUENCE DESCRIPTION: SEQ ID NO:165:

CUCCACAAUU AAAGAAGUGC ACCAGAGAAA CACACGUUGU GGUACAUUAC CUGGUA            56

(2) INFORMATION FOR SEQ ID NO:166:

(i) SEQUENCE CHARACTERISTICS:
            (A) LENGTH:          56 base pairs
            (B) TYPE:            nucleic acid
            (C) STRANDEDNESS:    single
            (D) TOPOLOGY:        linear (xi) SEQUENCE DESCRIPTION: SEQ ID NO:166:

CAAGUACUAU UAAGAAGUUG ACCAGAGAAA CACACGUUGU GGUACAUUAC CUGGUA            56

(2) INFORMATION FOR SEQ ID NO:167:

(i) SEQUENCE CHARACTERISTICS:
            (A) LENGTH:          56 base pairs
            (B) TYPE:            nucleic acid
            (C) STRANDEDNESS:    single
            (D) TOPOLOGY:        linear (xi) SEQUENCE DESCRIPTION: SEQ ID NO:167:

CAGCGUCAUU GAAGAAGCGC ACCAGAGAAA CACACGUUGU GGUACAUUAC CUGGUA            56

(2) INFORMATION FOR SEQ ID NO:168:

(i) SEQUENCE CHARACTERISTICS:
            (A) LENGTH:          56 base pairs
            (B) TYPE:            nucleic acid
            (C) STRANDEDNESS:    single
            (D) TOPOLOGY:        linear (xi) SEQUENCE DESCRIPTION: SEQ ID NO:168:

CUGGCCUGUA CCAGAAGCGU ACCAGAGAAA CACACGUUGU GGUACAUUAC CUGGUA            56

(2) INFORMATION FOR SEQ ID NO:169:

(i) SEQUENCE CHARACTERISTICS:
            (A) LENGTH:          56 base pairs
            (B) TYPE:            nucleic acid
            (C) STRANDEDNESS:    single
            (D) TOPOLOGY:        linear (xi) SEQUENCE DESCRIPTION: SEQ ID NO:169:

CUUGAUGCCC CAAGAAGUGA ACCAGAGAAA CACACGUUGU GGUACAUUAC CUGGUA            56

(2) INFORMATION FOR SEQ ID NO:170:

(i) SEQUENCE CHARACTERISTICS:
            (A) LENGTH:          56 base pairs
            (B) TYPE:            nucleic acid
            (C) STRANDEDNESS:    single
            (D) TOPOLOGY:        linear (xi) SEQUENCE DESCRIPTION: SEQ ID NO:170:

GAAAUGCUAG GCAGAAGUCA ACCAGAGAAA CACACGUUGU GGUACAUUAC CUGGUA            56

(2) INFORMATION FOR SEQ ID NO:171:

(i) SEQUENCE CHARACTERISTICS:
            (A) LENGTH:          56 base pairs
            (B) TYPE:            nucleic acid
            (C) STRANDEDNESS:    single
            (D) TOPOLOGY:        linear
```

(xi) SEQUENCE DESCRIPTION: SEQ ID NO:171:

GAUGAAAUGC UAAGAAGCUG ACCAGAGAAA CACACGUUGU GGUACAUUAC CUGGUA         56

(2) INFORMATION FOR SEQ ID NO:172:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO:172:

UGACAGCCGC CUAGCAUUUC                                                 20

(2) INFORMATION FOR SEQ ID NO:173:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO:173:

CAGCCGCCUA GCAUUUCAUC                                                 20

(2) INFORMATION FOR SEQ ID NO:174:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO:174:

GUACAGCCUA UAGUGCUGCC                                                 20

(2) INFORMATION FOR SEQ ID NO:175:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO:175:

AAACUGCCCA UACAAAGGA                                                  20

(2) INFORMATION FOR SEQ ID NO:176:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO:176:

UAACAGACUC ACAAUAUGCA                                                 20

(2) INFORMATION FOR SEQ ID NO:177:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO:177:

GGGCCGCCUG UUGGUGGGCG                    20

(2) INFORMATION FOR SEQ ID NO:178:

(i) SEQUENCE CHARACTERISTICS:
        (A) LENGTH:       20 base pairs
        (B) TYPE:         nucleic acid
        (C) STRANDEDNESS: single
        (D) TOPOLOGY:     linear (xi) SEQUENCE DESCRIPTION: SEQ ID NO:178:

UAGCAGACCA ACUAAUUCAU                    20

(2) INFORMATION FOR SEQ ID NO:179:

(i) SEQUENCE CHARACTERISTICS:
        (A) LENGTH:       20 base pairs
        (B) TYPE:         nucleic acid
        (C) STRANDEDNESS: single
        (D) TOPOLOGY:     linear (xi) SEQUENCE DESCRIPTION: SEQ ID NO:179:

UGACUGUUUU UCAGACUCUG                    20

(2) INFORMATION FOR SEQ ID NO:180:

(i) SEQUENCE CHARACTERISTICS:
        (A) LENGTH:       20 base pairs
        (B) TYPE:         nucleic acid
        (C) STRANDEDNESS: single
        (D) TOPOLOGY:     linear (xi) SEQUENCE DESCRIPTION: SEQ ID NO:180:

CUGCUGUUUA UCCAUUUUCA                    20

(2) INFORMATION FOR SEQ ID NO:181:

(i) SEQUENCE CHARACTERISTICS:
        (A) LENGTH:       20 base pairs
        (B) TYPE:         nucleic acid
        (C) STRANDEDNESS: single
        (D) TOPOLOGY:     linear (xi) SEQUENCE DESCRIPTION: SEQ ID NO:181:

UCACAGUCUA UUAUGGGUA                     20

(2) INFORMATION FOR SEQ ID NO:182:

(i) SEQUENCE CHARACTERISTICS:
        (A) LENGTH:       20 base pairs
        (B) TYPE:         nucleic acid
        (C) STRANDEDNESS: single
        (D) TOPOLOGY:     linear (xi) SEQUENCE DESCRIPTION: SEQ ID NO:182:

CCACAGACCC CAACCCACAA                    20

(2) INFORMATION FOR SEQ ID NO:183:

(i) SEQUENCE CHARACTERISTICS:
        (A) LENGTH:       20 base pairs
        (B) TYPE:         nucleic acid
        (C) STRANDEDNESS: single
        (D) TOPOLOGY:     linear (xi) SEQUENCE DESCRIPTION: SEQ ID NO:183:

UGGCAGUCUA GCAGAAGAAG                    20

(2) INFORMATION FOR SEQ ID NO:184:

(i) SEQUENCE CHARACTERISTICS:
        (A) LENGTH:       20 base pairs
        (B) TYPE:         nucleic acid
        (C) STRANDEDNESS:  single
        (D) TOPOLOGY:     linear (xi) SEQUENCE DESCRIPTION: SEQ ID NO:184:

GCACAGUUUU AAUUGUGGAG                                            20

(2) INFORMATION FOR SEQ ID NO:185:

(i) SEQUENCE CHARACTERISTICS:
        (A) LENGTH:       20 base pairs
        (B) TYPE:         nucleic acid
        (C) STRANDEDNESS:  single
        (D) TOPOLOGY:     linear (xi) SEQUENCE DESCRIPTION: SEQ ID NO:185:

CAACUGUUUA AUAGUACUUG                                            20

(2) INFORMATION FOR SEQ ID NO:186:

(i) SEQUENCE CHARACTERISTICS:
        (A) LENGTH:       20 base pairs
        (B) TYPE:         nucleic acid
        (C) STRANDEDNESS:  single
        (D) TOPOLOGY:     linear (xi) SEQUENCE DESCRIPTION: SEQ ID NO:186:

GCGCAGCCUC AAUGACGCUG                                            20

(2) INFORMATION FOR SEQ ID NO:187:

(i) SEQUENCE CHARACTERISTICS:
        (A) LENGTH:       20 base pairs
        (B) TYPE:         nucleic acid
        (C) STRANDEDNESS:  single
        (D) TOPOLOGY:     linear (xi) SEQUENCE DESCRIPTION: SEQ ID NO:187:

ACGCUGACGG UACAGGCCAG                                            20

(2) INFORMATION FOR SEQ ID NO:188:

(i) SEQUENCE CHARACTERISTICS:
        (A) LENGTH:       20 base pairs
        (B) TYPE:         nucleic acid
        (C) STRANDEDNESS:  single
        (D) TOPOLOGY:     linear (xi) SEQUENCE DESCRIPTION: SEQ ID NO:188:

UCACAGUCUG GGGCAUCAAG                                            20

(2) INFORMATION FOR SEQ ID NO:189:

(i) SEQUENCE CHARACTERISTICS:
        (A) LENGTH:       20 base pairs
        (B) TYPE:         nucleic acid
        (C) STRANDEDNESS:  single
        (D) TOPOLOGY:     linear (xi) SEQUENCE DESCRIPTION: SEQ ID NO:189:

UGACAGCCGC CUAGCAUUUC                                            20

(2) INFORMATION FOR SEQ ID NO:190:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:190:

CAGCCGCCUA GCAUUUCAUC                                            20

(2) INFORMATION FOR SEQ ID NO:191:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:191:

AAGCUAGUAC CAGUU                                                     15

(2) INFORMATION FOR SEQ ID NO:192:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:192:

AGUUUAGUAA AACAC                                                     15

(2) INFORMATION FOR SEQ ID NO:193:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:193:

UCAGAAGUAC ACAUC                                                     15

(2) INFORMATION FOR SEQ ID NO:194:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:194:

AUUGGGGUCU GCAUA                                                     15

(2) INFORMATION FOR SEQ ID NO:195:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:195:

GATCTACTGG CT                                                          12

(2) INFORMATION FOR SEQ ID NO:196:

```
    (i) SEQUENCE CHARACTERISTICS:
         (A) LENGTH:         13 base pairs
         (B) TYPE:           nucleic acid
         (C) STRANDEDNESS:   single
         (D) TOPOLOGY:       linear (xi) SEQUENCE DESCRIPTION: SEQ ID NO:196:

GTCTAGGATC TAC                                                              13

(2) INFORMATION FOR SEQ ID NO:197:

(i) SEQUENCE CHARACTERISTICS:
         (A) LENGTH:         11 base pairs
         (B) TYPE:           nucleic acid
         (C) STRANDEDNESS:   single
         (D) TOPOLOGY:       linear (xi) SEQUENCE DESCRIPTION: SEQ ID NO:197:

TCCTGGATGC T                                                                11

(2) INFORMATION FOR SEQ ID NO:198:

(i) SEQUENCE CHARACTERISTICS:
         (A) LENGTH:         11 base pairs
         (B) TYPE:           nucleic acid
         (C) STRANDEDNESS:   single
         (D) TOPOLOGY:       linear (xi) SEQUENCE DESCRIPTION: SEQ ID NO:198:

GGCTGACTTC C                                                                11

(2) INFORMATION FOR SEQ ID NO:199:

(i) SEQUENCE CHARACTERISTICS:
         (A) LENGTH:         13 base pairs
         (B) TYPE:           nucleic acid
         (C) STRANDEDNESS:   single
         (D) TOPOLOGY:       linear (xi) SEQUENCE DESCRIPTION: SEQ ID NO:199:

ATTGGTACAA GCA                                                              13

(2) INFORMATION FOR SEQ ID NO:200:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:200:

ACTTTTTACA ATAGC                                                            15

(2) INFORMATION FOR SEQ ID NO:201:

(i) SEQUENCE CHARACTERISTICS:
         (A) LENGTH:         14 base pairs
         (B) TYPE:           nucleic acid
         (C) STRANDEDNESS:   single
         (D) TOPOLOGY:       linear (xi) SEQUENCE DESCRIPTION: SEQ ID NO:201:

GCAATGAAAG CAAC                                                             14

(2) INFORMATION FOR SEQ ID NO:202:

(i) SEQUENCE CHARACTERISTICS:
         (A) LENGTH:         16 base pairs
```

(B) TYPE:            nucleic acid
        (C) STRANDEDNESS:    single
        (D) TOPOLOGY:        linear (xi) SEQUENCE DESCRIPTION: SEQ ID NO:202:

TTGTTATGAA ACAAAC                                                           16

(2) INFORMATION FOR SEQ ID NO:203:

(i) SEQUENCE CHARACTERISTICS:
        (A) LENGTH:          11 base pairs
        (B) TYPE:            nucleic acid
        (C) STRANDEDNESS:    single
        (D) TOPOLOGY:        linear (xi) SEQUENCE DESCRIPTION: SEQ ID NO:203:

AGGAGATGCC T                                                                11

(2) INFORMATION FOR SEQ ID NO:204:

(i) SEQUENCE CHARACTERISTICS:
        (A) LENGTH:          12 base pairs
        (B) TYPE:            nucleic acid
        (C) STRANDEDNESS:    single
        (D) TOPOLOGY:        linear (xi) SEQUENCE DESCRIPTION: SEQ ID NO:204:

ATAGGAGATG CC                                                               12

(2) INFORMATION FOR SEQ ID NO:205:

(i) SEQUENCE CHARACTERISTICS:
        (A) LENGTH:          11 base pairs
        (B) TYPE:            nucleic acid
        (C) STRANDEDNESS:    single
        (D) TOPOLOGY:        linear (xi) SEQUENCE DESCRIPTION: SEQ ID NO:205:

GAGGAGGTCT T                                                                11

(2) INFORMATION FOR SEQ ID NO:206:

(i) SEQUENCE CHARACTERISTICS:
        (A) LENGTH:          11 base pairs
        (B) TYPE:            nucleic acid
        (C) STRANDEDNESS:    single
        (D) TOPOLOGY:        linear (xi) SEQUENCE DESCRIPTION: SEQ ID NO:206:

CTTGAGGAGG T                                                                11

(2) INFORMATION FOR SEQ ID NO:207:

(i) SEQUENCE CHARACTERISTICS:
        (A) LENGTH:          11 base pairs
        (B) TYPE:            nucleic acid
        (C) STRANDEDNESS:    single
        (D) TOPOLOGY:        linear (xi) SEQUENCE DESCRIPTION: SEQ ID NO:207:

GTCTGACTGC C                                                                11

(2) INFORMATION FOR SEQ ID NO:208:

(i) SEQUENCE CHARACTERISTICS:
        (A) LENGTH:          12 base pairs
        (B) TYPE:            nucleic acid
        (C) STRANDEDNESS:    single (D) TOPOLOGY:      linear (xi) SEQUENCE DESCRIPTION: SEQ ID NO:208:

TGATGAGTCT GA                                                                          12

(2) INFORMATION FOR SEQ ID NO:209:

(i) SEQUENCE CHARACTERISTICS:
            (A) LENGTH:        13 base pairs
            (B) TYPE:          nucleic acid
            (C) STRANDEDNESS:  single
            (D) TOPOLOGY:      linear (xi) SEQUENCE DESCRIPTION: SEQ ID NO:209:

AACTTGATGA GTC                                                                         13

(2) INFORMATION FOR SEQ ID NO:210:

(i) SEQUENCE CHARACTERISTICS:
            (A) LENGTH:        14 base pairs
            (B) TYPE:          nucleic acid
            (C) STRANDEDNESS:  single
            (D) TOPOLOGY:      linear (xi) SEQUENCE DESCRIPTION: SEQ ID NO:210:

ATAGAGAAAC TTGA                                                                        14

(2) INFORMATION FOR SEQ ID NO:211:

(i) SEQUENCE CHARACTERISTICS:
            (A) LENGTH:        14 base pairs
            (B) TYPE:          nucleic acid
            (C) STRANDEDNESS:  single
            (D) TOPOLOGY:      linear (xi) SEQUENCE DESCRIPTION: SEQ ID NO:211:

TTGATAGAGA AACT                                                                        14

(2) INFORMATION FOR SEQ ID NO:212:

(i) SEQUENCE CHARACTERISTICS:
            (A) LENGTH:        14 base pairs
            (B) TYPE:          nucleic acid
            (C) STRANDEDNESS:  single
            (D) TOPOLOGY:      linear (xi) SEQUENCE DESCRIPTION: SEQ ID NO:212:

GCTTTGATAG AGAA                                                                        14

(2) INFORMATION FOR SEQ ID NO:213:

(i) SEQUENCE CHARACTERISTICS:
            (A) LENGTH:        13 base pairs
            (B) TYPE:          nucleic acid
            (C) STRANDEDNESS:  single
            (D) TOPOLOGY:      linear (xi) SEQUENCE DESCRIPTION: SEQ ID NO:213:

GGCAGUCAGA CUC                                                                         13

(2) INFORMATION FOR SEQ ID NO:214:

(i) SEQUENCE CHARACTERISTICS:
            (A) LENGTH:        34 base pairs
            (B) TYPE:          nucleic acid
            (C) STRANDEDNESS:  single
            (D) TOPOLOGY:      linear (xi) SEQUENCE DESCRIPTION: SEQ ID NO:214:

GAGUCUCUGA UGAGGCCGAA AGGCCGAAAC UGCC                                          34

(2) INFORMATION FOR SEQ ID NO:215:

(i) SEQUENCE CHARACTERISTICS:
        (A) LENGTH:            13 base pairs
        (B) TYPE:              nucleic acid
        (C) STRANDEDNESS:      single
        (D) TOPOLOGY:          linear (xi) SEQUENCE DESCRIPTION: SEQ ID NO:215:

CAGACUCAUC AAG                                                                 13

(2) INFORMATION FOR SEQ ID NO:216:

(i) SEQUENCE CHARACTERISTICS:
        (A) LENGTH:            34 base pairs
        (B) TYPE:              nucleic acid
        (C) STRANDEDNESS:      single
        (D) TOPOLOGY:          linear (xi) SEQUENCE DESCRIPTION: SEQ ID NO:216:

CUUGAUCUGA GGAGGCCGAA AGGCCGAAAG UCUG                                          34

(2) INFORMATION FOR SEQ ID NO:217:

(i) SEQUENCE CHARACTERISTICS:
        (A) LENGTH:            13 base pairs
        (B) TYPE:              nucleic acid
        (C) STRANDEDNESS:      single
        (D) TOPOLOGY:          linear (xi) SEQUENCE DESCRIPTION: SEQ ID NO:217:

CUCUAUCAAA GCA                                                                 13

(2) INFORMATION FOR SEQ ID NO:218:

(i) SEQUENCE CHARACTERISTICS:
        (A) LENGTH:            34 base pairs
        (B) TYPE:              nucleic acid
        (C) STRANDEDNESS:      single
        (D) TOPOLOGY:          linear (xi) SEQUENCE DESCRIPTION: SEQ ID NO:218:

UGCUUUCUGA UGAGGCCGAA AGGCCGAAAU AGAG                                          34

(2) INFORMATION FOR SEQ ID NO:219:

(i) SEQUENCE CHARACTERISTICS:
        (A) LENGTH:            14 base pairs
        (B) TYPE:              nucleic acid
        (C) STRANDEDNESS:      single
        (D) TOPOLOGY:          linear (xi) SEQUENCE DESCRIPTION: SEQ ID NO:219:

GGAAGUCAGC CUAA                                                                14

(2) INFORMATION FOR SEQ ID NO:220:

(i) SEQUENCE CHARACTERISTICS:
        (A) LENGTH:            37 base pairs
        (B) TYPE:              nucleic acid
        (C) STRANDEDNESS:      single
        (D) TOPOLOGY:          linear (xi) SEQUENCE DESCRIPTION: SEQ ID NO:220:

```
UUAGGCUCUG AUGAGCCGCG AAAGCGGCGA AACUUCC                                        37

(2) INFORMATION FOR SEQ ID NO:221:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:221:

AUUGGGGUCU GGAUA                                                                15

(2) INFORMATION FOR SEQ ID NO:222:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:222:

UAUCCACUGA UGAGGCCGAA AGGCCGAAAC CCCAAU                                         36

(2) INFORMATION FOR SEQ ID NO:223:

(i) SEQUENCE CHARACTERISTICS:
        (A) LENGTH:        13 base pairs
        (B) TYPE:          nucleic acid
        (C) STRANDEDNESS:  single
        (D) TOPOLOGY:      linear (xi) SEQUENCE DESCRIPTION: SEQ ID NO:223:

GACCGUCAGA CGC                                                                  13

(2) INFORMATION FOR SEQ ID NO:224:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:224:

GCGUCUCUGA UGAGGUCCGA AAGGACCGAA ACGGUC                                         36

(2) INFORMATION FOR SEQ ID NO:225:

(i) SEQUENCE CHARACTERISTICS:
        (A) LENGTH:        11 base pairs
        (B) TYPE:          nucleic acid
        (C) STRANDEDNESS:  single
        (D) TOPOLOGY:      linear (ix) FEATURE:
        (D) OTHER INFORMATION:   The letter "N" stands for any
            base. The letter "H" stands
            for A, U, or C.

(xi) SEQUENCE DESCRIPTION: SEQ ID NO:225:

NNNNUHNNNN N                                                                    11

(2) INFORMATION FOR SEQ ID NO:226:

(i) SEQUENCE CHARACTERISTICS:
        (A) LENGTH:        32 base pairs
        (B) TYPE:          nucleic acid
        (C) STRANDEDNESS:  single
        (D) TOPOLOGY:      linear
```

(ix) FEATURE:
    (D) OTHER INFORMATION: The letter "N" stands for any base.

(xi) SEQUENCE DESCRIPTION: SEQ ID NO:226:

NNNNNCUGAN GAGNNNNNNN NNNCGAAANN NN                            32

(2) INFORMATION FOR SEQ ID NO:227:

(i) SEQUENCE CHARACTERISTICS:
        (A) LENGTH:       20 base pairs
        (B) TYPE:         nucleic acid
        (C) STRANDEDNESS: single
        (D) TOPOLOGY:     linear (xi) SEQUENCE DESCRIPTION: SEQ ID NO:227:

CUGUAGUCCA GGAAUAUGGC                                          20

(2) INFORMATION FOR SEQ ID NO:228:

(i) SEQUENCE CHARACTERISTICS:
        (A) LENGTH:       38 base pairs
        (B) TYPE:         nucleic acid
        (C) STRANDEDNESS: single
        (D) TOPOLOGY:     linear (xi) SEQUENCE DESCRIPTION: SEQ ID NO:228:

GCCAUAUUCC UGAGAAGCAG ACCAGAGAAA CACACGCG                      38

(2) INFORMATION FOR SEQ ID NO:229:

(i) SEQUENCE CHARACTERISTICS:
        (A) LENGTH:       21 base pairs
        (B) TYPE:         nucleic acid
        (C) STRANDEDNESS: single
        (D) TOPOLOGY:     linear (xi) SEQUENCE DESCRIPTION: SEQ ID NO:229:

CGCGUGGUAU AUUACCUGGU A                                        21

(2) INFORMATION FOR SEQ ID NO:230:

(i) SEQUENCE CHARACTERISTICS:
        (A) LENGTH:       22 base pairs
        (B) TYPE:         nucleic acid
        (C) STRANDEDNESS: single
        (D) TOPOLOGY:     linear (xi) SEQUENCE DESCRIPTION: SEQ ID NO:230:

GACUGUAGUC CAGGAAUAUG GC                                       22

(2) INFORMATION FOR SEQ ID NO:231:

(i) SEQUENCE CHARACTERISTICS:
        (A) LENGTH:       40 base pairs
        (B) TYPE:         nucleic acid
        (C) STRANDEDNESS: single
        (D) TOPOLOGY:     linear (xi) SEQUENCE DESCRIPTION: SEQ ID NO:231:

GCCAUAUUCC UGAGAAGCAG UCACCAGAGA AACACACGCG                    40

(2) INFORMATION FOR SEQ ID NO:232:

(i) SEQUENCE CHARACTERISTICS:
        (A) LENGTH:       21 base pairs
        (B) TYPE:         nucleic acid

```
        (C) STRANDEDNESS:   single
        (D) TOPOLOGY:       linear (xi) SEQUENCE DESCRIPTION: SEQ ID NO:232:

CGCGUGGUAU AUUACCUGGU A                                                      21
```